US010174296B2

(12) United States Patent
Shaw, IV et al.

(10) Patent No.: US 10,174,296 B2
(45) Date of Patent: Jan. 8, 2019

(54) MICROORGANISMS ENGINEERED TO USE UNCONVENTIONAL SOURCES OF PHOSPHOROUS OR SULFUR

(71) Applicant: Novogy, Inc., Cambridge, MA (US)

(72) Inventors: Arthur J. Shaw, IV, Belmont, MA (US); Colin R. South, Lexington, MA (US); Johannes P. Van Dijken, Leidschendam (NL)

(73) Assignee: Novogy, Inc., Cambridge, MA (US)

( * ) Notice: Subject to any disclaimer, the term of this patent is extended or adjusted under 35 U.S.C. 154(b) by 47 days.

(21) Appl. No.: 14/914,817

(22) PCT Filed: Aug. 27, 2014

(86) PCT No.: PCT/US2014/052841

§ 371 (c)(1),
(2) Date: Feb. 26, 2016

(87) PCT Pub. No.: WO2015/031441

PCT Pub. Date: Mar. 5, 2015

(65) Prior Publication Data

US 2016/0215274 A1 Jul. 28, 2016

Related U.S. Application Data

(60) Provisional application No. 61/870,469, filed on Aug. 27, 2013.

(51) Int. Cl.

| | |
|---|---|
| ***C12N 9/00*** | (2006.01) |
| ***C12P 1/02*** | (2006.01) |
| ***C12N 9/02*** | (2006.01) |
| *C12P 7/00* | (2006.01) |

(52) U.S. Cl.

CPC .............. *C12N 9/0004* (2013.01); *C12P 1/02* (2013.01); *C12Y 120/01001* (2013.01); *C12P 7/00* (2013.01)

(58) Field of Classification Search

None

See application file for complete search history.

(56) References Cited

U.S. PATENT DOCUMENTS

| | | | |
|---|---|---|---|
| 2006/0051847 A1 | 3/2006 | Gunnarsson et al. | |
| 2012/0295303 A1 | 11/2012 | Herrera-Estrella et al. | |
| 2017/0226493 A1* | 8/2017 | Callewaert ........... | C12N 9/2488 |

FOREIGN PATENT DOCUMENTS

| | | |
|---|---|---|
| EP | 2034026 A1 | 3/2009 |
| WO | WO-2010/058298 A2 | 5/2010 |
| WO | WO-2012/147556 A1 | 11/2012 |
| WO | WO-2014/024998 A1 | 2/2014 |

OTHER PUBLICATIONS

International Search Report dated Feb. 24, 2015, from PCT/US14/52841.

Costas et al., "Purification and Characterization of a Novel Phosphorus-oxidizing Enzyme from Pseudomonas stutzeri WM88," J Biol Chem, 276(20): 17429-17436 (2001).

Kanda et al., "Application of a Phosphite Dehydrogenase Gene as a Novel Dominant Selection Marker for Yeasts," J Biotechnol, (182-183): 68-73 (2014).

Sodoyer et al., "Antibiotic-Free Selection for Bio-Production: Moving Towards a New "Gold Standard"," 531-548 (Apr. 4, 2012).

Supplementary Partial European Search Report for European Application No. EP14839721 dated Dec. 15, 2016.

Tai et al., "Engineering the Push and Pull of Lipid Biosynthesis in Oleaginous Yeast *Yarrowia lipolytica* for Biofuel Production," Metab Eng, 15:1-9 (2013).

Tsigie et al., "Bioethanol Production from Yarrowia lipolytica Po1g Biomass," Bioresource Technol, 145: 210-216 (2013).

Jakobiak et al., "The bacterial paromomycin resistance gene, aphH, as a dominant selectable marker in Volvox carteri," Protist, 155(4):381-393 (2004).

* cited by examiner

*Primary Examiner* — Nancy A Treptow

(74) *Attorney, Agent, or Firm* — Albert Shung

(57) ABSTRACT

Disclosed are genetically engineered organisms, such as yeast and bacteria, that have the ability to metabolize atypical phosphorus or sulfur sources. Fermentation methods using the genetically engineered organisms are also described. The fermentation methods are robust processes for the industrial bioproduction of a variety of compounds, including commodities, fine chemicals, and pharmaceuticals.

6 Claims, 36 Drawing Sheets

Specification includes a Sequence Listing.

Figure 1

*Pseudomonas stutzeri* WM88 ptxABCDE

```
atgacgccccatccgatacaggacgccgtgctgcgggtcgaccggttgagcgtcgtctatccaggcggcgtgaca
gccctacgcgatacctcgattgcatttcggcgtggtgagttcaccgtgctgcttggtctctcgggcgcaggcaag
tcgaccttgctccgtagtctcaatcgactcgtcacgcccactggcggcagtgtcaccagcgaactcggtgaactc
ggcagcggctcggccttgcgtcagcatcgtcggcgtaccgccatgatctttcagcaccaccagctaatcgaacgt
caaagcgcactggctaatgtgctgaccggtcggctggcctttcacaacacgctccgctcgctgtttcctctgccg
cgtgccgatcaggagattgcgctcagttgcctcgctcgggtcggtctggcagacaaggcgctaagccgggtggac
aaactgtccggtggccagcagcagcgggtaggcatcgcgcgtgcgctagcgcaacagccggcgatcattctggcc
gatgagccggtagccagtctcgacccggccacttcggtccgtgttctcggattgctgcgcgacatctgcaaggaa
gacggcatcaccgccatcgtttcgctgcatcaactcgaatatgcccgccgcttcgccgatcgcgtcgtcgggctg
gccgattctcagatcgttttcgatgccgcgccctcggaactcaccgatgcgcagcttgagcgcatctatgcaggc
cgctctacgactcagccagcgaatgctccggctgaaccacctgtcatgctcgaaccttcactggagatgtcccga
tgaaacgcttatccgcgctcttattgacttgcttgctgtccgctgtttcaagtttgtccgccctagcggccgatg
ccgatccggatgtgctaaaggttgccctgctgccggacgaaaacgcctccgagctgatcaagcgtaaccagccgc
tgaaggattatctggaagagcatctggacaagaaggtgcagctgatcgtaaccaccgactattcctcgatgattg
aggcgatgcgctttggccgtatcgacctggcgtatttcggtccgctgtcctacgtcatggccaaaagcaaaagcg
acatcgagcccttcgctgccatggtcatcgacggcaagccgacctatcgctcggtgattatcgccaatgtggcgt
caggcgtgaatgagtatgccgaccttaagggcaagagaatggcctatggtgaccgggcatcgacgtccagccatt
tgattcccaaaaccgtgcttcttgagacggccgatttgacgggtgggcaggactacgaacaacatttgtgggca
cgcatgacgccgttgccgtcaacgtggcgaacggcaacgccgatgcgggtgggctgtcggaggtaatttcaatc
acgcagccgaacgtggcctgatcgatccgagcaaggtgaaagtacttggttacagcggcgaatacccccagtacc
cctgggcgatgcgctcgaacctgagccccgagctgaaaaccaaggtgcgggatgtattcgtcggtatcgacgatc
ccgaagtgctgcgcaacttcaaggccgaggccttcgcgccaatcaccgacgccgactacgatgtgatccgcaaca
tgggatcgctgctcggcctcgacttcgccacgatgtgagcaccgatatgtcttctcattacgacgtgcaggcgct
gcctgcagagcaacgcgagcacatccttcgaggcttcggcctcggttggtggcgccagctggggcaggtggcgat
tgtattcggagtggtgctgttggcctgctggtacgtggggctgctcgatgccaccacgctgctgaacgggctgcc
ctccatcgcgaccctggcaggcgaggccatgccgccagacttttcgggctatcgaagctggattcgccccttgat
cgacaccttggcgatgagcatcgccggtacggccatcgcagtggtgttctcgctggtggtggccttcgttgcagc
gcgcaatacggcgccgcacccccttgtgttcggtgttgcccgggtgctgctcaatgccctgcggtcggtgccgga
gctgatcatgggcatcatcttcgttgcagccgtagggttcggcgccttgccgggcgtgcttgccctgggtctgca
ttcggtcggcatggtcggcaagttcttcgccgaggccatcgagcacgtcgacgaagcgccggtggaagccgctcg
ggcggcgggggctacgccgatgcaagtgctgctgcacgcggttttgccacaggtgacgccgcagttcgccgacgt
ggcgatctaccgctgggaatacaactttcgcgcctccaccgtgatgggcatggttggcgccggcggtatcggctt
cgaactcatgggctcgctgcgcatcatgcagtaccaggaggttgcagcaatcctgctggtcatcctggccatggt
cacgctagtagacgccttcagtggcgtgctgcgcaaacatttcaaataggacaaaccatgctgccgaaactcgtt
ataactcaccgagtacacgatgagatcctgcaactgctggcgccacattgcgagctgatgaccaaccagaccgac
agcacgctgacgcgcgaggaaattctgcgccgctgtcgcgatgctcaggcgatgatggcgttcatgcccgatcgg
gtcgatgcagactttcttcaagcctgccctgagctgcgtgtagtcggctgcgcgctcaagggcttcgacaatttc
gatgtggacgcctgtactgcccgcggggtctggctgaccttcgtgcctgatctgttgacggtcccgactgccgag
ctggcgatcggactggcggtggggctggggcggcatctgcgggcagcagatgcgttcgtccgctctggcgagttc
cagggctggcaaccacagttctacggcacggggctggataacgctacggtcggcatccttggcatgggcgccatc
ggactggccatggctgatcgcttgcagggatggggcgcgaccctgcagtaccacgaggcgaaggctctggataca
caaaccgagcaacggctcggcctgcgccaggtggcgtgcagcgaactcttcgccagctcggacttcatcctgctg
gcgcttcccttgaatgccgatacccagcatctggtcaacgccgagctgcttgccctcgtacggccgggcgctctg
cttgtaaaccccgtcgtggttcggtagtggatgaagccgccgtgctcgcggcgcttgagcgaggccagctcggc
gggtatgcggcggatgtattcgaaatggaagactgggctcgcgcggaccggccgcggctgatcgatcctgcgctg
ctcgcgcatccgaatacgctgttcactccgcacatagggtcggcagtgcgcgcggtgcgcctggagattgaacgt
tgtgcagcgcagaacatcatccaggtattggcaggtgcgcgcccaatcaacgctgcgaaccgtctgcccaaggcc
gagcctgccgcatgttgaatccggtctggctgaagagcctggtagcgatcgttcaaacaggcagttttcagagcg
cggcgagggcgttggggctggcccagccgacggtgtcgcagcacttgcagaagcttgaagagcaggtcggcgtaa
cgctggtgcagcgcagtcgtagcggctgccagcctaccacacgggcgctggccttcatgccgcatgcgaccgcct
tgctcgacatgcacgcccgggcgctagaagccctgcatggcaatcgtgagcgcgtcggggccagctccaacatcg
gcacctaccttctccagccattcgtgcgcaactatctgacgaccgcaaatgagaggggcgaggtggatctgcgca
tcgccgccaacccggatgtggccgaccagctactggcgggccagctcgacgccgcgatcatggaatggtggctac
ctc
```

Figure 1 (continued)

accccgacttcgaataccgcctctggcgggtcgagccgctggtgcttatcgtcagccccgaccatgcgctggctg
aagcagggtgcatagaacgtgatcgtctggtggacctgccgatgctgggaggtgaaccgggtagcggtacctag Pseudomonas stutzeri WM88 htxABCDEFHGIJKLMN atgtttgcagagcagcaacgcgaatatctcgacaagggatatacgaagattgaaagctttttctccgcggaggaa
gtagcgaagattcttgaagacgtcaagcaaattgaattgggagctattggcgtagcttcggacaatgagacttac
cagttcgaaaagaagaatggcgagacgacgaagctactgcgtcgcgtcgagaatcctcacctttatttcgatgca
atagattctttggtcaggtcggaaaaaatcgtcgatttgcttcggcatttcctgggcgaaaacatccgtttgcac
aatagcaaaatcaacttcaagccgccatcaggcgcgccagtccagtggcatcaggactgggcattctatccccac
acaaacgatgatttttcttactctcggaatttttcctcgacgagacaagtgagaaaaatggcgcgatggcatgcttg
ccaggctcccacaaaggaaaagtgtacgaccaccggaacgtcgagacgggcgagttttgccacgcgatctctcgc
tccaactgggacgaagcgctcgacccgacagaaggggagttactgacgggacccgtaggaactgtcacgttgcat
cacgtccggacccttcatggttcaggcccaaaccactcaacgatcaggcggcgtttctgctcatcggctatgcc
gcggctgatgcctggccacttctgggctgtggcaactatggggattatgaaagcctcatggtctctggccgatcc
accgtattcccgcgcatggtggaactccctttgactgtcccgtatccgttgtcgatgtacggtgatcgcatcttt
gaaagtcaacgagctttgactcaaaagtactactgaagtctttaactcactgaggtcataatgcaagtttttact
ctgttttcgaaattcaagaaggcgttaacgcgcgccattcttgcctttatcgccacaatcatagtgtgcacaccc
gcgcaggcagctgaggttgtcaatggtaaacttcacctgcgttttgcaattgcgccgatgcgtccaacgcctagc
cagaccatcaaagagtttgagccgatattcaagtatctcgccgaccagctcggcgcgacctatgaaatcgtctcc
ccggaaagctgggcggcaatatctgtggcaatgacaaatggccatgtcgatgtgggctggctcggaccctggggc
tatgtcttgtcgaataaaaaggccggcaccgaagtgcttgcaacggtcaagtaccgcggggagccgttctacaaa
gccctcattgtcggtcgcgccgatctgccgatcaaaaaatggcccgaggacgcgaagggtttgaagctgtcactc
agtgatcagggcaacacttctggctggctcatcccgatggcgtacttcaagagcatcggcatcgaccctgcgagc
tattttgaatatcgtgaaggtgccacgtttggccagaacgaatcacagattcagcacggactgatcgacctcgga
tccgatatggatcggggccggaacgggatgatcgaagcgggtcaaatcgatccttcgaagtccaagatcgtgtgg
gaatccagcaagctgccgaacgacgcgatatccgtgccgaaggatttgatcctgctctgaaagcgcgcatcacg
gaaatactgacgtccttgtccgaagagaaagcacagtcgctgatgggctcgggctataacggcttcgtgaaggca
aagcacagcgattacaaggtaatcgaagacgccggccgcatcctgggaaaactgtaaagcacgaggggtccgttc
ttggatgagggcagcggacgacaaggtggactgacgcacgccagctccttgtctccgctgcacgaacatacgggc
gcgcatcgcaataccacagaggatgaaccaatgaatcagcgaatcgaagaagtcatgctggctaatgtcaagagg
gacgtagccaggagaaagcggcatttgcaacgtcggtcgtagtactcagtttgctggcagtggcctggtacgtg
tgtcagatagaattccagaagctaggcgccggtttaccgagactatggtcattcgtcgtgcagatgtttccaccc
gacctgagcgacctggacgtcattctaaaggggctggcgagacgctcgccatggcgacgattggcacgatattc
gccacaatcattgcatttccgctggcactcatggctgcgcgtaatacctgtccgaacaagtggacctatcgggta
tcccgcgccatcctgaacgccagccgcggcacggagacatttgtctatgcacttgtatttgtagcagcagtgggc
ttcggtccgttctccggcgtactggccattactttccacatggtaggggcaatcggcaaaatgtttgctgaagcc
atcgagcccgttgaccaagggccgttggatgcgctcgccttgaccggtgccagcagggcaaagattatccgctac
ggtctgatcccggatgttatgccgcacctgatcgcgagcgttctatacatttgggaattcagtgtcagaacgtcc
acagtactgggcatcgtaggcgcaggtggaattgggcagaccctgaaagatactgtggacttgttggaattcaac
aagatgattacggtactggcggttgtattgctgatggtgtcggcaatcgatttcatcagtgaccggctcaggtac
ttgatattggacacaaaacgcgagggattcgaaactctccctgcgaataactgattgcttcacgtattactggaa
gggaggttcgcaatgaaagatgtagcgttgcagttaaagaatgtcggtaagtcatacggcaataaagttgtcctg
gaatcgattgacttcgaagtacgtcacggctcaatggttgccttgctcggcacaagcggggcagggaagtcgacg
ctttttccgatgtctcactggccttgagccgattgactccggttctatcgtggcgctcggagaatccatacatgaa
ctgtctccggcgcgtctgcgggcagtacgtggccagatcgggttcgtgttccaacaactgcacctggtgaaaagg
ttctcagcactcgagaatgtattgggtgcgcgtctggcagagatgcccatttggcgcgtcacattgaaagcttc
agccgggctgacaaagtgctcgcgttcgaatgtctggaccgggtcggcatgctcgattatgcaaacacgcctacg
caactgctgtcaggcggtcagcaacagcgtattgcgatagcgcgagccttggcgcagaagcccaagattattatt
gcggacgaacccgtctccagcctcgatccgctgacggcgcgctcggttctgcaaacgctgaaagccgcggctaca
gatcttaatgtcgcggtcctgtgcagcctgcaccaggtagacctggcccgtgagtttggcgaccgcatcgtgggc
atgcgcgacggacgtgtcgttttcgacggcacgccagcggaattcaccgacgagcgcgtgcatgcgctttaccag
gtgcccgctgggaagatgcaccagcggccgagagcgacgcgcagcactcggtggccggtctggctgtggcatgag
gggcgaagcgatgaccacatccacacgccccatacccgtgccgccccagggcaccgcactgcactggcacctgag
cgcgccctacaacgccaaacatctgctggtgctgatcgccgtcatggtgctgttgttcgtgaccggaca

Figure 1 (continued)

acgcaccgaaatggaccgcatggtggccatgacggcacaggccgtggccaagaccgtgggcctggctgacgattc
acaagtcgcgcggcttgtcgcgcgtcggtcaagccatgtggccacccgccatcgcagaaaccgaagaggtggg
ccggattcaggacctggatcgccagaagctgcccctgttctcgcacatcgagacccaggagcgcgtcgagcagaa
gatgaatctggacacgctgaagatggaagccacgacggaaaccgtcgaagtgctggtcaagccggtcggctatgt
ctggacggttttcatcaagatgatcgagacctggagattgcgctgtggggcacgatcctgtcggtgctggtgtcg
attcccctggcgtatttcgcggcccgcaactactagccccaaccgttttacctacaccgctgcccgcggcaccat
cagtctgctgcgttcagcgccggaactcatcgtcgctttgttcctggtgctggcctacggctttggccccatcgc
tggcgtgctggcgctgggcctgcatgcggccggcttcctgggcaagttctacgccgaggacatcgagaacgccga
caagaagccgcaagaggcgctggaggccatcggcgcgggcaagctcaagacgctgtggtacggcgtcatcccccca
ggtcttgccgcaatacatcgcctacaccgcctacatcctggaccgcaacctgcgcatggccaccgtcatcggtct
ggtgggcgcgggcggcatcggccaggaactcaagggccgttttgacatgttccagtacggccatgtcatgaccat
cctgatcgcgatcttcgtctttgtgttcgtgctggaccagttgcaggcgcgcatccgcgccaagctgatctgagg
cgaccgctgacaacaaggaacaacatgacaaacacttctgaagcaccggatcgtgcgcagtggctgcggctgtgg
tcggccttgccggccgcagcggtcaaggccctggcggccgatctggcgggccagcaccgggtcgaagacctggcg
ttgccgcaatccggtctgggcctgctgccgctgaccgacagcgccctgggcgatacctatttcatcggtgagatt
cccttggcacaagcgcatgtgcgggtcacgaccacccaagggcagtcgatcgaaggcgcggccattctggtggac
gaccgtgccggtgtggcccgttccatggccatcctggacgcggtgctggcggcccgcatgccaggttgtgaagcg
gccctgcggttgctcacccagggtgcgaccgccgtggcggaacaaggccgccagcgccgcgccttactcgcggcc
acgcgggtggactttgccctgctgggaacgaacgaggaggacgatgatgaatgagactgggatggcggcggcacc
ggcagaagccgcgtggcgcatctggcaagcgccgcgccagcaaacggcgtttcgccagttgatgaccgcgttttc
ctatccgggccgcgtggtgccactggccgatggcgctgaatcggcgctcctgctggtgttgaccaccctggtgga
cagcgcctgtgcgctggccgatccgctgcacgcgctatcaagcgacgatctgcgccgactgggcgtgcgctcggc
cagtgtggaggcggccgagttcgtgctggccgatggcaaccgtttgctggaggccacgccgcgcctgggatcgct
ggaaaaccccgaacaaggcgcgaccgtggtgatgcgcgtctcccgtttcggtgagggtccccatctgcggctcac
cgggccgggtattcaacacgagcaggtgctgcaggtcagcggcatcgatccgggctggtggaagcaacggtccga
atggaatgcccacttcccgctgggcgtggacctgattctggtgagcgggcacgaggtcgcggtattgccccgaac
caccccacatcaacctcaaaggagcccactgatgggatacgttgccatcaagggcggtggccgggccatcgccggt
gccgaagccgccgtcgaagccctgcgctgcgccgaagggccagcgggtacgccgctcacgctgtcggccatcgaa
cagcagttgcggttgctgacatcgcgcgtcgtgtcggaaggggcctctaccacccacgcctggccgctctggcc
atcaaacagatgcagggcgacacactggaagcggcgttcgctctgcgcgcctaccgctccaccaagccacgcctg
atggatgtgccggtgcaggacacgagccgcatgcgcctaatccgccggatttcgagcgctttcaaggacatcccc
ggcggacagatgctgggcccgaccaccgactacgcgctgcgcctgatgcgtctggatttggccaacgagtcgccc
gaggactttcgcgcggtctcgcggcggtttctggacagcgtggccgacaccgacctgcccgacagcttccccaag
gtggtcgatgccttgcgtgacgaaggcttgctgccgccgctgacccggcgcgcccatgcggcgttcgacatcacc
cgcgacccgctggttttcccagtgccgcgttcggcggccctggccaccatggcacgcgccgaaaccggctcgctc
ttggcgattgcgtattccaacatgcgtggctatggcgacgtgcaccccaccatcgccgagctgcgcgtgggctat
gtgccggtgatgctgccgcacccggtgacaggcgagcccatcgaagccggtgaggtactgatgaccgaatgcgaa
gtggtggccatgtttgagggtgatgctaccgacggcccacccactttcaccctaggctatggcgcctgtttcggt
cacaacgaagtcaaggccatcgccatggccatcctcgaccgcgccctgcaaaagggtatgcgcgacggtcccagc
aacccgtcggaagacccggaattcgtgctgctgcacgtcgatggcgtggattcgatgggctttgccagtcactac
aagatgccgcactacgtgaccttccagtccgacatggaccggctgcgcaccacgcaggacaaggcaaccgcacaa
ccgacccaagaaggagcgccatcatgaacccgggctacgaactgcccctggacgaggcgggctacagcttcggct
tcctggacgaatacgccaagcgcgaggtgcgccgcaccatcctcaaggcgatcagcatccccggttaccagacgc
cctatgcctcacgcgaaatgcctatggggcgcggctttggcaccggcggtctgcaggttacgctgtcgctgattg
gcgagggcgacaccctgaaggtgatcgaccagggcgcggacgactccgtcaacgcggtgaacctgcgtcactttg
tggaactgacctgcccgggcgtggacaccacagaacacacgcttgatgccactctgatccagtcgcgccaccgca
ttccggaaacgccgctgaccgaagcgcaggtgttgatcctgcaagtgccgtatccggacccactggtggtggtgg
aaccctccgaggctcgacgcaaggtcatgcacggcgaaggcgactattcgcggctgctgaccaagctgtacgagg
acatcgtgcagtttgacgagatcaccatctcgcaccgctacccccacgcgcatcaacggccactatgtgatcgacc
ccagcccgatcccgcgctacgacgtgccgcagttgcaccagagcccggcgctgatcctgctgggtgcggggcgcg
agaaaaaaatctatgcggtgccgccgtacacccgcgccgacccgctggcgttcgacgacgtgccattccgcaccg
aagacttcaccaacgaacacggccagcgccgcgcctgcgaacggtgcggcgccaccgacagcttcctcgacgagc
tcattgccgacgatggcggcaagcactggcattgctcggactcggattttgcaatagccgtatggcccgccagg
ctgaacaagctcaggagaccacggtatgaaaaaaattctggaagtacgcggactgaccaagatccacggccgggg
ttgcgaactctgcctggagagcactggccccgacatggacaccaacatctgcccacactgtggctcggtggtggc
ctgcccacaacatcagcctggacctgcacgagggcgagatcctcggcatcatgggcgagtccggcagcggcaagtc
caccgtggtcaa

Figure 1 (continued)

gacgctgttcttcgacgatgagcccaccgctggtgaagccctgtttttgacggcgagcgccagtgggacatgtt
cgcgctcaacgccgcgcagcagcgctggcttgcgcaaccaccgctttggcatggtgtaccagaacccgcatctgg
gactcaatttcaacgtctcggccggcggaaacatttgccgagcgccttgctgatgagcgacctggcccactacgg
cgaaatccgcgaacgggcgcgcagcttgttggcgcgcactgaggtgttggcagaacgcatggacgagtcgcccaa
gaagttctcgggcggcatgcagcagcgcgtgcagatcgccaaggcactggccacccagccgccgctgctctacct
cgacgaggtcaccaccggcctggacctttcggtgcaggcgcgcatcctggacctgattctggaaatccagcagga
gctgggcaccgccatgatcgtggtcacccacgatctgggtgtcatccgcctgctgaccggacgcacgatcgtcat
gaaatacggccgcggtcatcgaagtccgggctgaccgaccagatcctcgaagacccccagcacgcctacacccag
cgcctggtcgcgtcggcttctctgaggaaacctgaatcatgcaagaagccatcctcaaaatcgaaggtctctcca
aacagttccagctgcacgaccagaacaaactgatcccgtcgtgtgcacaggttcaactggaggtgtttgccggcg
agctgaccgcgctgatcggcccgaccggcgccggcaaatcgtcggtgctcaaggccatttaccgcacctacctgc
ccagcagtgggcgcatcctttaccgggacgccaacggtgccatcaccgatctggcccaggccagcgaacaccgca
tgctggagctgcgcaagcaggacctgggtttcgtcacccaatttctgcactgtctaccgcgcaagtcggcggtcg
aggtagtggccgagccgctggtgcagcggggcagcccgcgcgaagctgctgccgagcgcgcgcgcgaactgctgg
ccctgctcaacgtgccggaacgcttgtgggcggtaccacccgccaccttctcgggcggcgagaaacagcgcgtca
acctggcacgcgggctgatcgccggcctcggctgctgttgcttgacgaacccacggccagcctagacccgtcca
ccaccgaccgcgtggtggagctgttgaagtccatcaaggccgaaggcgtggccatgctggccatcttccacgacc
ccgaacttgtccgacgcctggccgatcgcgtcgtaaccctcacgcccccggtgtctgcggcggcattgctggaga
cctgtgcctcatgaatcccatttgctgacccatgcccgcgtggtgttccccaccgaagtccgtgacaacgtggc
catcctgatcgaaggcgacaccatcacagcatcgacccggccagcagcgcaggtgccaccgagatcgacctgcgc
ggctcgcaccctgatgccaggtctgatcgacctgcactgcgacgcaatggagaaagaggtggagccgcggcccgg
cgtgcacttcccgctggagttcgcctgtgcccaggccgacaagcgcaatgcggcggccggcatcacgacggtgtt
tcatgccctgtcctttgccaaccacgagctgggcgtgcgcaacaacgccttcgccgccgagatcgcccgttcgat
tggcgactggcaggcccatgccctgatcgacaaccgggtgcatgtgcgttacgaggtgacggacgaaacggcgcc
gccggtgctgtcggcgctgctgcaggacggtcatgcgcacctcatgtctttcatggatcacagccccggtcaggg
tcagttccgcgatgtcgaggcgtaccgcgcctacctggccaagacctacaagaccgatgaggcgcagatcgacga
catcctggcgcgcaaagccggggccgcacagggcgccatgcggcgcatggagcagcttgcggaactggcccgtgc
gtgcggcgtgtccattgccagccacgacgacgacagcccgcagaaagtggcgaccgtcaaggccctgggcgctgt
ggtgtcggagtttccggtgaacctggagacggcacaggccgcccgtgcacaaggcctggccaccttgtttggcgc
tcccaacatcctgcgcggcaagtcccagtcgggcaacatgcgtgccctcgatgccgtgctggccggtgtcgccga
ctgcctgtgcggtgactactcgccagcggcgctgttgccgtcggtcatgcgcttgcccgatctggccggcatccc
cctggccgaggctgtggccctcgtcacgtgcaacccagctcgtgctgcaggtttgcacgaccgggggcgagatcgc
cgtgggcaagcgcgcagacctgattgcggtcaaaaccatgggcggactgccacaggccgagcgggtctggtcggg
cggtaaagcttcgctggtcgcgcatttgaccacgcctgagagggactggcacatgcgaactcgcctcatctacg
tggtcggcgcctcgggcagcggcaaggacacgctcatgggccatgcccgccagaagctggcgggtgatcccaggg
tgtgttttgcccatcgctacatcacccgacccgcaacggcaggcggcgaaaaccatgtggccttgaccacggagg
aattcaccgctcgccagaacggcaagctctttgccatgcactggtccagccacggcctgcattacggaatcggca
tcgagatcaaccagtggctgggcaaaggcatcacggtggtgatcaacggctcgcgggaatacctggacgaggccc
gccaacgttacccggagctgctgccggtgacgattgacgtggccaccaccgtgctgcgtgatcggctgctggccc
gtggccgcgaggatgccgaatccattgagcagcgcctgcaccgccatgaaacgttgcgcctgcagccgtgcccg
gtgtgctcatccagaacaacggacccgtcgaggtggccggcgaagcgctgatccggttgatcgcagaacacaccc
aaggagcgccagtatgcgtgtgagtttctgggcacgggcgctgcgggcggggttccgctctacggttgcacctg
ccgggcctgtgaacgcgcaaggaccgagccacacttcgtccgccgcccttgcagcgccctgattgaatccggagg
tacccgggtgctactggatgccgggctgatggaccttcacgaacggtttgcgccgggtagcctggacgcgattgt
tctcacgcactaccacccgaccacgtgcagggactctttcatctgcgctggggtaaggggacgcccatcacagt
ctatggcccaccagacagcgaaggctgcgccgatttgttcaagcaccctggtgtactggccttcgagacggtgca
caagttcgaggccttcacgtcggggcgctgcgcctgacgcccctgccgctgcttcactccaaacccacgctggg
ctatgccatcgagggcacccagggccaacgcttcgcctacctcacagacaccctgggtttgccgccgaagtcggc
caagttcctgcgcgcctggggcgactttgacatggccatcgactgttcctatccgccgcacccgacccgaaaaa
ccacaacgattgggacgaagcacatcggtgtgccatcgaatctggtgcccgcatcacctggctcacccatgccgg
tcatgcgctggacgactggatgatggaagagacgccgagcgtcgcaagtcatatccggctggcccgggacggcag
cacggccgacataccgtcccaaacgcaatgaacgcgccgctggcactggccctgtcggtggccatgcacgtcacc
tggaacctgatggcacggcatttgcccagggaatcgaacccgctgtggtgggtgttgctcgcccatctggtgctg
tttgcgccctggggttctgggagctggcgacaaccgtcgtttggtcactggagatgacgctgctactgatcgta
tcggccactgcgaatgtggtttatttctccggtctggccagggcctacgagcacgcaccggtcgcactggtctat
cctctggtgcgcagttcacctcttttcattgcgatctggggcacgctgttcttcggtcaaaatctcccgcccatt
gcctggctgggc

Figure 1 (continued)

attggcatcagcgtgctgggcttgctcgtcatggcatcgagtgctcaacaggggtcggatcgacgagcattccga
tgggccatgctggccatgttggcgacaagcgtttattccctgagtgacaaggcggccaccgaacacatcccaagc
ttcatggggctcgtgggttttctgtccgtcggctacctggcatcctggatcagcatgaccttgcgcatgcatcgg
cacacccgcagttgggtgccggcacagcgcattgatctcgcgtcgctggctcttggcggaacctgtatcggtctc
gcctacgccttggttatccacgccatgcgccagttgcctgcggcggaggtcgtgtcgtacaccaacgccggtatc
gtgctcgctgcagttctctccatttttttgttcaatgacaaagtcggatggcaaaagagaatcatggggtcgtg
atcatcacgagtggtttgggggtgcttgccatgaggtgagcgacacaataccaaccatcgcacaccagcattcca
acccggctcgcgacctgccggtgaagtaaaagcgacttccgatatgtcccaaatttcccgatacgtcgaggccgc
cgagcgtgacaacacgcgtcgaagctatgccgcagccattcgccatttcgaggtggagtggaaaggcttgctgcc
aacgaccgctgatgcaacctcccgttacctggctgaccacgcggccacgctggcgatcagcaccctccgtcagcg
gctcgccgcgctctcgcgctggcacatcgaccatggttttgcagacccgaccaaggcacccttggtgcgccaggt
tctcaaaggcattcgctccattcactcggttgcagaaaagcgggcacgcccccttgaaatcgatgtcgtccagca
gatcgatcaatggctgggggtggccatcggcaacgcagaacgcagcgatgaccgattggcgctgcttcgccacac
ccgcaaccgcagtttgctgctgctgggtttctggcggggatttcgatcggacgagttggtcaacctgcgggtgga
gaacgtggaagtctcgcctggcgaagggctgtcgtgctacctgagccgcagcaagggcgatcggcagatgctggg
ccgcgtatacaaatgtccggcgctgtcccgcctgtgtcctgtgacggctttcacggcatgggtcagtctggtcgg
cctgacccaaggcccggtgtttcgcaagatcgaccgctgggggcgaatcggtcaagaagggctgcatgccaacag
cctgatcccattgttgcgcagccttttggctgaggccggggtccccgcttccgaggcatacagcagccactccct
gcgtcgcggatttgccggttgggctcgcgccagcggttgggacatcaaggaactcatggagtacgtgggctggaa
ggatgtcaaatcggccatgcgttatctggatgcctccggcagcgcacttcaggcccggtttgaggcgggtctcgc
aacactggccccagcagatcgagcggatcggtcaccaccgccttcgatgcacgcgccggccgagcaaaccaaggg
aacaggcccagaggcccgtctgcctga Delftia acidoorans phosphodiesterase pdeA atgcacaagttcatccacatcacggacattcatcttgtcgagcagggtcgcgccctctacggccatgacccggc
aaacggttcgagcgctgcatcgacagcgtgatcgccgagcacgcggacgcagcgtcttgcgtgatcacgggcgac
ctcgcacatgtcgggcacccggacgcctaccgccagctgtcggagcaatgcgcgcggttgccaatgccggttcat
ctgattctcggcaaccacgacagccggaccaacttccgcgagcgcttcccacaggtgccggtggacagcaatggg
ttcgtccagtacgagcaggccatcgggaggttcaggggtctgtttctggataccaacgaaccgggaacgcattgc
ggcgtcttctgcgagcaacgggcaaactggctttcccagcgcttggcggaggatgattcaccggtgctcctgttc
atgcatcatccggcattccaccttggcatcccggtcatggatcgaatcggattggtcgacaacgaatggttgctg
acggcgttgaagggccacgagcaccgcgtcaagcacttgttcttcggccacattcatcgccccatctcgggcagc
tggcgcggcatcccgttctcgacattgcgcggaaccaaccaccaggtggcgctgcaccttcgggaatcggaagac
atcccgggaagcttcgagccaccacagtacgccgtcgtcctgctcgacgacgattcggtgatcgtgcacctgcat
gactttctcgatcgcagcgagagattctggctaggcgcgtag Enterobacter aerogenes updABDE gpdQ atgaataagcgctggctcccctggctgatactgtcgcctttccctgttgtttttactgctgtttacctggtttccg
cttggccgttcggtctatgacagcctgtttgatacccgcatggccagcgacggcgcacagtacgtcgggctggat
aacttcgcccgcctgtttgccgacggcgttttctggcaatcgctggtcaataatctgctctatatcctgctgacg
gtggtgcccggcgtgacgctcgctctgctgctggcggtggcgctgagcgagaatcaccgcgtcaaccgctggctg
cgcaccgcctttttcttcccgatgattatcccgatggttagcgccgccgcgctgtggctgtttattttttatgccc
ggcctcggcctgctcgatcactatctggcgaagctatttggccctcagaacaacaactggctggggcgcagcaac
agcgcgctgctggcgctggcgctgattggcgtgtggaaattcgctggctactacatgctgtttttcctcgccggg
ctgcagagcattccggcctcaacgcgggaagcggcgctgatggaaggggccagccgcacccaggtgtttttttaag
gtcacgctgccgctgctgcgcccgacgctgagctttgttatcaccaccgcgctgatttactccattacccagatt
gatcacgtcgcggtgatgacgcgcggcgggccggataacgccacgaccgtgctgctctattacatccagaatctc
gcctgggatacccacgacctcggcaaagcctccgccgccaccttcctgacgctggccgggctgtttgccttctcg
ctgattaacctgaaattgctggaaaaaggagcccactatgagcgctgaaatctcgccgctgatggtccgctcgcc
cgccgctgcgcgtccgctgtggttgcgcctgcgtcgctcacagccctttaccctgacggtaatcatgtgctgcct
ggcgctgctatgggtgagcccgtttatctggatgctggcgacctcgttcagcgccaccaccttcggcgaagatat
ggcctcattgctgccgcgcctgccgctgaccctcgataactt

Figure 1 (continued)

ccgcgacgcctgggacagcgccgactggctgagcctgtacgccaacacccttatctttaccttcggcactttcttt
cgtgcagctactcaccatcaccaccgccggctacgtcttcgcctgccacgaatttcgcggcaagaaaatgctatt
tctgctgtttctcgtccagctgatgatcatgccggtggtgatgatggtgccgaacatgctgaccctgaaaacctt
cggcctgctcaacactctgaccggcgtgatgatgccttactttacctcggcgttcggcgtgtttctgatgcgcca
ggcgttcctcgccatcccgaaagagctggaagaggcggcgctgatggagggatgccgctggtggcaggtgctatt
ccgcgtactgctgccgatgtcctggccgtcggtgctggccttcgccaccgtcagcattacctaccactggaacga
gtacctgtggccgctgatgatgctcaacgatcccgataagcaggtgctgacggtcgggctggtctctttcgccat
gggcgctgaatccggcggccagtggggcaccatcggcgccgggacgctgatggtctgcctgccgctgatgctggc
gttcatcctttttccagaaacagttcctgcgaagcttcggcttctccgggatcaaataaggagttattcatgctgt
tagcgcacatttccgatacccatttccgcagccgcggcgagaagctgtacggctttatcgacgtcaacgccgcca
atgctgatgtggtttctcaacttaacgcgctgcgcgaacgcccggatgcggtggtggtgagcggcgatatcgtca
actgcggccgtccggaggagtatcaggtcgcccgccagatcctcggcagcctgaactatccgctgtatctcatcc
ccggcaaccacgatgataaagcgctgtttctggagtacctgcagccgctgtgtccacagctcggtagcgatgcca
ataatatgcgctgtgcggttgacgacttcgctacccgcctgctgtttatcgactccagccgcgccggcacttcaa
aaggctggctgaccgacgagaccattagctggctggaagcgcagctgttcgagggcggcgacaaaccggcaacga
tctttatgcaccacccgccgctgccgctgggcaatgcgcagatggacccgattgcctgcgaaaacggccaccgtc
tgctggcgttggtagagcgtttcccgtcgctgacgcgcatcttttgcggtcataaccatagcctgaccatgaccc
agtatcgccaggcgctgatctccaccctccccggcaccgtccatcaggtgccttactgccacgaagacactcgcc
cgtattacgatctctcgcccggcttcgtgcctgatgcaccgccaggtcggcgagcaatgggtgagctaccagcact
cgctggcccactacgccgggccgtggctgtacgacgaaaacatcagttgtccaacggaagagcgctaaccgccat
gctcagtctgcaaaacatcagtaaacatttcgacggtaaaccggcgctcagcgcgctgtcgcttgatatccacga
aggtgaatttgtggtgctggtcggcccgtcgggctgcggtaaaagcaccctactgcgcctgcttgccgggttgga
tcaggtcagcgaaggcgaaatctggctgcatgatgagaacatcaccgacaccacgccgcgcgaacgcaattttgc
gatgatcttccagaactatgcgctgtttccacatctctctgtgcgcgacaacatcaccttcggcatgaaggtacg
caaggaagagaaaagcggctggcagccgcgggtagataaagtggcgcagatgctgcagctggaggcgctgctcga
tcgcaaaccggcgaagctctccggcggccaacggcagcgggtagcgatggcgcgggcgatcgtgcgtaatccgcg
gctgttcttaatggatgaaccgctgtccaacctcgacgctcgtctgcgcagcgaagtccgcgacagcattatgga
cctccaccagcagttaaaaaccagtaccgtctacgtcacccacgatcaaaccgaagccatgtcgatggccgaccg
catcgtggtgatgaacggcggccacgtgcagcaagtggggcggccagagtatctgtatgccaacccggccaatct
gttcgtggccagatttatcggttcaccggcaatgaatctgctatcgctccccctgcgttgacggcaacgttcagct
tggcgaacaacgccatccgctaccgccgcgccatcgcagccagacccgtgtctggctgggcattcgcccggaaca
tattaccgaccgcgtggagcacggccatctgcgcctgccgggcaccgtcctgcaacgagaactgatgggagccga
ttatctgctccacgtcagcaccccgatcggcaccctgcgctttagccgcccgccaccgtggcacggtgccggaaaa
aggcgaatcgctgatcctcggcttctcgcctgccgatgtgcatctttttcatgctgagacccagcataatttact
gatggagtgtaatcatgtttaacccccctcaccgccctgacggttgggctcagcctcgccctgagcggcacggcgc
tggcgaaagagaaaatagacttcatgttcccggccccggtagacggcaagctgacgatggagatgacacgcgtca
ttaaagcctttaacgagtcgcagcaggatgtcgaagtgcgcggcatcttcaccggcaactatgacaccaccaaga
tcaaagccgaatccgcgcagaaggccgggcaacccccggcgctggtgatcatgtccgccaacttcaccaccgatc
tggcgctgaaggatgagatcctgccgatggatgagctgtttaaatatggcgatcaaaaggccggcgatttttctgc
aaaaggaattctggcccgcgatgcataagaacgcccaggtgatgggcaccacctatgcgatccgttccataact
cgacaccgatcctctactacaacaagacgctgttagatcgagctgggatcgcgcaaccaccgcagacctgggccg
agctgctggccgatgccaaaaagctgaccgacgagagcaaaggccagtggggggatcatgctgccgtcgaccaacg
acgactacggcggctggatcttctcggcgctggtgcgcgccaacggcggtaaatatttcaatgaagactatccgg
gtgaggtttattacaactcgccgaccgctatcggcgctctgcgcttctggcaggatctgatctacaaagacaaag
tgatgccttccggggtactgaattcgaagcagatcagcgcttcattcttctccggcaaacttggcatggcgatgc
tcagcaccggcgcactgggctttatgcgcgagaacagtaaagatttgaactcggtgtcgccatgctaccagcca
aagagcagcgcgcggtgccaattggcggcgccagcctggtgagctttaaaggcatcaacgacgcgcagaagaaag
cggcctaccagttcctgacttatctggtgagcccgcaggtaaacggcgcgtggagccgctttaccggctacctct
cgcccgcgtaaggcttcttacgatactccggagatgaaagcttatctgcagcaggatccacgagcagcgatcgccc
ttgaacagctgaagtacgcgcatccgtggtactccacctgggagaccgtcgccgtgcgtaaggcgatggagaacc
agctggcggcagtggtcaacgatgccaaagtaacgccggaagccgcggtacaggcagcgcagaaggaagctgacg
cgctaatgaaaccttatgttgataagactgcgctgggagaagtgcagtag

Figure 1 (continued)

Flavobacterium opdA without periplasmic leader sequence atgtcgatcggcacaggcgatcggatcaataccgtgcgcggtcctatcacaatctctgaagcgggtttcacactg
actcacgagcacatctgcggcagctcggcaggattcttgcgtgcttggccagagttcttcggtagccgcaaagct
ctagcggaaaaggctgtgagaggattgcgccgcgccagagcggctggcgtgcgaacgattgtcgatgtgtcgact
ttcgatatcggtcgcgacgtcagtttattggccgaggtttcgcgggctgccgacgttcatatcgtggcggcgacc
ggcttgtggttcgacccgccactttcgatgcgattgaggagtgtagaggaactcacacagttcttcctgcgtgag
attcaatatggcatcgaagacaccggaattagggcgggcattatcaaggtcgcgaccacaggcaaggcgaccccc
tttcaggagttagtgttaaaggcggccgcccgggccagcttggccaccggtgttccggtaaccactcacacggca
gcaagtcagcgcgatggtgagcagcaggccgccatttttgagtccgaaggcttgagcccctcacgggtttgtatt
ggtcacagcgatgatactgacgatttgagctatctcaccgccctcgctgcgcgcggatacctcatcggtctagac
cacatcccgcacagtgcgattggtctagaagataatgcgagtgcatcagccctcctgggcatccgttcgtggcaa
acacgggctctcttgatcaaggcgctcatcgaccaaggctacatgaaacaaatcctcgtttcgaatgactggctg
ttcgggttttcgagctatgtcaccaacatcatggacgtgatggatcgcgtgaaccccgacgggatggccttcatt
ccactgagagtgatcccattcctacgagagaagggcgtcccacaggaaacgctggcaggcatcactgtgactaac
ccggcgcggttcttgtcaccgaccttgcgggcgtcatga Pseudomonas aeruginosa PAO1 phoA atgaccccaggttatcccctcgccctctctcttgccgtctccatggccgtgctcggcagcgccttgccggcccag
gcgcgccaggacgatccgtcactgttcaaccgccaggcccgtggcgaactcagcgagtacggcggcgcacggcgc
gtcgagcaggacctgacccaggccctgaagcagtcgctgtcgaagaagaaggcgaagaacgtgatcctgctgatc
ggcgacggcatgggcgactccgagatcaccgtggcgcgcaactacgcgcgcggcgcgggcggctacttcaagggt
atcgatgcgctgccgctgaccggtcagtacacccactactccctgcacaaggacagcggcctgccggactacgtg
accgattccgccgcctccgccaccgcctggtccaccggggtcaagtcgtacaacggcgcgatcggcgtggatatc
cacgaacagccgcaccgcaacctgctggagctggccaagctcaacggcaaggccaccggcaacgtctccaccgcc
gagctgcaggacgccacccccgccgccctgctcgcccacgtcaccgctcgcaagtgctacggtcccgaggccacc
agcaagcagtgcccgagcaatgccctggagaacggcggcgccggctcgatcaccgagcagtggctgaagacccgc
cctgacgtggttctcggcggcggcgccgcgaccttcgcggaaaccgccaaggctggccgctatgccggcaagacc
ctccgcgcccaggccgaagcccgcggctaccggatcgtcgagaacctcgacgagctgaaagccgtgcgccgcgcc
aaccagaagcagccgctgatcggcctgttcgcgccgggcaacatgccagtgcgctggctcggtccgaccgccacc
taccacggcaacctgaaccagccggcggtgagctgcgaggcgaacccgaagcgcaccgccgacatcccgaccctg
gcgcaaatgaccagcaaggccatcgagctgctgaaggacaatccgaacggcttcttcctgcaggtcgagggcgcg
tccatcgacaagcaggaccatgccgcgaatccgtgcggccagatcggcgagaccgtcgacctcgacgaagccgtg
cagaaggccctggcctttgccaaggccgatggcgagaccctggtgatcgtcaccgccgaccacgcccactccagc
cagatcatcccgccggaaaccgccgcgccggggctgacccaactgctcacgaccaaggacggcgcgccgctggcg
atcagctacggcaactccgaggaaagctcccaggagcacaccggcacccagttgcgcatcgccgcctacggcccg
caggccgccaatgtcaccggcctgaccgaccagaccgacctgttcttcaccatccgtcgcgcactgaacctgcgc
gactga Pseudomonas monteilii C11 hocA atgaaagaactaaaacctggaagtgggaagataaagagagaacaatgctgagaaaaatctctgttggagatata
ttttgcctcaccaaagacaacagcaactatcatttcggtaaaatcttgtcaaaaatgattgtaggccacgcagtc
gaaatattaaatatcactaaagacagcccatcaatcacccagcaagaacttgaacaatcagccttagcaggccga
ccgctactgctagatagttacgctttattcgacaagaaaattgacaaaggtggcgactggagaataattggccat
caagagatatcatcaccagaatcctatcgaaactactacttcctgttcctgtacggaacacacaacaactggaaa
aaagtcaacatcctcaatgaggaagttgaaatatcaaatacagaggccctaacgctcccettgcttaaagctctt
agcaatcacagattctgggaaacaataaacgaagaactaaagctaaactggtaa

Figure 1 (continued)

Rhodococcus dszD ttgtctgacaagccgaatgccgtttccagccacaccaccccccgacgtccccgaagtagcggcgacgcccgagttg
tccaccggcatctgcgccggtgactaccgcgctgcgcttcgccgccaccccgccggtgtcaccgtcgtgaccctc
gattcgggtaccggcccggtgggtttcaccgccacctcgttctcgtccgtctccctcgagccgccgctcgtctcg
ttcaacatcgcggagacgtcgtcgagcatcaatgcactcaaggcagccgagtccttggtgatccaccttctcggc
gaacatcagcagcatctggcccagcgctttgcgcgtagtgccgatcagcgttttgcagacgagtcactgtgggca
gtgctcgacaccggggaaccggtgctgcacggcacccccagctggatgcgcgtcaaggtcgaccagctgatccct
gtcggcgaccacacgctggtcatcggactcgtcacgcgggttcacgccgaagaagacgacgaatccgctgccgcg
ccgctgctctaccacgagggcaagtactaccgcccgactccgttaggtcaatag Rhodococcus dszABC atgactcaacaacgacaaatgcatctggccggtttcttctcggccggcaatgtgactcatgcacatggggcgtgg
cggcacacggacgcgtcgaatgactttctgtcggggaagtactaccaacacatcgcccgtactctggagcgcggc
aagttcgatctgttgtttctgcctgacgggttggccgtcgaggacagctacggggacaacctggacaccggtgtc
ggcctgggcgggcagggtgcagtcgccttggagccggccagtgtggtcgcaaccatggccgcggtgaccgagcac
ctgggtcttggggcaaccatttcggcgacctactatccccgtatcacgttgctcgggtgttcgcgacgctcgat
cagttgtcaggggggtcgggtgtcctggaacgtcgtcacctcgctcaacgacgctgaagcgcgcaacttcggcatt
aatcagcatctggaacacgacgcccgctatgaccgcgccgatgagttcttggaagcggtcaagaaactctggaac
agctgggacgaggacgccctcgtgctggacaaggcggccggcgtgttcgccgatcccgcgaaggtgcactacgtc
gatcaccacggggagtggctgaatgtgcgcggacctctgcaggtaccgcgttcacctcagggtgagccggtgatc
ctgcaggccggcctgtcgccccggggtcggcgcttcgccgggaagtgggccgaggccgtcttcagtcttgcaccc
aacctcgaggtgatgcaggccacctaccagggcatcaaagccgaggtcgacgctgcggggcgcgatcccgatcag
acgaaaatcttcaccgccgtgatgccggtactcggcgaaagccaggcggtggcacaggaacgactggaatatctc
aacagtctggtccatccggaagtgggactgtcgacgctatccagtcacaccggcatcaacctggcggcgtaccct
ctcgacactccgatcaaggacatcctgcgggatctgcaggatcggaatgtcccgacgcaactgcacatgttcgcc
gccgcaacgcacagcgaagagctcacgctggcggaaatgggtcggcgctatggaaccaacgtggggttcgttcct
cagtgggccggtaccggggagcagatcgctgacgagctgatccgccacttcgagggcggcgccgcggatggtttc
atcatctctccggccttcctgccgggctcctacgacgagttcgtcgaccaggtggttccggttctgcaggatcgc
ggctacttccgcaccgagtaccagggcaacactctgcgcgaccacttgggtctgcgcgtaccacaactgcaagga
caaccttcatgacaagccgcgtcgaccccgcaaaccccggttcagaactcgattccgccatccgcgacacactga
cctacagcaactgcccggtacccaacgctctgctcacggcatcggaatcgggcttcctcgacgccgccggcatcg
aactcgacgtcctcagcggccagcagggcacggttcatttcacctacgaccagcctgcctacacccgttttgggg
gtgagatcccgccactgctcagcgaggggttgcgggcacctgggcgcacgcgtctactcggcatcaccccgctct
tggggcgccagggcttctttgtccgcgacgacagcccgatcacagcggccgccgaccttgccggacgtcgaatcg
gcgtctcggcctcggcaattcgcatcctgcgcggccagctgggcgactacctcgagttggatccctggcggcaaa
cgctggtagcgctgggctcgtgggaggcgcgcgccttgttgcacacccttgagcacggtgaactgggtgtggacg
acgtcgagctggtgccgatcagcagtcctggtgtcgatgttcccgctgagcagctcgaagaatcggcgaccgtca
agggtgcggacctctttcccgatgtcgcccgcggtcaggccgcggtgttggccagcggagacgttgacgccctgt
acagttggctgccctgggccggggagttgcaagccaccggggcccgcccagtggtggatctcggcctcgatgagc
gcaatgcctacgccagtgtgtggacggtcagcagcgggctggttcgccagcgacctggccttgttcaacgactgg
tcgacgcggccgtcgacgccgggctgtgggcacgcgatcattccgacgcggtgaccagcctgcacgccgcgaacc
tgggcgtatcgaccggagcagtaggccagggcttcggcgccgacttccagcagcgtctggttccacgcctggatc
acgacgccctcgccctcctggagcgcacacagcaattcctgctcaccaacaacttgctgcaggaacccgtcgccc
tcgatcagtgggcggctccggaatttctgaacaacagcctcaatcgccaccgataggaacatccgcatgacactg
tcacctgaaaagcagcacgttcgaccacgcgacgccgccgacaacgatcccgtcgcggttgcccgtgggctagcc
gaaaagtggcgagccaccgccgtcgagcgtgatcgcgccggggggttcggcaacagccgagcgcgaagacctgcgc
gcgagcgcgctgctgtcgctcctcgtcccgcgcgaatacggcggctggggcgcagactggcccaccgccatcgag
gtcgtccgcgaaatcgcggcagccgatggatctttgggacacctgttcggataccacctcaccaacgccccgatg
atcgaactgatcggctcgcaggaacaagaagaacacctgtacacccagatcgcgcagaacaactggtggaccgga
aatgcctccagcgagaacaacagccacgtgctggactggaaggtcagcgccaccccgaccgaagacggcggctac
gtgctcaatggcacgaagcacttctgcagcggcgccaaggggtcggacctgctgttcgtgttcggcgtcgtccag
gatgattctccgcagcagggtgcgatcattgctgccgctatcccgacatcgcgggctggcgttacgcccaacgac
gactgggccgccatcggcatgcggcagaccgacagcggttccacg

Figure 1 (continued)

```
gacttccacaacgtcaaggtcgagcctgacgaagtgctgggcgcgcccaacgccttcgttctcgccttcatacaa
tccgagcgcggcagcctcttccggcccatagcgcaattgatcttcgccaacgtctatctggggatcgcgcacggc
gcactcgatgccgcccagggagtacacccgtacccaggcgaggccctggacaccggccggtattcaacaggcaacc
gaggatccctacaccatccgctcctacggtgagttcaccatcgcattgcagggagctgacgccgccgcccgtgaa
gcggcccacctgctgcagacggtgtgggacaagggcgacgcgctcacccccgaggaccgcggcgaactgatggtg
aaggtctcgggagtcaaagcgttggccaccaacgccgccctcaacatcagcagcggcgtcttcgaggtgatcggc
gcgcgcggaacacatcccaggtacggtttcgaccgcttctggcgcaacgtgcgcacccactccctgcacgacccg
gtgtcctacaagatcgccgacgtcggcaagcacaccttgaacggtcaatacccgattcccggcttcacctcctga
```

Figure 2

| Organism | Potential Applications |
|---|---|
| *Escherichia coli* | Biotech |
| *Saccharomyces cerevisiae* | Ethanol, food, biotech |
| *Yarrowia lipolytica* | Citrate, lipase, lipids, polyols |
| *Kluyveromyces marxianus* | biotech |
| *Bacillus subtilis* | industrial enzymes |
| *Hansenula polymorpha* | enzymes, SCP |
| *Aspegillus niger* | Citrate, amylase, oxalate |
| *Corynebacterium glutamicum* | Amino acids, nucleotides |
| *Synechococcus elongatus* | Biofuels, lipids |
| *Chlamydomonas reinhardtii* | Biofuels, model organism |

Figure 3

| Organism | Potential Applications |
|---|---|
| *Mammalian/CHO* | pharma |
| *Kluyveromyes lactis* | lactic acid |
| *Xanthomonas campestris* | Xanthan gum, plant pathogen |
| *Pichia pastoris* | enzymes |
| *Candida utilis* | animal feed |
| *Aspergillus orzyae* | enzymes, malic acid |
| *Bacillus stearothermophilus* | industrial enzymes |
| *Bacillus licheniforms* | industrial enzymes |
| *Lactococcus lactis* | Dairy, food |
| *Streptococcus lactis* | Dairy, food |
| *Trichoderma reesei* | cellulases, xylanases |
| *Clostridium acetobutylicum* | butanol, 1,3 PD, solvents and acids |
| *Clostridium thermocellum* | ethanol, biofuels |
| *Streptomyces* | antibiotics, antifungals, protein expression |
| *Acetobacter* | acetic acid, specality sugars |
| *Micrococcus lysodeikticus* | catalyase, dairy |
| *Pichia guilliermondii* | citric acid |
| *Arxula adeninivorans* | enzymes, possibly biofuels |
| *Acinetobacter calcoaceticus* | |
| *Paracoccus denitrificans* | |
| *Pseudomonas putida* | chemicals, solvents |
| *Bacillus methanolicus* | methanol utilization |
| *Alcaligenes eutropha* | PHA/PHB, chemicals |
| *Thermoanaerobacter/Thermoanaerobacterium spp.* | biofuels |
| *Pichia stipitis* | |
| *Rhodosporidium spp* | |
| *Rhodotorula spp.* | |
| *Schizosaccharomyces pombe* | |
| *Penicillium chrysogenum* | |
| *Aspergillus terreus* | itaconic acid |
| *Aspergillus nidulans* | |
| *Rhizopus spp.* | |
| *Nannochloropsis spp.* | |
| *Tetraselmis spp.* | |
| *Pavlova spp.* | |
| *Isochrysis spp.* | |
| *Aurantiochytrium spp* | |

Figure 4

| | |
|---|---|
| Hypophosphorous acid | $H_3PO_2$ |
| Phosphorous acid (phosphite) | $H_3PO_3$ |
| Diethyl phosphate | $C_4H_{11}O_4P$ |
| Triethyl phosphate | $C_6H_{15}O_4P$ |
| Trimethyl phosphate | $(CH_3)_3PO_4$ |
| Dimethyl phosphate (DMP) | $C_2H_7O_4P$ |
| Diethyl phosphite | $C_4H_{11}O_3P$ |
| Triethyl phosphite | $C_6H_{15}O_3P$ |
| Trimethyl phosphite | $C_3H_9O_3P$ |
| Dimethyl phosphite | $C_2H_7O_3P$ |
| Glyphosate (round-up) | $C_3H_8NO_5P$ |
| O,O,O-Triethyl Phosphorothioate | $C_6H_{15}O_3PS$ |
| Etidronic acid | $C_2H_8O_7P_2$ |
| Disodium methylene diphosphonate | $CH_4Na_2O_6P_2$ |
| Medronic acid | $CH_6O_6P_2$ |
| Clodronic acid | $CH_4Cl_2O_6P_2$ |
| Tiludronic acid | $C_7H_9ClO_6P_2S$ |
| Zoledronic acid | $C_5H_{10}N_2O_7P_2$ |
| Oxidronic Acid | $CH_6O_7P_2$ |

Figure 5

| | |
|---|---|
| Dimethylsulfoxide | $C_2H_6OS$ |
| Dibenzothiophene | $C_{12}H_8S$ |
| Ethanethiol | $C_2H_6S$ |
| Dimercaptosuccinic acid | $C_4H_6O_4S_2$ |
| Thioacetic acid | $C_2H_4OS$ |
| tert-Butylthiol | $C_4H_{10}S$ |
| Thiourea | $CH_4N_2S$ |
| Sodium thiocyanate | NaSCN |
| Thioacetamide | $C_2H_5NS$ |
| Isothiazole | $C_3H_3NS$ |
| Benzisothiazolinone | $C_7H_5NOS$ |
| Isothiazolinone | $C_3H_3NOS$ |
| Methanesulfonic acid | $CH_4O_3S$ |
| Thioglycerol | $C_3H_8O_2S$ |
| Potassium metabisulfite | $K_2O_5S_2$ |
| Acesulfame potassium | $C_4H_4KNO_4S$ |
| Benzenesulfonic acid | $C_6H_5SO_3H$ |
| Sodium cyclamate | $C_6H_{12}NNaO_3S$ |
| Saccharin | $C_7H_5NO_3S$ |
| Dioctyl sodium sulfosuccinate | $C_{20}H_{37}NaO_7S$ |
| 2,4-Dithiapentane | $C_3H_8S_2$ |
| Methylisothiazolinone | $C_4H_5NOS$ |
| Methylchloroisothiazolinone | $C_4H_4ClNOS$ |
| Sulfolane | $C_4H_8O_2S$ |

Figure 9

```
LOCUS       pNC273                  8184 bp ds-DNA     circular     22-NOV-2013
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    1448..1471
                     /label=2u ori
                     /ApEinfo_fwdcolor=$8080ff
                     /ApEinfo_revcolor=$8080ff
                     /ApEinfo_graphicformat=arrow_data {{0 1 2 0 0 -1} {} 0}
                     width 5 offset 0
     misc_feature    1..1447
                     /label=2u ori(1)
                     /ApEinfo_label=2u ori
                     /ApEinfo_fwdcolor=$8080ff
                     /ApEinfo_revcolor=$8080ff
                     /ApEinfo_graphicformat=arrow_data {{0 1 2 0 0 -1} {} 0}
                     width 5 offset 0
     rep_origin      complement(5412..6000)
                     /note="pMB1 origin of replication (counter-clockwise)
                     (RNAII -35 to RNA/DNA switch point)"
                     /label=pMB1 ori
                     /ApEinfo_fwdcolor=$ff0000
                     /ApEinfo_revcolor=$ff0000
                     /ApEinfo_graphicformat=arrow_data {{0 1 2 0 0 -1} {} 0}
                     width 5 offset 0
     misc_feature    3554..4084
                     /label=YlTEF1p(PR3)
                     /ApEinfo_fwdcolor=cyan
                     /ApEinfo_revcolor=green
                     /ApEinfo_graphicformat=arrow_data {{0 1 2 0 0 -1} {} 0}
                     width 5 offset 0
     misc_feature    5096..5395
                     /label=YlCYC1t(TER1)
                     /ApEinfo_fwdcolor=$00ffff
                     /ApEinfo_revcolor=green
                     /ApEinfo_graphicformat=arrow_data {{0 1 2 0 0 -1} {} 0}
                     width 5 offset 0
     gene            4085..5095
                     /gene="ptxABCDE operon"
                     /note="phosphite oxidation operon"
                     /label=ptxABCDE operon
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     misc_feature    1488..2309
                     /label=ScFBA1p
                     /ApEinfo_fwdcolor=$c70cdc
                     /ApEinfo_revcolor=$c70cdc
                     /ApEinfo_graphicformat=arrow_data {{0 1 2 0 0 -1} {} 0}
                     width 5 offset 0
```

Figure 9 (continued)

```
misc_feature    complement(6171..7121)
                /label=AmpR
                /ApEinfo_fwdcolor=$ff00ff
                /ApEinfo_revcolor=$ff00ff
                /ApEinfo_graphicformat=arrow_data {{0 1 2 0 0 -1} {} 0}
                width 5 offset 0
misc_feature    complement(7138..8175)
                /label=Sc URA3
                /ApEinfo_fwdcolor=cyan
                /ApEinfo_revcolor=$00ff00
                /ApEinfo_graphicformat=arrow_data {{0 1 2 0 0 -1} {} 0}
                width 5 offset 0
misc_feature    3349..3553
                /label=ScFBAlt
                /ApEinfo_fwdcolor=$eb74f8
                /ApEinfo_revcolor=$eb74f8
                /ApEinfo_graphicformat=arrow_data {{0 1 2 0 0 -1} {} 0}
                width 5 offset 0
CDS             2310..3335
                /label=hygR (NG4)
                /ApEinfo_fwdcolor=$00d700
                /ApEinfo_revcolor=$00a200
                /ApEinfo_graphicformat=arrow_data {{0 1 2 0 0 -1} {} 0}
                width 5 offset 0
misc_feature    1480..1487
                /label=PmeI
                /ApEinfo_fwdcolor=$ff8040
                /ApEinfo_revcolor=green
                /ApEinfo_graphicformat=arrow_data {{0 1 2 0 0 -1} {} 0}
                width 5 offset 0
misc_feature    5396..5403
                /label=PmeI(1)
                /ApEinfo_label=PmeI
                /ApEinfo_fwdcolor=$ff8040
                /ApEinfo_revcolor=green
                /ApEinfo_graphicformat=arrow_data {{0 1 2 0 0 -1} {} 0}
                width 5 offset 0
gene            5089..5095
                /gene="ptxE"
                /label=ptxE
                /ApEinfo_fwdcolor=pink
                /ApEinfo_revcolor=pink
                /ApEinfo_graphicformat=arrow_data {{0 1 2 0 0 -1} {} 0}
                width 5 offset 0
misc_feature    3341..3348
                /label=AscI
                /ApEinfo_fwdcolor=$009d9d
                /ApEinfo_revcolor=$00b9b9
                /ApEinfo_graphicformat=arrow_data {{0 1 2 0 0 -1} {} 0}
                width 5 offset 0
CDS             5089..5095
                /gene="ptxE"
                /note="putative transcriptional regulator of ptx operon;
                similar to lysR family of transcriptional regulators"
                /codon_start=1
                /transl_table=11
                /product="PtxE"
                /protein_id="AAC71710.1"
```

Figure 9 (continued)

```
                     /db_xref="GI:3127081"
                     /translation="MLNPVWLKSLVAIVQTGSFQSAARALGLAQPTVSQHLQKLEEQV
                     GVTLVQRSRSGCQPTTKALAFMPHATALLDMHARALEALSGNREKVGASSNIGTYLLQ
                     PFVRNYLTTANERGEVDLRIAANPDVADQLLAGQLDAAIMEWWLPHPDFEYRLWRVEP
                     LVLIVSPDHALAEAGCIERDRLVDLPMLGGEPGSGT"
                     /label=PtxE
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     misc_feature    5404..5411
                     /label=AscI(1)
                     /ApEinfo_label=AscI
                     /ApEinfo_fwdcolor=#007d7d
                     /ApEinfo_revcolor=green
                     /ApEinfo_graphicformat=arrow_data {{0 1 2 0 0 -1} {} 0}
                     width 5 offset 0
     gene            4085..5095
                     /gene="ptxD"
                     /label=ptxD
                     /ApEinfo_fwdcolor=#00e800
                     /ApEinfo_revcolor=#00e800
                     /ApEinfo_graphicformat=arrow_data {{0 1 2 0 0 -1} {} 0}
                     width 5 offset 0
     misc_feature    1472..1479
                     /label=PacI
                     /ApEinfo_fwdcolor=#ffff00
                     /ApEinfo_revcolor=green
                     /ApEinfo_graphicformat=arrow_data {{0 1 2 0 0 -1} {} 0}
                     width 5 offset 0
ORIGIN
        1 TTATCGATGA TAAGCTGTCA AAGATGAGAA TTAATTCCAC GGACTATAGA CTATACTAGA
       61 TACTCCGTCT ACTGTACGAT ACACTTCCGC TCAGGTCCTT GTCCTTTAAC GAGGCCTTAC
      121 CACTCTTTTG TTACTCTATT GATCCAGCTC AGCAAAGGCA GTGTGATCTA AGATTCTATC
      181 TTCGCGATGT AGTAAAACTA GCTAGACCGA GAAAGAGACT AGAAATGCAA AAGGCACTTC
      241 TACAATGGCT GCCATCATTA TTATCCGATG TGACGCTGCA GCTTCTCAAT GATATTCGAA
      301 TACGCTTTGA GGAGATACAG CCTAATATCC GACAAACTGT TTTACAGATT TACGATCGTA
      361 CTTGTTACCC ATCATTGAAT TTTGAACATC CGAACCTGGG AGTTTTCCCT GAAACAGATA
      421 GTATATTTGA ACCTGTATAA TAATATATAG TCTAGCGCTT TACGGAAGAC AATGTATGTA
      481 TTTCGGTTCC TGGAGAAACT ATTGCATCTA TTGCATAGGT AATCTTGCAC GTCGCATCCC
      541 CGGTTCATTT TCTGCGTTTC CATCTTGCAC TTCAATAGCA TATCTTTGTT AACGAAGCAT
      601 CTGTGCTTCA TTTTGTAGAA CAAAAATGCA ACGCGAGAGC GCTAATTTTT CAAACAAAGA
      661 ATCTGAGCTG CATTTTTACA GAACAGAAAT GCAACGCGAA AGCGCTATTT TACCAACGAA
      721 GAATCTGTGC TTCATTTTTG TAAAACAAAA ATGCAACGCG ACGAGAGCGC TAATTTTTCA
      781 AACAAAGAAT CTGAGCTGCA TTTTTACAGA ACAGAAATGC AACGCGAGAG CGCTATTTTA
      841 CCAACAAAGA ATCTATACTT CTTTTTTGTT CTACAAAAAT GCATCCCGAG AGCGCTATTT
      901 TTCTAACAAA GCATCTTAGA TTACTTTTTT TCTCCTTTGT GCGCTCTATA ATGCAGTCTC
      961 TTGATAACTT TTTGCACTGT AGGTCCGTTA AGGTTAGAAG AAGGCTACTT TGGTGTCTAT
     1021 TTTCTCTTCC ATAAAAAAAG CCTGACTCCA CTTCCCGCGT TTACTGATTA CTAGCGAAGC
     1081 TGCGGGTGCA TTTTTTCAAG ATAAAGGCAT CCCCGATTAT ATTCTATACC GATGTGGATT
     1141 GCGCATACTT TGTGAACAGA AAGTGATAGC GTTGATGATT CTTCATTGGT CAGAAAATTA
     1201 TGAACGGTTT CTTCTATTTT GTCTCTATAT ACTACGTATA GGAAATGTTT ACATTTTCGT
     1261 ATTGTTTTCG ATTCACTCTA TGAATAGTTC TTACTACAAT TTTTTTGTCT AAAGAGTAAT
     1321 ACTAGAGATA AACATAAAAA ATGTAGAGGT CGAGTTTAGA TGCAAGTTCA AGGAGCGAAA
     1381 GGTGGATGGC TAGGTTATAT AGGGATATAG CACAGAGATA TATAGCAAAG AGATACTTTT
     1441 GAGCAATGTT TGTGGAAGCG GTATTCGCAA Tttaattaag tttaaacGAT CCAACTGGCA
     1501 CCGCTGGCTT GAACAACAAT ACCAGCCTTC CAACTTCTGT AAATAACGGC GGTACGCCAG
     1561 TGCCACCAGT ACCGTTACCT TTCGGTATAC CTCCTTTCCC CATGTTTCCA ATGCCCTTCA
```

Figure 9 (continued)

```
1621 TGCCTCCAAC GGCTACTATC ACAAATCCTC ATCAAGCTGA CGGAAGCCCT AAGAAATGAA
1681 TAACAATACT GACAGTACTA AATAATTGCC TACTTGGCTT CACATACGTT GCATACGTCG
1741 ATATAGATAA TAATGATAAT GACAGCAGGA TTATCGTAAT ACGTAATAGT TGAAAATCTC
1801 AAAAATGTGT GGGTCATTAC GTAAATAATG ATAGGAATGG GATTCTTCTA TTTTTCCTTT
1861 TTCCATTCTA GCAGCCGTCG GGAAAACGTG GCATCCTCTC TTTCGGGCTC AATTGGAGTC
1921 ACGCTGCCGT GAGCATCCTC TCTTTCCATA TCTAACAACT GAGCACGTAA CCAATGGAAA
1981 AGCATGAGCT TAGCGTTGCT CCAAAAAAGT ATTGGATGGT TAATACCATT TGTCTGTTCT
2041 CTTCTGACTT TGACTCCTCA AAAAAAAAAA ATCTACAATC AACAGATCGC TTCAATTACG
2101 CCCTCACAAA AACTTTTTTC CTTCTTCTTC GCCCACGTTA AATTTTATCC CTCATGTTGT
2161 CTAACGGATT TCTGCACTTG ATTTATTATA AAAAGACAAA GACATAATAC TTCTCTATCA
2221 ATTTCAGTTA TTGTTCTTCC TTGCGTTATT CTTCTGTTCT TCTTTTTCTT TTGTcatata
2281 taaccataac caagtaatac atattcaaaA TGAAGAAGCC CGAGCTGACC GCTACCTCTG
2341 TTGAGAAGTT CCTGATTGAG AAGTTTGATT CCGTTTCCGA CCTGATGCAG CTGTCCGAGG
2401 GCGAGGAGTC TCGAGCCTTC TCCTTTGACG TGGGCGGACG AGGTTACGTT CTGCGAGTGA
2461 ACTCGTGTGC CGACGGCTTC TACAAGGATC GATACGTCTA CCGACACTTT GCTTCTGCCG
2521 CTCTGCCCAT CCCTGAGGTT CTCGACATTG GCGAGTTCTC TGAGTCCCTC ACCTACTGCA
2581 TCTCTCGACG AGCTCAGGGA GTCACCCTGC AGGACCTCCC TGAGACTGAG CTGCCTGCTG
2641 TCCTCCAGCC TGTTGCTGAG GCCATGGACG CTATCGCTGC TGCTGATCTG TCCCAGACCT
2701 CGGGTTTCGG CCCCTTTGGA CCTCAGGGAA TTGGACAGTA CACCACTTGG CGAGACTTCA
2761 TCTGTGCTAT TGCCGATCCT CACGTCTACC ATTGGCAGAC CGTTATGGAC GATACTGTGT
2821 CGGCTTCTGT CGCTCAGGCT CTGGACGAGC TGATGCTCTG GGCCGAGGAT TGCCCCGAGG
2881 TTCGACACCT GGTGCATGCT GACTTCGGTT CCAACAACGT TCTCACCGAC AACGGCCGAA
2941 TCACTGCCGT GATTGACTGG TCCGAGGCTA TGTTTGGCGA CTCGCAGTAC GAGGTGGCCA
3001 ACATCTTCTT TTGGCGACCC TGGCTGGCTT GTATGGAGCA GCAGACCCGA TACTTCGAGC
3061 GACGACATCC TGAGCTCGCT GGATCCCCTC GACTGCGAGC TTACATGCTC CGAATTGGTC
3121 TGGACCAGCT CTACCAGTCG CTGGTGGATG GCAACTTTGA CGATGCTGCC TGGGCTCAGG
3181 GACGATGTGA CGCCATCGTG CGATCTGGCG CTGGAACCGT CGGACGAACT CAGATTGCCC
3241 GACGATCCGC TGCTGTCTGG ACCGACGGAT GCGTGGAGGT CCTGGCTGAT TCGGGTAACC
3301 GACGACCCTC TACTCGACCT CGAGCTAAGG AGTAAtaaac ggcgcgccgt taattcaaat
3361 taattgatat AGTTTTTTAA TGAGTATTGA ATCTGTTTAG AAATAATGGA ATATTATTTT
3421 TATTTATTTA TTTATATTAT TGGTCGGCTC TTTTCTTCTG AAGGTCAATG ACAAAATGAT
3481 ATGAAGGAAA TAATGATTTC TAAAATTTTA CAACGTAAGA TATTTTTACA AAAGCCTAGC
3541 TCATCTTTTG TCAAGAGACC GGGTTGGCGG CGCATTTGTG TCCCAAAAAA CAGCCCCAAT
3601 TGCCCCAATT GACCCCAAAT TGACCCAGTA GCGGGCCCAA CCCCGGCGAG AGCCCCCTTC
3661 TCCCCACATA TCAAACCTCC CCCGGTTCCC ACACTTGCCG TTAAGGGCGT AGGGTACTGC
3721 AGTCTGGAAT CTACGCTTGT TCAGACTTTG TACTAGTTTC TTTGTCTGGC CATCCGGGTA
3781 ACCCATGCCG GACGCAAAAT AGACTACTGA AAATTTTTTT GCTTTGTGGT TGGGACTTTA
3841 GCCAAGGGTA TAAAAGACCA CCGTCCCCGA ATTACCTTTC CTCTTCTTTT CTCTCTCTCC
3901 TTGTCAACTC ACACCCGAAA TCGTTAAGCA TTTCCTTCTG AGTATAAGAA TCATTCAAAA
3961 TGgtgagttt cagaggcagc agcaattgcc acgggctttg agcacacggc cgggtgtggt
4021 cccattccca tcgacacaag acgccacgtc atccgaccag cacttttgc agtactaacc
4081 gcagATGCTG CCGAAACTCG TTATAACTca ccgagtacac gatgagatcc tgcaactggt
4141 ggcgccacat tgcgagctga tgaccaacca gaccgacagc acgctgacgc gcgaggaaat
4201 tctgcgccgc tgtcgcgatg ctcaggcgat gatggcgttc atgcccgatc gggtcgatgc
4261 agactttctt caagcctgcc ctgagctgcg tgtagtcggc tgcgcgctca agggcttcga
4321 caatttcgat gtggacgcct gtactgcccg cgggtctgg ctgaccttcg tgcctgatct
4381 gttgacggtc ccgactgccg agctggcgat cggactggcg gtggggctgg ggcggcatct
4441 gcgggcagca gatgcgttcg tccgctctgg cgagttccag ggctggcaac cacagttcta
4501 cggcacgggg ctggataacg ctacggtcgg catccttggc atgggcgcca tcggactggc
4561 catggctgat cgcttgcagg gatgggggc gaccctgcag taccacgagg cgaaggctct
4621 ggatacacaa accgagcaac ggctcggcct gcgccaggtg gcgtgcagcg aactcttcgc
4681 cagctcggac ttcatcctgc tggcgcttcc cttgaatgcc gatacccagc atctggtcaa
4741 cgccgagctg cttgccctcg tacggccggg cgctctgctt gtaaacccct gtcgtggttc
4801 ggtagtggat gaagccgccg tgctcgcggc gcttgagcga ggccagctcg gcgggtatgc
4861 ggcggatgta ttcgaaatgg aagactgggc tcgcgcggac cggccgcggc tgatcgatcc
4921 tgcgctgctc gcgcatccga atacgctgtt cactccgcac atagggtcgg cagtgcgcgc
4981 ggtgcgcctg gagattgaac gttgtgcagc gcagaacatc atccaggtat tggcaggtgc
5041 gcgcccaatc aacgctgcga accgtctgcc cAAGGCCGAG CCTGCCGCAT GTTGAGCGTC
```

Figure 9 (continued)

```
5101 TACAACTGGA CCCTTAGCCT GTATATATCA ATTGATTATT TAAAGATTTG GTCGGTAGGC
5161 GGTTCGTATT GTACAATGGG ATCTGTTACT GAGGTGGATC TACCCAACTT GCGAGATTCA
5221 ATTGCGAGAT TCAATCGCGA GATTCAATTG CGAGAATCAG TTGCGACTTG TTCTAACACT
5281 CAGCTTCTAC GAGCGCTTGT ATTAGGACGA GTGATACTCC GTGGGGCGAC GGCTTCTCTT
5341 GCGTCTTCTG TTGTATTCTT TCTTACACTA TCGTCCATCT CCAACCACCT CGTACgttta
5401 aacggcgcgc ctttccatag gctccgcccc cctgacgagc atcacaaaaa tcgacgctca
5461 agtcagaggt ggcgaaaccc gacaggacta taaagatacc aggcgtttcc ccctggaagc
5521 tccctcgtgc gctctcctgt tccgaccctg ccgcttaccg gatacctgtc cgcctttctc
5581 ccttcgggaa gcgtggcgct ttctcatagc tcacgctgta ggtatctcag ttcggtgtag
5641 gtcgttcgct ccaagctggg ctgtgtgcac gaaccccccg ttcagcccga ccgctgcgcc
5701 ttatccggta actatcgtct tgagtccaac ccggtaagac acgacttatc gccactggca
5761 gcagccactg gtaacaggat tagcagagcg aggtatgtag gcggtgctac agagttcttg
5821 aagtggtggc ctaactacgg ctacactaga agaacagtat ttggtatctg cgctctgctg
5881 aagccagtta ccttcggaaa aagagttggt agctcttgat ccggcaaaca aaccaccgct
5941 ggtagcggtg gtttttttgt ttgcaagcag cagattacgc gcagaaaaaa aggatctcaa
6001 gaagatcctt tgatcttttc tacggggtct gacgctcagt ggaacgaaaa ctcacgttaa
6061 gggattttgg tcatgagatt atcaaaaagg atcttcacct agatcctttt aaattaaaaa
6121 tgaagtttta aatcaatcta aagtatatat gagtaaactt ggtctgacag ttaccaatgc
6181 ttaatcagtg aggcacctat ctcagcgatc tgtctatttc gttcatccat agttgcctga
6241 ctccccgtcg tgtagataac tacgatacgg gagggcttac catctggccc cagtgctgca
6301 atgataccgc gagacccacg ctcaccggct ccagatttat cagcaataaa ccagccagcc
6361 ggaagggccg agcgcagaag tggtcctgca actttatccg cctccatcca gtctattaat
6421 tgttgccggg aagctagagt aagtagttcg ccagttaata gtttgcgcaa cgttgttgcc
6481 attgctacag gcatcgtggt gtcacgctcg tcgtttggta tggcttcatt cagctccggt
6541 tcccaacgat caaggcgagt tacatgatcc cccatgttgt gcaaaaaagc ggttagctcc
6601 ttcggtcctc cgatcgttgt cagaagtaag ttggccgcag tgttatcact catggttatg
6661 gcagcactgc ataattctct tactgtcatg ccatccgtaa gatgcttttc tgtgactggt
6721 gagtactcaa ccaagtcatt ctgagaatag tgtatgcggc gaccgagttg ctcttgcccg
6781 gcgtcaatac gggataatac cgcgccacat agcagaactt taaaagtgct catcattgga
6841 aaacgttctt cggggcgaaa actctcaagg atcttaccgc tgttgagatc cagttcgatg
6901 taacccactc gtgcacccaa ctgatcttca gcatctttta ctttcaccag cgtttctggg
6961 tgagcaaaaa caggaaggca aaatgccgca aaaaagggaa taagggcgac acggaaatgt
7021 tgaatactca tactcttcct ttttcaatat tattgaagca tttatcaggg ttattgtctc
7081 atgagcggat acatatttga atgtatttag aaaaataaac aGCGATCGCG CGGCGCGggg
7141 taataactga tataattaaa ttgaagctct aatttgtgAC TTTAGTATAC ATGCATTTAC
7201 TTATAATACA GTTTTTTAGT TTTGCTGGCC GCATCTTCTC AAATATGCTT CCCAGCCTGC
7261 TTTTCTGTAA CGTTCACCCT CTACCTTAGC ATCCCTTCCC TTTGCAAATA GTCCTCTTCC
7321 AACAATAATA ATGTCAGATC CTGTAGAGAC CACATCATCC ACGGTTCTAT ACTGTTGACC
7381 CAATGCGTCT CCCTTGTCAT CTAAACCCAC ACCGGGTGTC ATAATCAACC AATCGTAACC
7441 TTCATCTCTT CCACCCATGT CTCTTTGAGC AATAAAGCCG ATAACAAAAT CTTTGTCGCT
7501 CTTCGCAATG TCAACAGTAC CCTTAGTATA TTCTCCAGTA GCTAGGGAGC CCTTGCATGA
7561 CAATTCTGCT AACATCAAAA GGCCTCTAGG TTCCTTTGTT ACTTCTTCCG CCGCCTGCTT
7621 CAAACCGCTA ACAATACCTG GGCCCACCAC ACCGTGTGCA TTCGTAATGT CTGCCCATTC
7681 TGCTATTCTG TATACACCCG CAGAGTACTG CAATTTGACT GTATTACCAA TGTCAGCAAA
7741 TTTTCTGTCT TCGAAGAGTA AAAAATTGTA CTTGGCGGAT AATGCCTTTA GCGGCTTAAC
7801 TGTGCCCTCC ATGGAAAAAT CAGTCAAGAT ATCCACATGT GTTTTTAGTA AACAAATTTT
7861 GGGACCTAAT GCTTCAACTA ACTCCAGTAA TTCCTTGGTG GTACGAACAT CCAATGAAGC
7921 ACACAAGTTT GTTTGCTTTT CGTGCATGAT ATTAAATAGC TTGGCAGCAA CAGGACTAGG
7981 ATGAGTAGCA GCACGTTCCT TATATGTAGC TTTCGACATG ATTTATCTTC GTTTCCTGCA
8041 GGTTTTTGTT CTGTGCAGTT GGGTTAAGAA TACTGGGCAA TTTCATGTTT CTTCAACACC
8101 ACATATGCGT ATATATACCA ATCTAAGTCT GTGCTCCTTC CTTCGTTctt ccttctgCtc
8161 ggagattacc gaatcAAAGC TAGC
```

Figure 12
(a)
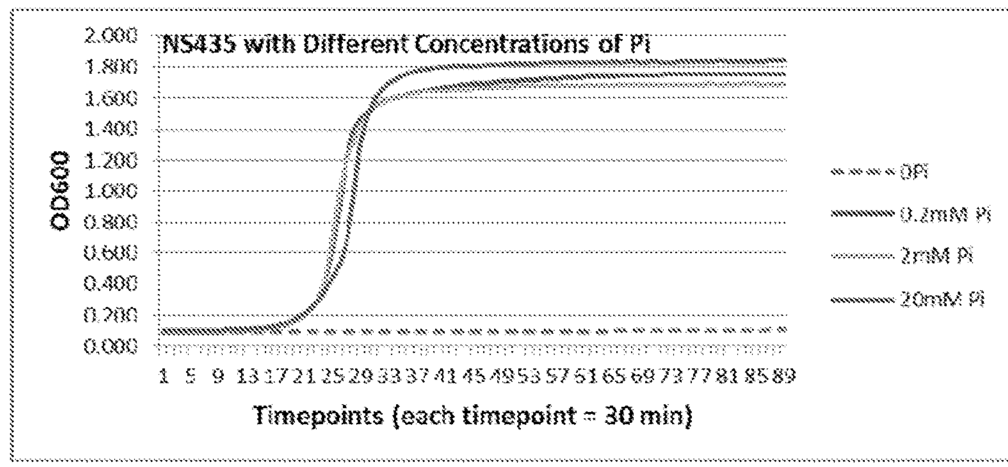
(b)
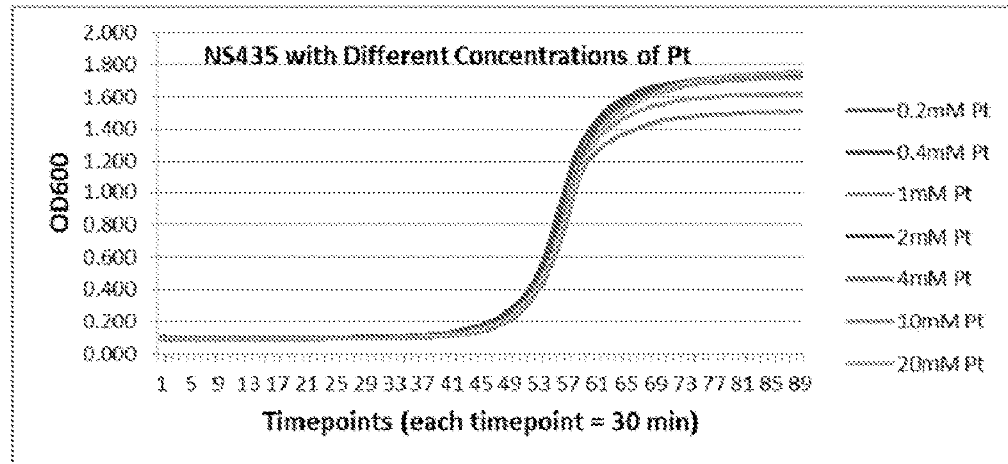

Figure 14

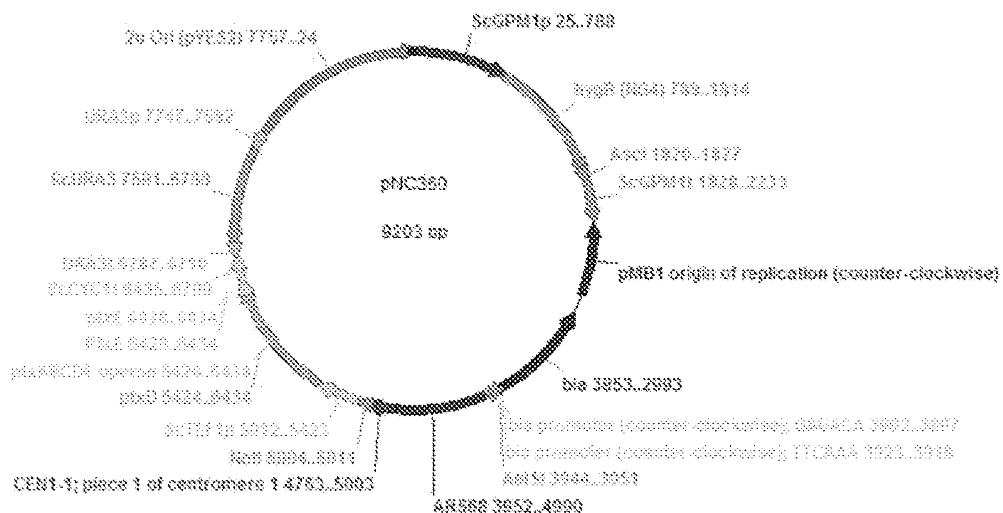

Figure 15

```
LOCUS       pNC360                 9203 bp ds-DNA     circular     09-JUL-2014
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    join(7757..9203,1..24)
                     /label=2u Ori (pYES2)
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     misc_feature    25..788
                     /label=ScGPM1p
                     /ApEinfo_fwdcolor=#c70cdc
                     /ApEinfo_revcolor=#c70cdc
                     /ApEinfo_graphicformat=arrow_data {{0 1 2 0 0 -1} {} 0}
                     width 5 offset 0
```

Figure 15 (continued)

```
rep_origin      3952..4990
                /note="ARS68"
                /label=ARS68
                /ApEinfo_fwdcolor=$ff0080
                /ApEinfo_revcolor=$ff0080
                /ApEinfo_graphicformat=arrow_data {{0 1 2 0 0 -1} {} 0}
                width 5 offset 0
misc_feature    1828..2233
                /label=ScGPM1t
                /ApEinfo_fwdcolor=$eb74f8
                /ApEinfo_revcolor=$eb74f8
                /ApEinfo_graphicformat=arrow_data {{0 1 2 0 0 -1} {} 0}
                width 5 offset 0
gene            5424..6434
                /gene="ptxABCDE operon"
                /note="phosphite oxidation operon"
                /label=ptxABCDE operon
                /ApEinfo_fwdcolor=pink
                /ApEinfo_revcolor=pink
                /ApEinfo_graphicformat=arrow_data {{0 1 2 0 0 -1} {} 0}
                width 5 offset 0
CDS             complement(6788..7591)
                /label=ScURA3
                /ApEinfo_fwdcolor=$00c4c4
                /ApEinfo_revcolor=$00c4c4
                /ApEinfo_graphicformat=arrow_data {{0 1 2 0 0 -1} {} 0}
                width 5 offset 0
misc_feature    complement(7592..7747)
                /label=URA3p
                /ApEinfo_fwdcolor=$ff8000
                /ApEinfo_revcolor=green
                /ApEinfo_graphicformat=arrow_data {{0 1 2 0 0 -1} {} 0}
                width 5 offset 0
rep_origin      complement(2234..2822)
                /note="pMB1 origin of replication (counter-clockwise)
                (RNAII -35 to RNA/DNA switch point)"
                /label=pMB1 origin of replication (counter-clockwise) (RN
                /ApEinfo_fwdcolor=$ff0000
                /ApEinfo_revcolor=$ff0000
                /ApEinfo_graphicformat=arrow_data {{0 1 2 0 0 -1} {} 0}
                width 5 offset 0
misc_feature    6435..6709
                /label=ScCYC1t
                /ApEinfo_fwdcolor=$00ffff
                /ApEinfo_revcolor=green
                /ApEinfo_graphicformat=arrow_data {{0 1 2 0 0 -1} {} 0}
                width 5 offset 0
misc_feature    4763..5003
                /note="CEN1-1; piece 1 of centromere 1"
                /label=CEN1-1; piece 1 of centromere 1
                /ApEinfo_fwdcolor=$ff00ff
                /ApEinfo_revcolor=$ff00ff
                /ApEinfo_graphicformat=arrow_data {{0 1 2 0 0 -1} {} 0}
                width 5 offset 0
misc_feature    5012..5423
                /label=ScTEF1p
                /ApEinfo_fwdcolor=$00ffff
                /ApEinfo_revcolor=green
```

Figure 15 (continued)

```
                     /ApEinfo_graphicformat=arrow_data {{0 1 2 0 0 -1} {} 0}
                     width 5 offset 0
     -10_signal      complement(3897..3902)
                     /note="bla promoter (counter-clockwise); GAGACA"
                     /label=bla promoter (counter-clockwise); GAGACA
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     CDS             789..1814
                     /label=hygR (NG4)
                     /ApEinfo_fwdcolor=$00d700
                     /ApEinfo_revcolor=$00a200
                     /ApEinfo_graphicformat=arrow_data {{0 1 2 0 0 -1} {} 0}
                     width 5 offset 0
     misc_feature    complement(6710..6787)
                     /label=URA3t
                     /ApEinfo_fwdcolor=$ff00ff
                     /ApEinfo_revcolor=green
                     /ApEinfo_graphicformat=arrow_data {{0 1 2 0 0 -1} {} 0}
                     width 5 offset 0
     gene            5424..6434
                     /gene="ptxD"
                     /label=ptxD
                     /ApEinfo_fwdcolor=$00e800
                     /ApEinfo_revcolor=$00e800
                     /ApEinfo_graphicformat=arrow_data {{0 1 2 0 0 -1} {} 0}
                     width 5 offset 0
     gene            complement(2993..3853)
                     /gene="bla"
                     /label=bla
                     /ApEinfo_fwdcolor=$ff0000
                     /ApEinfo_revcolor=$ff0000
                     /ApEinfo_graphicformat=arrow_data {{0 1 2 0 0 -1} {} 0}
                     width 5 offset 0
     -35_signal      complement(3918..3923)
                     /note="bla promoter (counter-clockwise); TTCAAA"
                     /label=bla promoter (counter-clockwise); TTCAAA
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     misc_feature    3944..3951
                     /label=AsiSI
                     /ApEinfo_fwdcolor=$ff8040
                     /ApEinfo_revcolor=$ff8040
                     /ApEinfo_graphicformat=arrow_data {{0 1 2 0 0 -1} {} 0}
                     width 5 offset 0
     misc_feature    1820..1827
                     /label=AscI
                     /ApEinfo_fwdcolor=$00b9b9
                     /ApEinfo_revcolor=$00b9b9
                     /ApEinfo_graphicformat=arrow_data {{0 1 2 0 0 -1} {} 0}
                     width 5 offset 0
     misc_feature    5004..5011
                     /label=NotI
                     /ApEinfo_fwdcolor=$ff8040
                     /ApEinfo_revcolor=$ff8040
```

Figure 15 (continued)

```
                     /ApEinfo_graphicformat=arrow_data {{0 1 2 0 0 -1} {} 0}
                     width 5 offset 0
     gene            6428..6434
                     /gene="ptxE"
                     /label=ptxE
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
     CDS             6428..6434
                     /gene="ptxE"
                     /note="putative transcriptional regulator of ptx operon;
                     similar to lysR family of transcriptional regulators"
                     /codon_start=1
                     /transl_table=11
                     /product="PtxE"
                     /protein_id="AAC71710.1"
                     /db_xref="GI:3127081"
                     /translation="MLRFVWLKSLVAIVQTGSFQSAAPALGLAQPTVSQRLQKLEEQV
                     GVTLVQRSRSGCQPTTRALAFMPHATALLDMHARALEALSGNREPVGASSNIGTYLLQ
                     PSVKNYLTTANERGEVDLRIAANPDVADQLLAGQLDAAIMEWWLPHPDFEYPLWRVEP
                     LVLIVSPDHALAEAGCIERDKLVDLPMLGGEPGSGT"
                     /label=PtxE
                     /ApEinfo_fwdcolor=pink
                     /ApEinfo_revcolor=pink
                     /ApEinfo_graphicformat=arrow_data {{0 1 2 0 0 -1} {} 0}
                     width 5 offset 0
ORIGIN
        1 GTTTGTGGAA GCGGTATTCG CAATCATTTA GTCGTGCAAT GTATGACTTT AAGATTTGTG
       61 AGCAGGAAGA AAAGGGAGAA TCTTCTAACG ATAAACCCTT GAAAAACTGG GTAGACTACG
      121 CTATGTTGAG ttgctacgca ggctgcacaa ttacACGAGA ATGCTCCCGC CTAGGATTTA
      181 AGGCTAAGGG ACGTGCAATG CAGACGACAG ATCTAAATGA CCGTGTCGGT GAAGTGTTCG
      241 CCAAACTTTT CGGTTAACAC ATGCAGTGAT GCACGGCGGA TGGTGCTAAG TTACATATAT
      301 ATATATATAT ATATATATAT ATATATATAG CCATAGTGAT GTCTAAGTAA CCTTTATGCT
      361 ATATTTCTTA ATGTGGAAAG ATACTAGCGC GCGCACCCAC ACACAAGCTT CGTCTTTTCT
      421 TGAAGAAAAG AGGAAGCTCG CTAAATGGGA TTCCACTTTC CGTTCCCTGC CAGCTGATGG
      481 AAAAAGGTTA GTGGAACGAT GAAGAATAAA AAGAGAGATC CACTGAGGTG AAATTTCAGC
      541 TGACAGCGAG TTTCATGATC GTGATGAACA ATGCTAACGA GTTGTGCCTG TTGCCAGGGA
      601 GGGTGGTTCT CAACTTTTAA TGTATGGCCA AATCGCTACT TGGGTTTGTT ATATAACAAA
      661 GAAGAAATAA TGAACTGATT CTCTTCCTCC TTCTTGTCCT TTCTTAATTC TGTTGTAATT
      721 ACCTTCCTTT GTAATTTTTT TTGTAATTAT TCTTCTTAAT AATCCAAACA AACACACATA
      781 TTACAATAAT GAAGAAGCCC GAGCTGACCG CTACCTCTGT TGAGAAGTTC CTGATTGAGA
      841 AGTTTGATTC CGTTTCCGAC CTGATGCAGC TGTCCGAGGG CGAGGAGTCT CGAGCCTTCT
      901 CCTTTGACGT GGGCGGACGA GGTTACGTTC TGCGAGTGAA CTCGTGTGCC GACGGCTTCT
      961 ACAAGGATCG ATACGTCTAC CGACACTTTG CTTCTGCCGC TCTGCCCATC CCTGAGGTTC
     1021 TCGACATTGG CGAGTTCTCT GAGTCCCTCA CCTACTGCAT CTCTCGACGA GCTCAGGGAG
     1081 TCACCCTGCA GGACCTCCCT GAGACTGAGC TGCCTGCTGT CCTCCAGCCT GTTGCTGAGG
     1141 CCATGGACGC TATCGCTGCT GCTGATCTGT CCCAGACCTC CGGTTTCGGC CCCTTTGGAC
     1201 CTCAGGGAAT TGGACAGTAC ACCACTTGGC GAGACTTCAT CTGTGCTATT GCCGATCCTC
     1261 ACGTCTACCA TTGGCAGACC GTTATGGACG ATACTGTGTC GGCTTCTGTC GCTCAGGCTC
     1321 TGGACGAGCT GATGCTCTGG GCCGAGGATT GCCCCGAGGT TCGACACCTG GTGCATGCTG
     1381 ACTTCGGTTC CAACAACGTT CTCACCGACA ACGGCCGAAT CACTGCCGTG ATTGACTGGT
     1441 CCGAGGCTAT GTTTGGCGAC TCGCAGTACG AGGTGGCCAA CATCTTCTTT TGGCGACCCT
     1501 GGCTGGCTTG TATGGAGCAG CAGACCCGAT ACTTCGAGCG ACGACATCCT GAGCTCGCTG
     1561 GATCCCCTCG ACTGCGAGCT TACATGCTCC GAATTGGTCT GGACCAGCTC TACCAGTCGC
     1621 TGGTGGATGG CAACTTTGAC GATGCTGCCT GGGCTCAGGG ACGATGTGAC GCCATCGTGC
     1681 GATCTGGCGC TGGAACCGTC GGACGAACTC AGATTGCCCG ACGATCCGCT GCTGTCTGGA
     1741 CCGACGGATG CGTGGAGGTC CTGGCTGATT CGGGTAACCG ACGACCCTCT ACTCGACCTC
```

Figure 15 (continued)

1801 GAGCTAAGGA GTAAtaaacg gcgcgccGTC TGAAGAATGA ATGATTTGAT GATTTCTTTT
1861 TCCCTCCATT TTTCTTACTG AATATATCAA TGATATAGAC TTGTATAGTT TATTATTTCA
1921 AATTAAGTAG CTATATATAG TCAAGATAAC GTTTGTTTGA CACGATTACA TTATTCGTCG
1981 ACATCTTTTT TCAGCCTGTC GTGGTAGCAA TTTGAGGAGT ATTATTAATT GAATAGGTTC
2041 ATTTTGCGCT CGCATAAACA GTTTTCGTCA GGGACAGTAT GTTGGAATGA GTGGTAATTA
2101 ATGGTGACAT GACATGTTAT AGCAATAACC TTGATGTTTA CATCGTAGTT TAATGTACAC
2161 CCCGCGAATT CGTTCAAGTA ggagtgcacc aattgcaaag ggaaAAGCTG AATCGGCAGT
2221 TCGAATAGTA CTTtttccat aggctccgcc cccctgacga gcatcacaaa aatcgacgct
2281 caagtcagag gtggcgaaac ccgacaggac tataaagata ccaggcgttt ccccctggaa
2341 gctccctcgt gcgctctcct gttccgaccc tgccgcttac cggatacctg tccgcctttc
2401 tcccttcggg aagcgtggcg ctttctcata gctcacgctg taggtatctc agttcggtgt
2461 aggtcgttcg ctccaagctg ggctgtgtgc acgaaccccc cgttcagccc gaccgctgcg
2521 ccttatccgg taactatcgt cttgagtcca acccggtaag acacgactta tcgccactgg
2581 cagcagccac tggtaacagg attagcagag cgaggtatgt aggcggtgct acagagttct
2641 tgaagtggtg gcctaactac ggctacacta gaagaacagt atttggtatc tgcgctctgc
2701 tgaagccagt taccttcgga aaaagagttg gtagctcttg atccggcaaa caaaccaccg
2761 ctggtagcgg tggttttttt gtttgcaagc agcagattac gcgcagaaaa aaaggatctc
2821 aagaagatcc tttgatcttt tctacggggt ctgacgctca gtggaacgaa aactcacgtt
2881 aagggatttt ggtcatgaga ttatcaaaaa ggatcttcac ctagatcctt ttaaattaaa
2941 aatgaagttt taaatcaatc taaagtatat atgagtaaac ttggtctgac agttaccaat
3001 gcttaatcag tgaggcacct atctcagcga tctgtctatt tcgttcatcc atagttgcct
3061 gactccccgt cgtgtagata actacgatac gggagggctt accatctggc cccagtgctg
3121 caatgatacc gcgagaccca cgctcaccgg ctccagattt atcagcaata aaccagccag
3181 ccggaagggc cgagcgcaga agtggtcctg caactttatc cgcctccatc cagtctatta
3241 attgttgccg ggaagctaga gtaagtagtt cgccagttaa tagtttgcgc aacgttgttg
3301 ccattgctac aggcatcgtg gtgtcacgct cgtcgtttgg tatggcttca ttcagctccg
3361 gttcccaacg atcaaggcga gttacatgat cccccatgtt gtgcaaaaaa gcggttagct
3421 ccttcggtcc tccgatcgtt gtcagaagta agttggccgc agtgttatca ctcatggtta
3481 tggcagcact gcataattct cttactgtca tgccatccgt aagatgcttt tctgtgactg
3541 gtgagtactc aaccaagtca ttctgagaat agtgtatgcg gcgaccgagt tgctcttgcc
3601 cggcgtcaat acgggataat accgcgccac atagcagaac tttaaaagtg ctcatcattg
3661 gaaaacgttc ttcggggcga aaactctcaa ggatcttacc gctgttgaga tccagttcga
3721 tgtaacccac tcgtgcaccc aactgatctt cagcatcttt tactttcacc agcgtttctg
3781 ggtgagcaaa aacaggaagg caaaatgccg caaaaaaggg aataagggcg acacggaaat
3841 gttgaatact catactcttc ctttttcaat attattgaag catttatcag ggttattgtc
3901 tcatgagcgg atacatattt gaatgtattt agaaaaataa acaGCGATCG CAGCTAGCTC
3961 GTCGTGTTCA GGAACtgttc gatggttcgg agagagtcgc cgcccagaac atacgcgcac
4021 cgatgtcagc agacagcctt attacaagta tattcaagca agtatatccg tagggtgcgg
4081 gtgatttgga tctaaggttc gtactcaaca ctcacgagca gcttgcctat gttacatcct
4141 tttatcagac ataacataat tggagtttac ttacacacgg ggtgtacctg tatgagcacc
4201 acctacaatt gtagcactgg tacttgtaca aagaatttat tcgtacgaat cacagggacg
4261 gccgccctca ccgaaccagc gaatacctca gcggtcccct gcagtgactc aacaaagcga
4321 tatgaacatc ttgcgatggt atcctgctga tagtttttac tgtacaaaca cctgtgtagc
4381 tccttctagc atttttaagt tattcacacc tcaaggggag ggataaatta aataaattcc
4441 aaaagcgaag atcgagaaac taaattaaaa ttccaaaaac gaagttggaa cacaaccccc
4501 cgaaaaaaaa caacaaacaa aaaacccaac aaaataaaca aaaacaaaat aaatatataa
4561 ctaccagtat ctgactaaaa gttcaaatac tcgtacttac aacaaataga aatgagccgg
4621 ccaaaattct gcagaaaaaa atttcaaaca agtactggta taattaaatt aaaaaacaca
4681 tcaaagtatc ataacgttag ttattttatt ttatttaata aaagaaaaca acaagatggg
4741 ctcaaaactt tcaacttata cgATACATAC CAAATAACAA TTTAGTATTT ATCTAAGTGC
4801 TTTTCGTAGA TAATGGAATA CAAATGGATA TCCAGAGTAT ACACATGGAT AGTATACACT
4861 GACACGACAA TTCTGTATCT CTTTATGTTA ACTACTGTGA GGCATTAAAT AGAGCTTGAT
4921 ATATAAAATG TTACATTTCA CAGTCTGAAC TTTTGCAGAT TACCTAATtt ggtaagatat
4981 taattatgaa ctgaaagttg atgGCGGCCG CATAGCTTCA AAATGTTTCT ACTCCTTTTT
5041 TACTCTTCCA GATTTTCTCG GACTCCGCGC ATCGCCGTAC CACTTCAAAA CACCCAAGCA
5101 CAGCATACTA AATTTCCCCT CTTTCTTCCT CTAGGGTGTC GTTAATTACC CGTACTAAAG
5161 GTTTGGAAAA GAAAAAAGAG ACCGCCTCGT TTCTTTTTCT TCGTCGAAAA AGGCAATAAA
5221 AATTTTTATC ACGTTTCTTT TTCTTGAAAA TTTTTTTTTT TGATTTTTTT CTCTTTCGAT

Figure 15 (continued)

```
5281 GACCTCCCAT TGATATTTAA GTTAATAAAC GGTCTTCAAT TTCTCAAGTT TCAGTTTCAT
5341 TTTTCTTGTT CTATTACAAC TTTTTTTACT TCTTGCTCAT TAGAAAGAAA GCATAGCAAT
5401 CTAATCTAAG TTTTAATTAC AAAatgctgc cgaaactcgt tataactcac cgagtacacg
5461 atgagatcct gcaactgctg gcgcccacatt gcgagctgat gaccaaccag accgacagca
5521 cgctgacgcg cgaggaaatt ctgcgccgct gtcgcgatgc tcaggcgatg atggcgttca
5581 tgcccgatcg ggtcgatgca gactttcttc aagcctgccc tgagctgcgt gtagtcggct
5641 gcgcgctcaa gggcttcgac aatttcgatg tggacgcctg tactgcccgc ggggtctggc
5701 tgaccttcgt gcctgatctg ttgacggtcc cgactgccga gctggcgatc ggactggcgg
5761 tggggctggg gcggcatctg cgggcagcag atgcgttcgt ccgctctggc gagttccagg
5821 gctggcaacc acagttctac ggcacggggc tggataacgc tacggtcggc atccttggca
5881 tgggcgccat cggactggcc atggctgatc gcttgcaggg atggggcgcg accctgcagt
5941 accacgaggc gaaggctctg gatacacaaa ccgagcaacg gctcggcctg cgccaggtgg
6001 cgtgcagcga actcttcgcc agctcggact tcatcctgct ggcgcttccc ttgaatgccg
6061 ataccagca tctggtcaac gccgagctgc ttgccctcgt acggccgggc gctctgcttg
6121 taaaccctg tcgtggttcg gtagtggatg aagccgccgt gctcgcggcg cttgagcgag
6181 gccagctcgg cgggtatgcg gcggatgtat tcgaaatgga agactgggct cgcgcggacc
6241 ggccgcggct gatcgatcct gcgctgctcg cgcatccgaa tacgctgttc actccgcaca
6301 tagggtcggc agtgcgcgcg gtgcgcctgg agattgaacg ttgtgcagcg cagaacatca
6361 tccaggtatt ggcaggtgcg cgcccaatca acgctgcgaa ccgtctgccc aaggccgagc
6421 ctgccgcatg ttgaacaggc ccctttcct ttgtcgatat catgtaatta gttatgtcac
6481 gcttacattc acgccctcct cccacatccg ctctaaccga aaaggaagga gttagacaac
6541 ctgaagtcta ggtccctatt tatttttttt aatagttatg ttagtattaa gaacgttatt
6601 tatatttcaa atttttcttt ttttctgta caaacgcgtg tacgcatgta acattatact
6661 gaaaaccttg cttgagaagg ttttgGGACG CTCGAAGGCT TTAATTTGCg ggtaataact
6721 gatataatta aattgaagct ctaatTTGTG AGTTTAGTAT ACATGCATTT ACTTATAATA
6781 CAGTTTTTTA GTTTTGCTGG CCGCATCTTC TCAAATATGC TTCCCAGCCT GCTTTTCTGT
6841 AACGTTCACC CTCTACCTTA GCATCCCTTC CCTTTGCAAA TAGTCCTCTT CCAACAATAA
6901 TAATGTCAGA TCCTGTAGAG ACCACATCAT CCACGGTTCT ATACTGTTGA CCCAATGCGT
6961 CTCCCTTGTC ATCTAAACCC ACACCGGGTG TCATAATCAA CCAATCGTAA CCTTCATCTC
7021 TTCCACCCAT GTCTCTTTGA GCAATAAAGC CGATAACAAA ATCTTTGTCG CTCTTCGCAA
7081 TGTCAACAGT ACCCTTAGTA TATTCTCCAG TAGCTAGGGA GCCCTTGCAT GACAATTCTG
7141 CTAACATCAA AAGGCCTCTA GGTTCCTTTG TTACTTCTTC CGCCGCCTGC TTCAAACCGC
7201 TAACAATACC TGGGCCCACC ACACCGTGTG CATTCGTAAT GTCTGCCCAT TCTGCTATTC
7261 TGTATACACC CGCAGAGTAC TGCAATTTGA CTGTATTACC AATGTCAGCA AATTTTCTGT
7321 CTTCGAAGAG TAAAAAATTG TACTTGGCGG ATAATGCCTT TAGCGGCTTA ACTGTGCCCT
7381 CCATGGAAAA ATCAGTCAAG ATATCCACAT GTGTTTTTAG TAAACAAATT TTGGGACCTA
7441 ATGCTTCAAC TAACTCCAGT AATTCCTTGG TGGTACGAAC ATCCAATGAA GCACACAAGT
7501 TTGTTTGCTT TTCGTGCATG ATATTAAATA GCTTGGCAGC AACAGGACTA GGATGAGTAG
7561 CAGCACGTTC CTTATATGTA GCTTTCGACA TGATTTATCT TCGTTTCCTG CAGGTTTTTG
7621 TTCTGTGCAG TTGGGTTAAG AATACTGGGC AATTTCATGT TTCTTCAACA CCACATATGC
7681 GTATATATAC CAATCTAAGT CTGTGCTCCT TCCTTCGTTc ttccttctgC tcggagatta
7741 ccgaatcAAA GCTAGCTTAT CGATGATAAG CTGTCAAAGA TGAGAATTAA TTCCACGGAC
7801 TATAGACTAT ACTAGATACT CCGTCTACTG TACGATACAC TTCCGCTCAG GTCCTTGTCC
7861 TTTAACGAGG CCTTACCACT CTTTTGTTAC TCTATTGATC CAGCTCAGCA AAGGCAGTGT
7921 GATCTAAGAT TCTATCTTCG CGATGTAGTA AAACTAGCTA GACCGAGAAA GAGACTAGAA
7981 ATGCAAAAGG CACTTCTACA ATGGCTGCCA TCATTATTAT CCGATGTGAC GCTGCAGCTT
8041 CTCAATGATA TTCGAATACG CTTTGAGGAG ATACAGCCTA ATATCCGACA AACTGTTTTA
8101 CAGATTTACG ATCGTACTTG TTACCCATCA TTGAATTTTG AACATCCGAA CCTGGGAGTT
8161 TTCCCTGAAA CAGATAGTAT ATTTGAACCT GTATAATAAT ATATAGTCTA GCGCTTTACG
8221 GAAGACAATG TATGTATTTC GGTTCCTGGA GAAACTATTG CATCTATTGC ATAGGTAATC
8281 TTGCACGTCG CATCCCCGGT TCATTTTCTG CGTTTCCATC TTGCACTTCA ATAGCATATC
8341 TTTGTTAACG AAGCATCTGT GCTTCATTTT GTAGAACAAA AATGCAACGC GAGAGCGCTA
8401 ATTTTTCAAA CAAAGAATCT GAGCTGCATT TTTACAGAAC AGAAATGCAA CGCGAAAGCG
8461 CTATTTTACC AACGAAGAAT CTGTGCTTCA TTTTTGTAAA ACAAAAATGC AACGCGACGA
8521 GAGCGCTAAT TTTTCAAACA AAGAATCTGA GCTGCATTTT TACAGAACAG AAATGCAACG
8581 CGAGAGCGCT ATTTTACCAA CAAAGAATCT ATACTTCTTT TTTGTTCTAC AAAAATGCAT
8641 CCCGAGAGCG CTATTTTTCT AACAAAGCAT CTTAGATTAC TTTTTTTCTC CTTTGTGCGC
8701 TCTATAATGC AGTCTCTTGA TAACTTTTTG CACTGTAGGT CCGTTAAGGT TAGAAGAAGG
```

Figure 15 (continued)

```
8761 CTACTTTGGT GTCTATTTTC TCTTCCATAA AAAAAGCCTG ACTCCACTTC CCGCGTTTAG
8821 TGATTACTAG CGAAGCTGCG GGTGCATTTT TTCAAGATAA AGGCATCCCC GATTATATTC
8881 TATACCGATG TGGATTGCGC ATACTTTGTG AACAGAAAGT GATAGCGTTG ATGATTCTTC
8941 ATTGGTCAGA AAATTATGAA CGGTTTCTTC TATTTTGTCT CTATATACTA CGTATAGGAA
9001 ATGTTTACAT TTTCGTATTG TTTTCGATTC ACTCTATGAA TAGTTCTTAC TACAATTTTT
9061 TTGTCTAAAG AGTAATACTA GAGATAAACA TAAAAAATGT AGAGGTCGAG TTTAGATGCA
9121 AGTTCAAGGA GCGAAAGGTG GATGGGTAGG TTATATAGGG ATATAGCACA GAGATATATA
9181 GCAAAGAGAT ACTTTTGAGC AAT
```

Figure 16

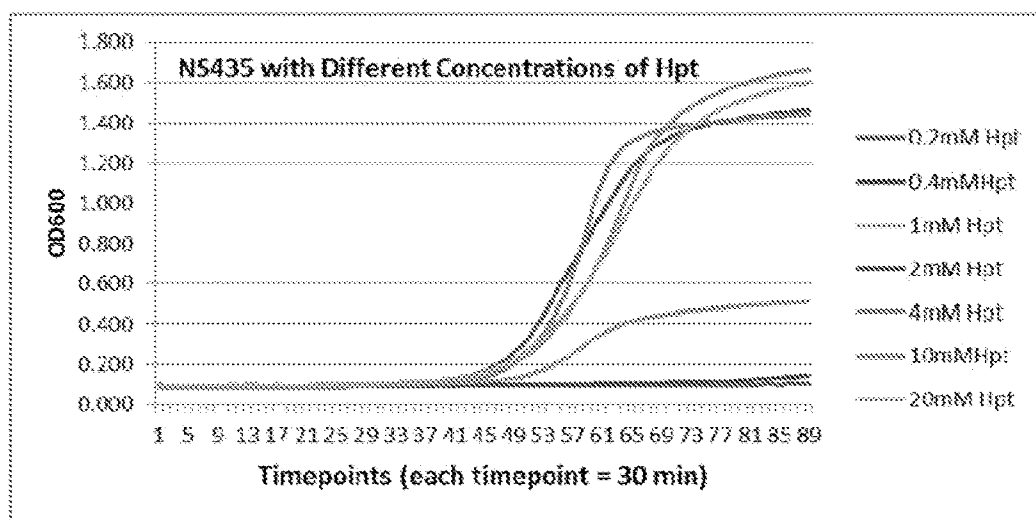

Figure 18

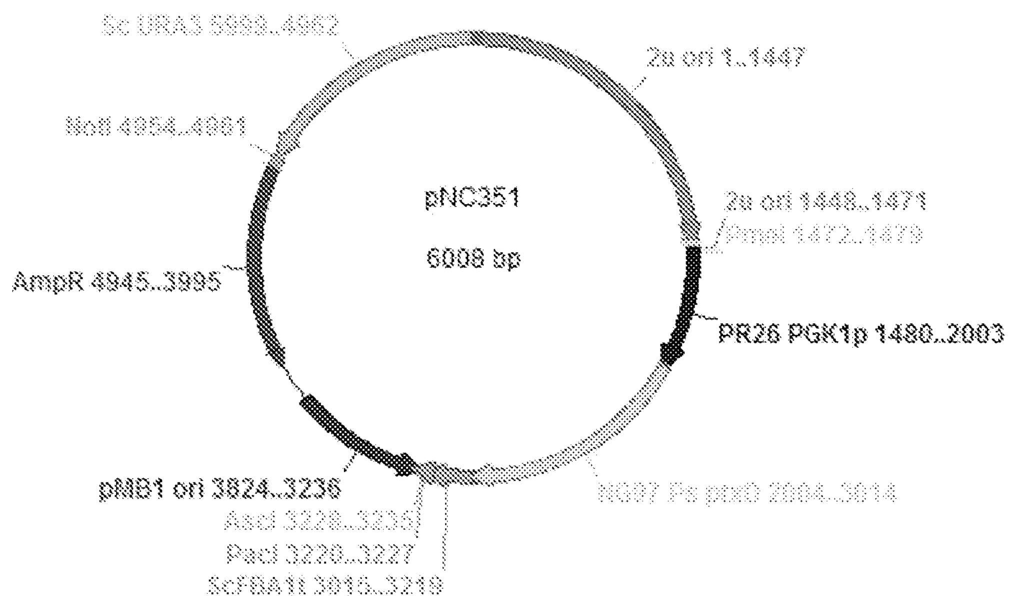

Figure 19

```
LOCUS       pNC351              6008 bp ds-DNA     circular     21-MAR-2014
DEFINITION  .
ACCESSION
VERSION
SOURCE      .
  ORGANISM  .
COMMENT
COMMENT
COMMENT     ApEinfo:methylated:1
FEATURES             Location/Qualifiers
     misc_feature    1448..1471
                     /label=2u ori
                     /ApEinfo_fwdcolor=#8080ff
                     /ApEinfo_revcolor=#8080ff
                     /ApEinfo_graphicformat=arrow_data {{0 1 2 0 0 -1} {} 0}
                     width 5 offset 0
     misc_feature    1..1447
                     /label=2u ori(1)
                     /ApEinfo_label=2u ori
                     /ApEinfo_fwdcolor=#8080ff
                     /ApEinfo_revcolor=#8080ff
```

Figure 19 (continued)

```
                     /ApEinfo_graphicformat=arrow_data {{0 1 2 0 0 -1} {} 0}
                     width 5 offset 0
     rep_origin      complement(3236..3824)
                     /note="pMB1 origin of replication (counter-clockwise)
                     (RNAII -35 to RNA/DNA switch point)"
                     /label=pMB1 ori
                     /ApEinfo_fwdcolor=$ff0000
                     /ApEinfo_revcolor=$ff0000
                     /ApEinfo_graphicformat=arrow_data {{0 1 2 0 0 -1} {} 0}
                     width 5 offset 0
     misc_feature    complement(3995..4945)
                     /label=AmpR
                     /ApEinfo_fwdcolor=$ff00ff
                     /ApEinfo_revcolor=$ff00ff
                     /ApEinfo_graphicformat=arrow_data {{0 1 2 0 0 -1} {} 0}
                     width 5 offset 0
     misc_feature    3015..3219
                     /label=ScYBAlt
                     /ApEinfo_fwdcolor=$eb74f8
                     /ApEinfo_revcolor=$eb74f8
                     /ApEinfo_graphicformat=arrow_data {{0 1 2 0 0 -1} {} 0}
                     width 5 offset 0
     misc_feature    complement(4962..5999)
                     /label=Sc URA3
                     /ApEinfo_fwdcolor=cyan
                     /ApEinfo_revcolor=$00ff00
                     /ApEinfo_graphicformat=arrow_data {{0 1 2 0 0 -1} {} 0}
                     width 5 offset 0
     misc_feature    3228..3235
                     /label=AscI
                     /ApEinfo_fwdcolor=$00ff00
                     /ApEinfo_revcolor=green
                     /ApEinfo_graphicformat=arrow_data {{0 1 2 0 0 -1} {} 0}
                     width 5 offset 0
     misc_feature    4954..4961
                     /label=NotI
                     /ApEinfo_fwdcolor=$ff8080
                     /ApEinfo_revcolor=green
                     /ApEinfo_graphicformat=arrow_data {{0 1 2 0 0 -1} {} 0}
                     width 5 offset 0
     misc_feature    1472..1479
                     /label=PmeI
                     /ApEinfo_fwdcolor=$00ffff
                     /ApEinfo_revcolor=green
                     /ApEinfo_graphicformat=arrow_data {{0 1 2 0 0 -1} {} 0}
                     width 5 offset 0
     misc_feature    3220..3227
                     /label=PacI
                     /ApEinfo_fwdcolor=$ff8040
                     /ApEinfo_revcolor=green
                     /ApEinfo_graphicformat=arrow_data {{0 1 2 0 0 -1} {} 0}
                     width 5 offset 0
     misc_feature    1480..2003
                     /label=PR26 PGK1p
                     /ApEinfo_fwdcolor=$800040
                     /ApEinfo_revcolor=green
                     /ApEinfo_graphicformat=arrow_data {{0 1 2 0 0 -1} {} 0}
                     width 5 offset 0
     misc_feature    2004..3014
                     /label=NG97 Ps ptxD
                     /ApEinfo_fwdcolor=cyan
                     /ApEinfo_revcolor=green
                     /ApEinfo_graphicformat=arrow_data {{0 1 2 0 0 -1} {} 0}
                     width 5 offset 0
```

Figure 19 (continued)

```
ORIGIN
        1 ttatcgatga taagctgtca aagatgagaa ttaattccac ggactataga ctatactaga
       61 tactccgtct actgtacgat acacttccgc tcaggtcctt gtcctttaac gaggccttac
      121 cactcttttg ttactctatt gatccagctc agcaaaggca gtgtgatcta agattctatc
      181 ttcgcgatgt agtaaaacta gctagaccga gaaagagact agaaatgcaa aaggcacttc
      241 tacaatggct gccatcatta ttatccgatg tgacgctgca gcttctcaat gatattcgaa
      301 tacgcttgga ggagatacag cctaatatcc gacaaactgt tttacagatt tacgatcgta
      361 cttgttaccc atcattgaat tttgaacatc cgaacctggg agttttccct gaaacagata
      421 gtatatttga acctgtataa taatatatag tctagcgctt tacggaagac aatgtatgta
      481 tttcggttcc tggagaaact attgcatcta ttgcatatgt aatcttgcac gtcgcatccc
      541 cggttcattt tctgcgtttc catcttgcac ttcaatagca tatctttgtt aacgaagcat
      601 ctgtgcttca ttttgtagaa caaaaatgca acgcgagagc gctaattttt caaacaaaga
      661 atctgagctg catttttaca gaacagaaat gcaacgcgaa agcgctattt taccaacgaa
      721 gaatctgtgc ttcatttttg taaaacaaaa atgcaacgcg acgagagcgc taatttttca
      781 aacaaagaat ctgagctgca tttttacaga acagaaatgc aacgcgagag cgctatttta
      841 ccaacaaaga atctatactt cttttttgtt ctacaaaaat gcatcccgag agcgctattt
      901 ttctaacaaa gcatcttaga ttactttttt tctcctttgt gcgctctata atgcagtctc
      961 ttgataactt tttgcactgt aggtccgtta aggttagaag aaggctactt tggtgtctat
     1021 tttctcttcc ataaaaaaag cctgactcca cttcccgcgt ttactgatta ctagcgaagc
     1081 tgcgggtgca ttttttcaag ataaaggcat ccccgattat attctatacc gatgtggatt
     1141 gcgcatactt tgtgaacaga aagtgatagc gttgatgatt cttcattggt cagaaaatta
     1201 tgaacggttt cttctatttt gtctctatat actacgtata ggaaatgttt acattttcgt
     1261 attgttttcg attcactcta tgaatagttc ttactacaat ttttttgtct aaagagtaat
     1321 actagagata aacataaaaa atgtagaggt cgagtttaga tgcaagttca aggagcgaaa
     1381 ggtggatggg taggttatat agggatatag cacagagata tatagcaaag agatactttt
     1441 gagcaatgtt tGTGGAAGCG GTATTCGCAA TGTTTAAACc ccagcccgac ttttaacctc
     1501 aATAGCTAGC TACGCAACAG ACAGTTAAAG CTACGTACTC AACTATATAT TCCATTGACA
     1561 ATTGACAATT ACAACTGTTT CTTCTCCTGC ATCGTTCTCA TCCTCATTGC CTTATCTCCT
     1621 GTTATCAATT AATTATAATA ATATACTAGT TCTGAACTAA TTACCTGATC GCACGCAGTA
     1681 CGGCTGACGC GTATTATTGG ACCAACAAAC CCTAAAAATT GTTTCATCCA ATTGAACAGT
     1741 TCACGCAACC GTGATTGTGT CAAAAAGGCA TTGCCGGCCT CAAGTAGGCG CCCATGCTAC
     1801 GACTACTGCG GTCTAGCGGC TCCCGTATCC CTCAATCGTG GCCCTTTTCC GGTCTACCCG
     1861 CTGAGTCAGC CCCGCCCAAC AAAAAAAGCA CACCACAAGT TCGACATGGT CCAGGGGCAC
     1921 GGCTCCAGGG TTGCGGTATA AATACAGTCA CCATTTCCAC CGCACCTCCG TGctttgttt
     1981 ttcaattggc aacctataac acaATGCTGC CGAAACTCGT TATAACTCAC cgagtacacg
     2041 atgagatcct gcaactgctg gcgccacatt gcgagctgat gaccaaccag accgacagca
     2101 cgctgacgcg cgaggaaatt ctgcgccgct gtcgcgatgc tcaggcgatg atggcgttca
     2161 tgcccgatcg ggtcgatgca gactttcttc aagcctgccc tgagctgcgt gtagtcggct
     2221 gcgcgctcaa gggcttcgac aatttcgatg tggacgcctg tactgcccgc ggggtctggc
     2281 tgaccttcgt gcctgatctg ttgacggtcc cgactgccga gctggcgatc ggactggcgg
     2341 tggggctggg gcggcatctg cgggcagcag atgcgttcgt ccgctctggc gagttccagg
     2401 gctggcaacc acagttctac ggcacggggc tggataacgc tacggtcggc atccttggca
     2461 tgggcgccat cggactggcc atggctgatc gcttgcaggg atggggcgcg accctgcagt
     2521 accacgaggc gaaggctctg gatacacaaa ccgagcaacg gctcggcctg cgccaggtgg
     2581 cgtgcagcga actcttcgcc agctcggact tcatcctgct ggcgcttccc ttgaatgccg
     2641 atacccagca tctggtcaac gccgagctgc ttgccctcgt acggccgggc gctctgcttg
     2701 taaacccctg tcgtggttcg gtagtggatg aagccgccgt gctcgcggcg cttgagcgag
     2761 gccagctcgg cgggtatgcg gcggatgtat tcgaaatgga agactgggct cgcgcggacc
     2821 ggccgcggct gatcgatcct gcgctgctcg cgcatccgaa tacgctgttc actccgcaca
     2881 tagggtcggc agtgcgcgcg gtgcgcctgg agattgaacg ttgtgcagcg cagaacatca
     2941 tccaggtatt ggcaggtgcg cgcccaatca acgctgcgaa ccgtctgccc aaggCCGAGC
     3001 CTGCCGCATG TTCAgttaat tcaaattaat tgatatAGTT TTTTAATGAG TATTGAATCT
     3061 GTTTAGAAAT AATGGAATAT TATTTTTATT TATTTATTTA TATTATTGGT CGGCTCTTTT
     3121 CTTCTGAAGG TCAATGACAA AATGATATGA AGGAAATAAT GATTTCTAAA ATTTTACAAC
     3181 GTAAGATATT TTTACAAAAG CCTAGCTCAT CTTTTGTCAt taattaaggc gcgcctttcc
     3241 ataggctccg cccccctgac gagcatcacs aaaatcgacg ctcaagtcag aggtggcgaa
     3301 acccgacagg actataaaga taccaggcgt ttccccctgg aagctccctc gtgcgctctc
     3361 ctgttccgac cctgccgctt accggatacc tgtccgcctt tctcccttcg ggaagcgtgg
     3421 cgctttctca tagctcacgc tgtaggtatc tcagttcggt gtaggtcgtt cgctccaagc
     3481 tgggctgtgt gcacgaaccc cccgttcagc ccgaccgctg cgccttatcc ggtaactatc
     3541 gtcttgagtc caacccggta agacacgact tatcgccact ggcagcagcc actggtaaca
     3601 ggattagcag agcgaggtat gtaggcggtg ctacagagtt cttgaagtgg tggcctaact
     3661 acggctacac tagaagaaca gtatttggta tctgcgctct gctgaagcca gttaccttcg
     3721 gaaaaagagt tggtagctct tgatccggca aacaaaccac cgctggtagc ggtggttttt
     3781 ttgtttgcaa gcagcagatt acgcgcagaa aaaaaggatc tcaagaagat cctttgatct
     3841 tttctacggg gtctgacgct cagtggaacg aaaactcacg ttaagggatt ttggtcatga
```

Figure 19 (continued)

```
3901 gattatcaaa aaggatcttc acctagatcc ttttaaatta aaaatgaagt tttaaatcaa
3961 tctaaagtat atatgagtaa acttggtctg acagttacca atgcttaatc agtgaggcac
4021 ctatctcagc gatctgtcta tttcgttcat ccatagttgc ctgactcccc gtcgtgtaga
4081 taactacgat acgggagggc ttaccatctg gccccagtgc tgcaatgata ccgcgagacc
4141 cacgctcacc ggctccagat ttatcagcaa taaaccagcc agccggaagg gccgagcgca
4201 gaagtggtcc tgcaacttta tccgcctcca tccagtctat taattgttgc cgggaagcta
4261 gagtaagtag ttcgccagtt aatagtttgc gcaacgttgt tgccattgct acaggcatcg
4321 tggtgtcacg ctcgtcgttt ggtatggctt cattcagctc cggttcccaa cgatcaaggc
4381 gagttacatg atcccccatg ttgtgcaaaa aagcggttag ctccttcggt cctccgatcg
4441 ttgtcagaag taagttggcc gcagtgttat cactcatggt tatggcagca ctgcataatt
4501 ctcttactgt catgccatcc gtaagatgct tttctgtgac tggtgagtac tcaaccaagt
4561 cattctgaga atagtgtatg cggcgaccga gttgctcttg cccggcgtca atacgggata
4621 ataccgcgcc acatagcaga actttaaaag tgctcatcat tggaaaacgt tcttcggggc
4681 gaaaactctc aaggatctta ccgctgttga gatccagttc gatgtaaccc actcgtgcac
4741 ccaactgatc ttcagcatct tttactttca ccagcgtttc tgggtgagca aaaacaggaa
4801 ggcaaaatgc cgcaaaaaag ggaataaggg cgacacggaa atgttgaata ctcatactct
4861 tcctttttca atattattga agcatttatc agggttattg tctcatgagc ggatacatat
4921 ttgaatgtat ttagaaaaat aaacaGCGAT CGCGCGGCCG Cgggtaataa ctgatataat
4981 taaattgaag ctctaatttg tgACTTTACT ATACATCCAT TTACTTATAA TACAGTTTTT
5041 TAGTTTTGCT GGCCGCATCT TCTCAAATAT GCTTCCCAGC CTGCTTTTCT GTAACGTTCA
5101 CCCTCTACCT TAGCATCCCT TCCCTTTGCA AATAGTCCTC TTCCAACAAT AATAATGTCA
5161 GATCCTGTAG AGACCACATC ATCCACGGTT CTATACTGTT GACCCAATGC GTCTCCCTTG
5221 TCATCTAAAC CCACACCGGG TGTCATAATC AACCAATCGT AACCTTCATC TCTTCCACCC
5281 ATGTCTCTTT GAGCAATAAA GCCGATAACA AAATCTTTGT CGCTCTTCGC AATGTCAACA
5341 GTACCCTTAG TATATTCTCC AGTAGCTAGG GAGCCCTTGC ATGACAATTC TGCTAACATC
5401 AAAAGGCCTC TAGGTTCCTT TGTTACTTCT TCCGCCGCCT GCTTCAAACC GCTAACAATA
5461 CCTGGGCCCA CCACACCGTG TGCATTCGTA ATGTCTGCCC ATTCTGCTAT TCTGTATACA
5521 CCCGCAGAGT ACTGCAATTT GACTGTATTA CCAATGTCAG CAAATTTTCT GTCTTCGAAG
5581 AGTAAAAAAT TGTACTTGGC GGATAATGCC TTTAGCGGCT TAACTGTGCC CTCCATGGAA
5641 AAATCAGTCA AGATATCCAC ATGTGTTTTT AGTAAACAAA TTTTGGGACC TAATGCTTCA
5701 ACTAACTCCA GTAATTCCTT GGTGGTACGA ACATCCAATG AAGCACACAA GTTTGTTTGC
5761 TTTTCGTGCA TGATATTAAA TAGCTTGGCA GCAACAGGAC TAGGATGAGT AGCAGCACGT
5821 TCCTTATATG TAGCTTTCGA CATGATTTAT CTTCGTTTCC TGCAGGTTTT TGTTCTGTGC
5881 AGTTGGGTTA AGAATACTGG GCAATTTCAT GTTTCTTCAA CACCACATAT GCGTATATAT
5941 ACCAATCTAA GTCTGTGCTC CTTCCTTCGT Tcttccttct gCtcggagat taccgaatcA
6001 AAGCTAGC
```

MICROORGANISMS ENGINEERED TO USE UNCONVENTIONAL SOURCES OF PHOSPHOROUS OR SULFUR

RELATED APPLICATIONS

This application is the U.S. National Stage filed under 35 U.S.C. § 371 of PCT Patent Application serial number PCT/US2014/052841, filed Aug. 27, 2014, which claims the benefit of priority to United States Provisional Patent Application serial number 61/870,469, filed Aug. 27, 2013.

SEQUENCE LISTING

The instant application contains a Sequence Listing, which has been submitted electronically in ASCII format and is hereby incorporated by reference in its entirety. Said ASCII copy, created on Sept. 26, 2014, is named NGX-02325_SL.txt and is 76,068 bytes in size.

BACKGROUND

In the fermentation industry, cell culture media is typically formulated to provide all nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice and, unfortunately, for any potential contaminating organisms. In this environment the production organism is required to compete directly with any contaminant organism in the cell culture.

Even in robust hosts, the combination of opportunistic infections of the culture and the metabolic burden resulting from the demands of product manufacture is a major concern in monoculture operations. Industrial robustness is typically considered a multigenic trait specific to the host strain and thus difficult to engineer predictably into organisms late in the development process. Addition of selective growth inhibitors, such as bacterial antibiotics, is one method used to create a more robust fermentation environment for host organisms that are resistant to the growth inhibitor. However, antibiotic addition is often undesirable or unfeasible, and spontaneously resistant contaminations frequently result.

Accordingly, there exists a need for rationally engineered traits that, when engineered into a host organism, create a robust monoculture fermentation environment.

SUMMARY OF THE INVENTION

In certain embodiments, the invention relates to a genetically engineered organism, wherein the genetically engineered organism has been transformed by a nucleic acid molecule comprising any one of the sequences disclosed herein.

In certain embodiments, the invention relates to a genetically engineered organism, wherein the genetically engineered organism has been transformed by a nucleic acid molecule the nucleic acid molecule comprises a non-native gene; and the non-native gene encodes for a non-native enzyme selected from the group consisting of NAD:phosphite oxidoreductase (phosphite dehydrogenase), glycerol-3-phosphate dehydrogenase (sn-glycerol 3-phosphate: NAD (+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, and a NADH-FMN oxidoreductase.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction comprises, in an amount from about 10% by weight to about 100% by weight, a phosphorus-containing compound of any one of Formulas I-III;

the compound of formula I is

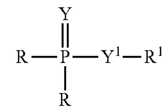

wherein, independently for each occurrence,

R is —H, alkyl, —OH, —$OR^2$, —SH, or —$SR^2$;

$R^1$ is —H, or alkyl;

Y is O or S;

$Y^1$ is O or S; and $R^2$ is alkyl;

the compound of formula II is

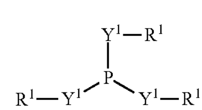

wherein, independently for each occurrence, $R^1$ is —H, or alkyl; and $Y^1$ is O or S;

the compound of formula III is

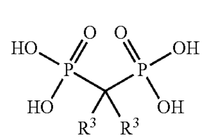

wherein, independently for each occurrence, $R^3$ is —H, —OH, —$OR^4$, —SH, —$SR^4$, halo, alkyl, aryl, heteroaryl, aralkyl, or heteroaralkyl; and $R^4$ is alkyl or aryl;

a native organism of the same species as the genetically engineered organism could not metabolize (i.e., use as a source of phosphorus) the phosphorus-containing compound; and the genetically engineered organism converts the substrate to a product.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction comprises, in an amount from about 10% by weight to about 100% by weight, a sulfur-containing compound of any one of Formulas IV-XI;

the compound of formula IV is

IV

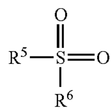

wherein, independently for each occurrence, $R^5$ is —H, —OH, —$OR^7$, —SH, —$SR^7$, $R^7$, halo, alkyl, aryl, heteroaryl, aralkyl, heteroaralkyl, —$SO_2$H, —$NHR^7$, or —NH—C(═O)—$R^7$;

$R^6$ is —H, —OH, —$OR^7$, —SH, —$SR^7$, $R^7$, halo, alkyl, aryl, heteroaryl, aralkyl, heteroaralkyl, —$SO_2$H, —$NHR^7$, or —NH—C(═O)—$R^7$; and $R^7$ is cycloalkyl, alkyl, or aryl, or any two $R^7$, taken together, form a 5- or 6-membered ring:

the compound of formula V, formula VI, or formula VII, is

V

VI

VII

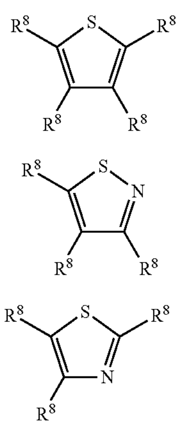

wherein, independently for each occurrence, $R^8$ is —H, —OH, —$OR^7$, —SH, —$SR^7$, $R^7$, halo, alkyl, aryl, heteroaryl, aralkyl, heteroaralkyl, —$SO_2$H, —$NHR^7$, or —NH—C(═O)—$R^7$;

$R^7$ is cycloalkyl, alkyl, or aryl or any two $R^7$, taken together, form a 5- or 6-membered ring;

the compound of formula VIII, formula IX, or formula X is

VIII

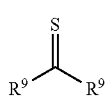

IX

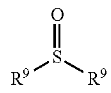

-continued

X

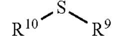

wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2$H, —$NH_2$, —$NHR^7$, or —NH—C(═O)—$R^7$;

$R^7$ is cycloalkyl, alkyl, or aryl, or any two $R^7$, taken together, form a 5- or 6-membered ring;

$R^{10}$ is hydroxyalkyl, $R^9$, or —$(CH_2)_x R^9$; and x is 1, 2, 3, or 4;

the compound of formula XI is

XI

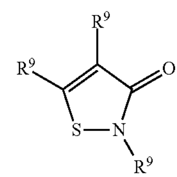

wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2$H, —$NH_2$, —$NHR^7$, or —NH—C(═O)—$R^7$; and $R^7$ is cycloalkyl, alkyl, or aryl, or any two $R^7$, taken together, form a 5- or 6-membered ring;

a native organism of the same species as the genetically engineered organism could not metabolize (i.e., use as a source of sulfur) the sulfur-containing compound; and the genetically engineered organism converts the substrate to a product.

In certain embodiments, the invention relates to a product made by any one of the aforementioned methods.

In certain embodiments, the invention relates to a recombinant vector comprising a gene operably linked to a promoter, wherein the gene encodes an enzyme; and the enzyme is NAD:phosphite oxidoreductase (phosphite dehydrogenase), glycerol-3-phosphate dehydrogenase (sn-glycerol 3-phosphate: NAD(+) oxidoreductase, EC 1.1.1.8) glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, or a NADH-FMN oxidoreductase.

BRIEF DESCRIPTION OF THE FIGURES

FIG. 1 depicts various DNA sequences of the invention (SEQ ID NOs:1-9, respectively in order of appearance).

FIG. 2 tabulates various organisms of the invention and exemplary potential applications.

FIG. 3 tabulates various organisms of the invention and exemplary potential applications.

FIG. 4 tabulates various organophosphorus compounds useful as feedstocks in the invention, and the chemical formula of each compound.

FIG. 5 tabulates various organosulfur compounds useful as feedstocks in the invention, and the chemical formula of each compound.

FIG. 9 tabulates the sequences of pNC273 (SEQ ID NOs:10-11, respectively in order of appearance).

FIG. 12 depicts the growth of NS435 with (a) phosphate (Pi), and (b) phosphite (Pt).

FIG. 14 depicts a plasmid map of pNC360.

FIG. 15 tabulates the sequence of pNC360 (SEQ ID NO:12-13, respectively in order of appearance).

FIG. 16 depicts growth of NS435 with different concentrations of hypophosphite.

FIG. 18 depicts a plasmid map of pNC351.

FIG. 19 tabulates the sequence of pNC351 (SEQ ID NO:14).

DETAILED DESCRIPTION OF THE INVENTION

Overview

Figure 6:
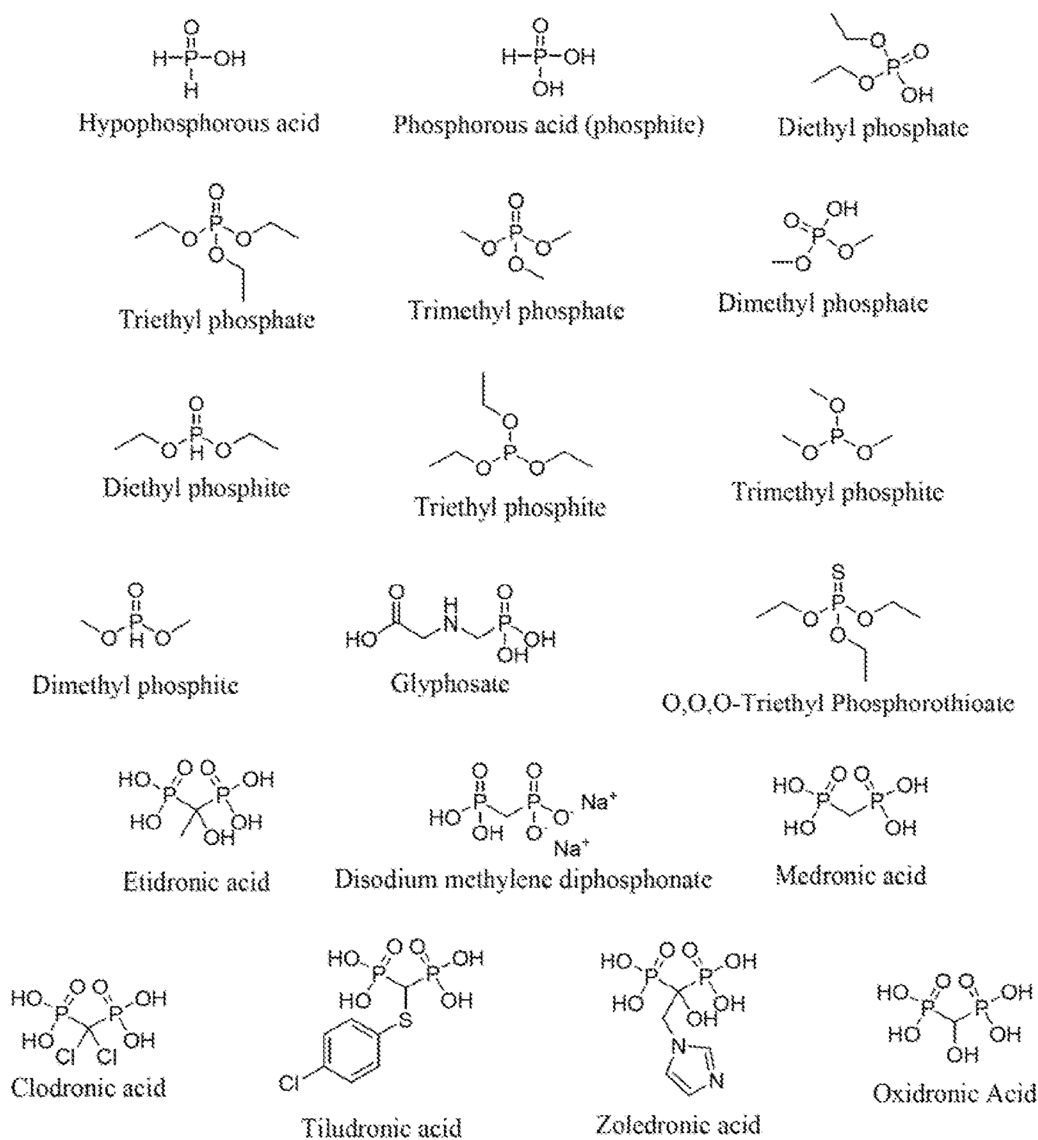
FIG. 6 depicts the names and structures of various organophosphorus compounds useful as feedstocks in the invention.
Figure 7:
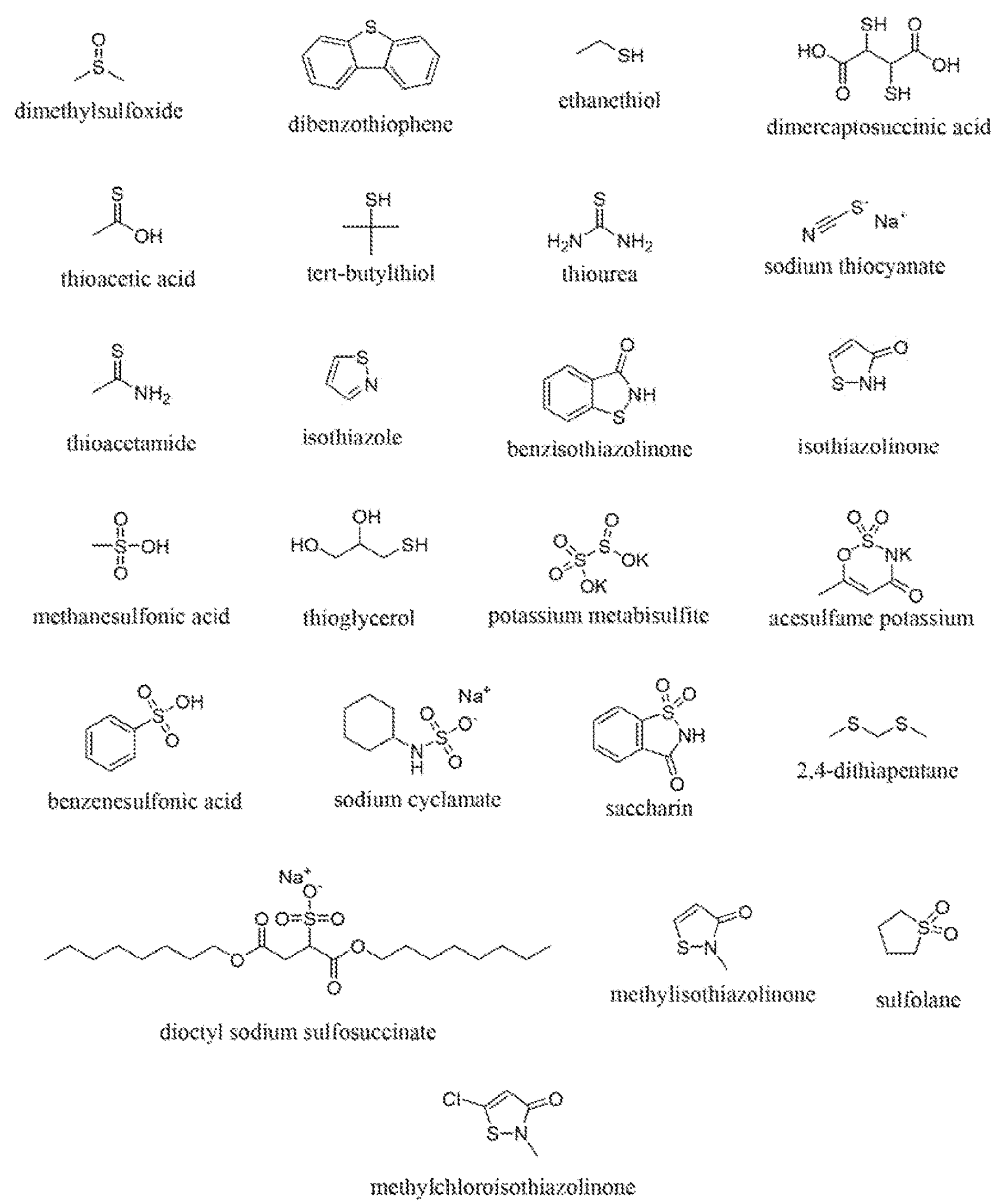
FIG. 7 depicts the names and structures of various organosulfur compounds useful as feedstocks in the invention.

In certain embodiments, the invention relates to a genetically engineered host organism, wherein the genetically engineered host organism has a non-native ability to obtain a growth-limiting nutrient from a complex substrate; and the complex substrate could not have been metabolized or used as a nutrient by the native host organism. In certain embodiments, the non-native ability will provide the organism with a significant competitive advantage, and provide a major barrier to the success of contaminants in a fermentation.

In certain embodiments, organisms generally contain only a small amount of phosphorus and sulfur (e.g., about 3% and about 1% by mass of the cell, respectively). So, in order to grow, organisms need less of these growth-limiting nutrients as compared to, for example, nitrogen.

In certain embodiments, the genetically engineered host organism is a bacterium, a yeast, a fungus, an algae, a mammalian cell, or an insect cell. In certain embodiments, the genetically engineered host organism is a bacterium or a yeast.

In certain embodiments, the invention relates to a method of using the above-mentioned genetically engineered host organism, comprising contacting the genetically engineered host organism with a modified cell culture medium. In certain embodiments, the invention relates to a method of using the above-mentioned genetically engineered host organism, comprising contacting the genetically engineered host organism with a modified cell culture medium, wherein the genetically engineered host organism converts the cell culture medium to a product. In certain embodiments, using this approach provides a unique and targeted manner to promote the growth of the desired genetically engineered host organism. In certain embodiments, the above-mentioned methods minimize the growth of contaminant organisms, provide a valuable competitive advantage, and allow management of production of a range of valuable products.

In certain embodiments, the inventive methods decrease or eliminate the need for use of prophylactic antibiotics in large scale yeast cultures. Avoiding unnecessary antibiotics is an important benefit due to emerging environmental considerations and societal pressures. Additionally, in certain embodiments, the technique can be applied to bacterial systems in which antibiotics may not be added. In certain embodiments, the technique can be applied to minimize the growth of wild yeast contaminants that are natively resistant to many commonly used antibiotics.

In certain embodiments, the genetically engineered host organism is a yeast; and the product is ethanol, isobutanol, lactic acid, succinic acid, erythritol, an isoprenoid, a lipid, and enzyme product, a bulk commodity chemical, or a high value specialty chemical.

In certain embodiments, the genetically engineered host organism is a bacterium; and the product is butanol, ethanol, isopropanol, 1,3-propanediol (PDO), 1,4-butanediol (BDO), succinic acid, itaconic acid, an enzyme product, a polyol, a protein product, a bulk commodity chemical, or a high value specialty chemical.

In certain embodiments, the inventive technology is applicable in the production of one or more commodities, fine chemicals, or pharmaceuticals.

Definitions

As used herein, the term "biomass" refers to a primarily carbohydrate-containing material. Biomass can also refer to a polysaccharide-containing material. It can also refer to a cellulose-, hemicellulose-, or lignocellulose-containing material. Biomass is commonly obtained from, for example, wood, plants, residue from agriculture or forestry, organic component of municipal and industrial wastes, primary sludges from paper manufacture, waste paper, waste wood (e.g., sawdust), agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphtha, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

"Exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Expression vector" or "expression construct" or "plasmid" or "recombinant DNA construct" is a vehicle for introducing a nucleic acid into a host cell. The nucleic acid can be one that has been generated via human intervention, including by recombinant means or direct chemical synthesis, with a series of specified nucleic acid elements that permit transcription and/or translation of a particular nucleic acid. The expression vector can be part of a plasmid, virus, or nucleic acid fragment, or other suitable vehicle. Typically, the expression vector includes a nucleic acid to be transcribed operably linked to a promoter.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Osmotic shock" is the rupture of cells in a solution following a sudden reduction in osmotic pressure. Osmotic shock is sometimes induced to release cellular components of such cells into a solution.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

"Promoter" is a nucleic acid control sequence that directs transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

"Recombinant" is a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vive cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Sonication" is a process of disrupting biological materials, such as a cell, by use of sound wave energy.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

Microbe Engineering

A. Overview

In certain embodiments of the invention, a microorganism is genetically modified to improve or provide de novo growth characteristics on a variety of feedstock materials.

Genes and gene products may be introduced into microbial host cells. Suitable host cells for expression of the genes and nucleic acid molecules are microbial hosts that can be found broadly within the fungal or bacterial families and which grow over a wide range of temperature, pH values, and solvent tolerances.

Microbial expression systems and expression vectors containing regulatory sequences that direct high level expression of foreign proteins are well known to those skilled in the art. Any of these could be used to construct chimeric genes to produce the any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and the aforementioned starting parent strain as a host can be transformed with the resulting plasmid. This approach can increase the copy number of each of the genes encoding the enzymes and, as a result, the activities of these enzymes can be increased. The plasmid is not particularly limited so long as it can autonomously replicate in the microorganism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202 (incorporated by reference)). Alternatively, elements can be generated synthetically using known methods (see for example Gene. 1995 Oct. 16; 164(1):49-53).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the host genome resulting in gene targeting, gene conversion, gene deletion, gene duplication, gene inversion and exchanging gene expression regulatory elements, such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

This subsection is divided into subsections. Subsection 1 describes control sequences typically contained on vectors as well as novel control sequences provided by the present invention. Subsection 2 describes genes typically contained in vectors as well as novel codon optimization methods and genes prepared using them provided by the invention.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microbe contains a coding sequence for a desired gene product (for example, a selectable marker, or an enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

The promoter used to express an exogenous gene can be the promoter naturally linked to that gene or can be a heterologous promoter.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of phosphorus or sulfur in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

D. Expression of Two or More Exogenous Genes

Further, a genetically engineered microorganism may comprise and express more than one exogenous gene. One or more genes can be expressed using an inducible promoter, which allows the relative timing of expression of these genes to be controlled. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second or further exogenous gene can be induced for a second period of time (during which expression of a first exogenous gene may or may not be induced). Provided herein are vectors and methods for engineering microbes to grow on non-traditional growth media.

E. Transformation

Cells can be transformed by any suitable technique including, e.g., biolistics, electroporation, glass bead transformation and silicon carbide whisker transformation. Any convenient technique for introducing a transgene into a microorganism can be employed in the present invention. Transformation can be achieved by, for example, the method of D. M. Morrison (Methods in Enzymology 68, 326 (1979)), the method by increasing permeability of recipient cells for DNA with calcium chloride (Mandel. M. and Higa, A., J. Mol. Biol., 53, 159 (1970)), or the like.

Examples of expression of transgenes in oleaginous yeast (e.g., *Yarrowia lipolytica*) can be found in the literature (see, for example, Bordes et al., J Microbiol Methods, Jun. 27 (2007)). Examples of expression of exogenous genes in bacteria such as *E. coli* are well known; see for example Molecular Cloning: A Laboratory Manual. Sambrook et al. (3d edition, 2001, Cold Spring Harbor Press).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to an endogenous promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (see for example Protist 2004 December; 155(4):381-93). The transformed cells can be optionally selected based upon the ability to grow in the presence of the antibiotic or other selectable marker under conditions in which cells lacking the resistance cassette would not grow.

Phosphorus-Containing Compounds in Feedstocks

In certain embodiments, the invention relates to use of an atypical phosphorus-containing feedstock comprising, consisting essentially of, or consisting of a phosphorus-containing compound of any one of Formulas I-III. In certain embodiments, a non-genetically engineered organism, i.e., a native organism, could not metabolize (i.e., use as a source of phosphorus) the phosphorus-containing compounds in the feedstock.

In certain embodiments, the invention relates to any one of the aforementioned phosphorus-containing feedstocks, wherein the phosphorus-containing compound is a compound of formula I or a salt thereof:

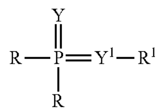

wherein, independently for each occurrence,

R is —H, alkyl, —OH, —$OR^2$, —SH, or —$SR^2$;

$R^1$ is —H, or alkyl;

Y is O or S;

$Y^1$ is O or S; and $R^2$ is alkyl.

In certain embodiments, the invention relates to any one of the aforementioned phosphorus-containing feedstocks, wherein the phosphorus-containing compound is a compound of formula II or a salt thereof:

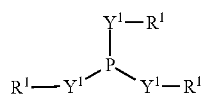

wherein, independently for each occurrence, $R^1$ is —H, or alkyl; and $Y^1$ is O or S.

In certain embodiments, the invention relates to any one of the aforementioned phosphorus-containing feedstocks, wherein the phosphorus-containing compound is a compound of formula III or a salt thereof:

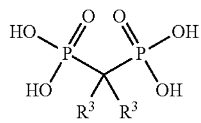

wherein, independently for each occurrence.

$R^3$ is —H, —OH, —$OR^4$, —SH, —$SR^4$, halo, alkyl, aryl, heteroaryl, aralkyl, or heteroaralkyl; and $R^4$ is alkyl or aryl.

In certain embodiments, the invention relates to any one of the aforementioned phosphorus-containing feedstocks, wherein the phosphorus-containing compound is selected from the group consisting of:

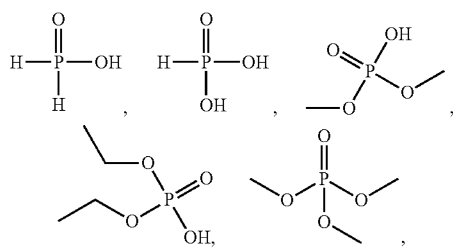

-continued

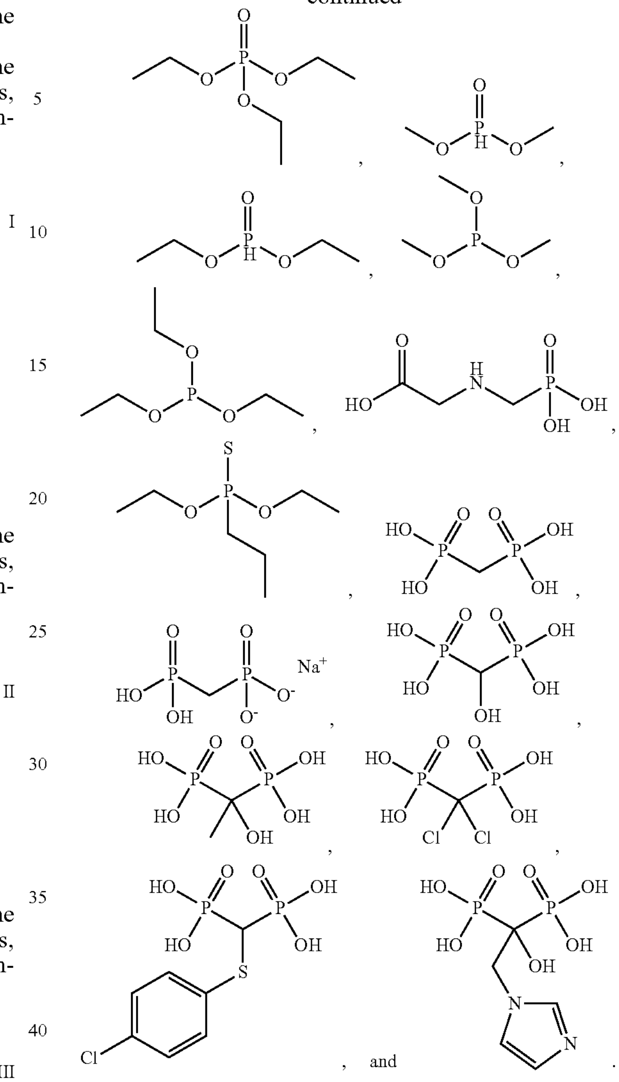

Sulfur-Containing Compounds in Feedstocks

In certain embodiments, the invention relates to use of an atypical sulfur-containing feedstock comprising, consisting essentially of, or consisting of a sulfur-containing compound of any one of Formulas IV-XI. In certain embodiments, a non-genetically engineered organism, i.e., a native organism, could not metabolize (i.e., use as a source of sulfur) the sulfur-containing compounds in the feedstock.

In certain embodiments, the invention relates to any one of the aforementioned sulfur-containing feedstocks, wherein the sulfur-containing compound is a compound of formula IV or a salt thereof:

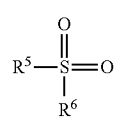

wherein, independently for each occurrence, $R^5$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(═O)—$R^7$;

$R^6$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(═O)—$R^7$; and $R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is a compound of formula V, formula VI, or formula VII, or a salt thereof:

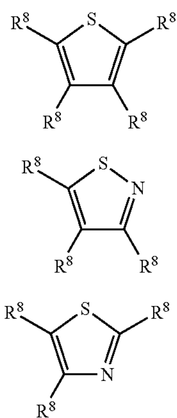

wherein, independently for each occurrence, $R^8$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(═O)—$R^7$;

$R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is a compound of formula VIII, formula IX, or formula X or a salt thereof:

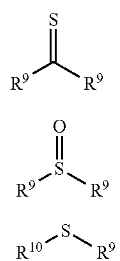

wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(═O)—$R^7$;

$R^7$ is cycloalkyl, alkyl, or aryl, or any two $R^7$, taken together, form a 5- or 6-membered ring;

$R^{10}$ is hydroxyalkyl. $R^9$, or —$(CH_2)_xR^9$; and x is 1, 2, 3, or 4.

In certain embodiments, the invention relates to any one of the aforementioned sulfur-containing feedstocks, wherein the sulfur-containing compound is a compound of formula XI or a salt thereof:

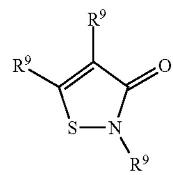

wherein, independently for each occurrence, $R^9$ is —H, —OH, —$OR^7$, —SH, —$SR^7$, $R^7$, halo, alkyl, aryl, heteroaryl, aralkyl, heteroaralkyl, —$SO_2H$, —$NH_2$, —$NHR^7$, or —NH—C(═O)—$R^7$; and $R^7$ is cycloalkyl, alkyl, or aryl, or any two $R^7$, taken together, form a 5- or 6-membered ring.

In certain embodiments, the invention relates to any one of the aforementioned sulfur-containing feedstocks, wherein the sulfur-containing compound is selected from the group consisting of:

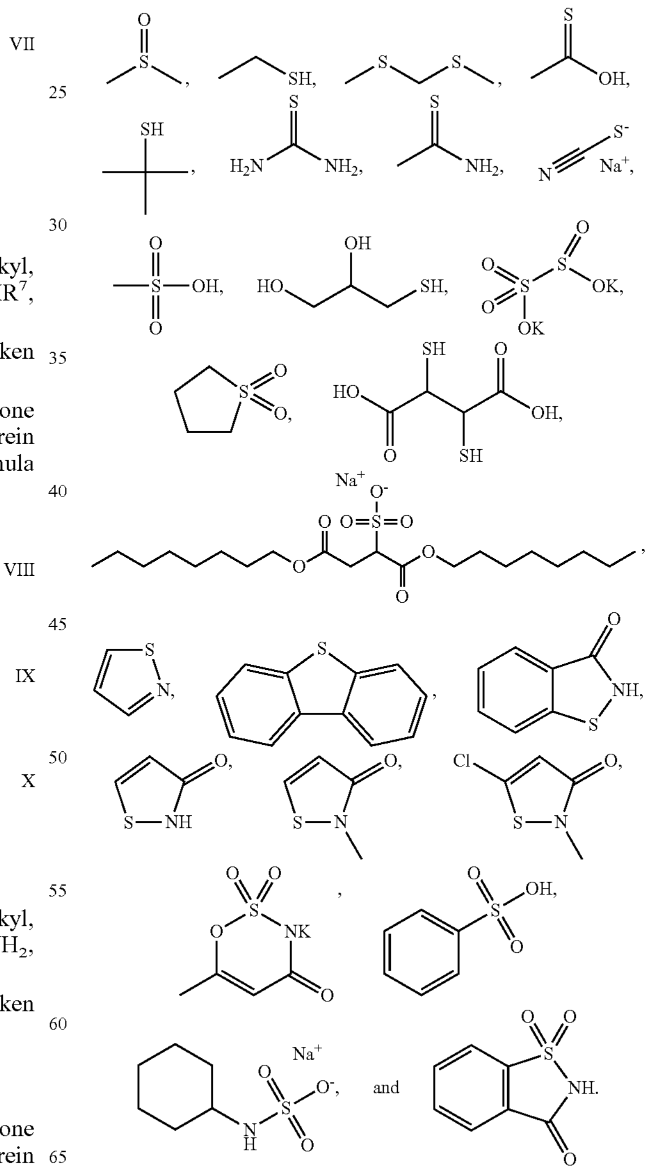

Exemplary Isolated Nucleic Acid Molecule and Vectors

In certain embodiments, the invention relates to an isolated nucleic acid molecule, wherein the nucleic acid molecule encodes an enzyme that provides the organism with the ability to assimilate a phosphorus source or a sulfur source that otherwise would not have been accessible to the native organism; and the enzyme is NAD:phosphite oxidoreductase (phosphite dehydrogenase), glycerol-3-phosphate dehydrogenase (sn-glycerol 3-phosphate: NAD(+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, or a NADH-FMN oxidoreductase.

In certain embodiments, the invention relates to an isolated nucleic acid molecule, wherein the nucleic acid molecule is selected from the group consisting of *Delftia acidoorans* phosphodiesterase pdeA, *Enterobacter aerogenes* updABDE gpdQ, *Flavobacterium* opdA without periplasmic leader sequence, *Pseudomonas aeruginosa* PAO1 phoA, *Pseudomonas monteilii* C11 hocA, *Pseudomonas stutzeri* WM88 htxABCDEFHGLIKLMN, *Pseudomonas stutzeri* WM88 ptxABCDE, *Rhodococcus* dszD, and *Rhodcoccus* dszABC.

In certain embodiments, the invention relates to an isolated nucleic acid molecule comprising any one of the sequences disclosed herein. In certain embodiments, the invention relates to an isolated nucleic acid molecule having at least 85% sequence homology with any one of the sequences disclosed herein. In certain embodiments, the invention relates to an isolated nucleic acid molecule having at least 90% sequence homology with any one of the sequences disclosed herein. In certain embodiments, the invention relates to an isolated nucleic acid molecule having at least 95% sequence homology with any one of the sequences disclosed herein. In certain embodiments, the invention relates to an isolated nucleic acid molecule having at least 99% sequence homology with any one of the sequences disclosed herein. In certain embodiments, the invention relates to an isolated nucleic acid molecule having any one of the sequences disclosed herein.

A recombinant vector comprising any one of the aforementioned nucleic acid molecules operably linked to a promoter.

In certain embodiments, the invention relates to a recombinant vector comprising any one of the sequences disclosed herein. In certain embodiments, the invention relates to a recombinant vector having at least 85% sequence homology with any one of the sequences disclosed herein. In certain embodiments, the invention relates to a recombinant vector having at least 90% sequence homology with any one of the sequences disclosed herein. In certain embodiments, the invention relates to a recombinant vector having at least 95% sequence homology with any one of the sequences disclosed herein. In certain embodiments, the invention relates to a recombinant vector having at least 99% sequence homology with any one of the sequences disclosed herein.

Exemplary Genetically Engineered Organisms of the Invention

In certain embodiments, the invention relates to a genetically engineered organism, wherein the genetically engineered organism has been transformed by a nucleic acid molecule or a recombinant vector comprising any one of the sequences disclosed herein. In certain embodiments, the nucleic acid molecule or recombinant vector has at least 85% sequence homology with any one of the sequences disclosed herein. In certain embodiments, the nucleic acid molecule or recombinant vector has at least 90% sequence homology with any one of the sequences disclosed herein. In certain embodiments, the nucleic acid molecule or recombinant vector has at least 95% sequence homology with any one of the sequences disclosed herein. In certain embodiments, the nucleic acid molecule or recombinant vector has at least 99% sequence homology with any one of the sequences disclosed herein. In certain embodiments, the invention relates to a genetically engineered organism, wherein the genetically engineered organism has been transformed by a nucleic acid molecule or a recombinant vector having any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of NAD:phosphite oxidoreductase (phosphite dehydrogenase), glycerol-3-phosphate dehydrogenase (sn-glycerol 3-phosphate: NAD (+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, and a NADH-FMN oxidoreductase.

In certain embodiments, the invention relates to any one of the aforementioned genetically engineered organisms, wherein the non-native gene is selected from the group consisting of dzABC, dszA, dszABCD, dszB, dszC, dszD, gpdQ, hocA, htxA, htxABCDLEFHGIJKLMN, htxB, htxC, htxD, htxE, htxF, htxG, htxH, htxI, htxJ, htxK, htxL, htxM, htxN, opdA, ophA, pde, pdeA, phoA, ptxABCDE, ptxD, ugpA, ugpAECB, ugpB, ugpC, ugE, updA, updABDE, updB, updD, and updE.

Any organism may be used as a source of the non-native gene, as long as the organisms has the desired enzymatic activity The non-native gene can each be obtained from chromosomal DNA of any one of the aforementioned microorganisms by isolating a DNA fragment complementing auxotrophy of a variant strain lacking the enzymatic activity. Alternatively, if the nucleotide sequence of these gene of the organism has already been elucidated (Biochemistry, Vol. 22, pp. 5243-5249, 1983; J. Biochem. Vol. 95, pp. 909-916, 1984; Gene, Vol. 27, pp. 193-199, 1984; Microbiology, Vol. 140, pp. 1817-1828, 1994; Mol. Gene Genet. Vol. 218, pp. 330-339, 1989; and Molecular Microbiology, Vol. 6, pp 317-326, 1992), the genes can be obtained by PCR using primers synthesized based on each of the elucidated nucleotide sequences, and the chromosome DNA as a template.

In certain embodiments, the invention relates to any one of the aforementioned genetically engineered organisms, wherein the non-native gene is selected from the group consisting of *Delftia acidoorans* phosphodiesterase pdeA, *Enterobacter aerogenes* updABDE gpdQ, *Flavobacterium* opdA without periplasmic leader sequence, *Pseudomonas aeruginosa* PAO1 phoA, *Pseudomonas monteilii* C11 hocA, *Pseudomonas stutzeri* WM88 htxABCDEFHGIJKLMN, *Pseudomonas stutzeri* WM88 ptxABCDE, *Rhodococcus* dszD, and *Rhodococcus* dszABC.

In certain embodiments, the invention relates to any one of the aforementioned genetically engineered organisms, wherein the genetically engineered organism is a species of the genus *Acetobacter, Acinetobacter, Alcaligenes, Arxula, Aspergillus, Aurantichytrium, Bacillus, Candida, Chlamy-*

*domonas, Clostridium, Corynebacterium, Escherichia, Hansenula, Isochrysis, Kluyveromyces, Lactococcus, Micrococcus, Nannochloropsis, Ogataea, Paracoccus, Pavlova, Penicillium, Pichia, Pseudomonas, Rhizopus, Rhodosporidium, Rhodotorula, Saccharomyces, Schizosaccharomyces. Streptococcus, Streptomyces, Synechococcus, Tetraselmis, Thermoanaerobacter, Thermoanaerobacterium, Trichoderma, Xanthaomonas*, or *Yarrowia.*

In certain embodiments, the invention relates to any one of the aforementioned genetically engineered organisms, wherein the genetically engineered organism is a species of the genus *Aspergillus, Bacillus, Chlamydomonas, Corynebacterium, Escherichia, Hansenula, Kluyveromyces, Saccharomyces, Synechococcus*, or *Yarrowia.*

In certain embodiments, the invention relates to any one of the aforementioned genetically engineered organisms, wherein the genetically engineered organism is selected from the group consisting of *Acetobacter, Acinetobacter calcoaceticus, Alcaligenes eutropha, Arxula adeninivorans, Aspergillus nidulans, Aspergillus niger, Aspergillus orzyae, Aspergillus terreus, Aurantiochytrium* spp., *Bacillus licheniforms, Bacillus methanolicus, Bacillus stearothermophilus, Bacillus subtilis, Candida utilis, Chlamydomonas reinhardtii, Clostridium acetobutylicum, Clostridium thermocellum, Corynebacterium glutamicum, Escherichia coli, Hansenula polymorpha, Isochrysis* spp., *Kluyveromyces lactis, Kluyveromyces marxianus, Lactococcus lactis, Micrococcus lysodeikticus, Nannochloropsis* spp., *Ogataea, Paracoccus denitrificans, Pavlova* spp., *Penicillium chrysogenum, Pichia guilliermondii, Pichia pastoris, Pichia stipitis, Pseudomonas putida, Rhizopus* spp., *Rhodoporidium* spp., *Rhodotorula* spp., *Saccharomyces cerevisiae, Schizosaccharomyces pombe, Streptococcus lactis, Streptomyces, Synechococcus elongatus, Tetraselmis* spp., *Thermoanaerobacter* spp., *Thermoanaerobacterium* spp., *Trichoderma reesei, Xanthaomonas campestris*, or *Yarrowia lipolytica.*

In certain embodiments, the invention relates to any one of the aforementioned genetically engineered organisms, wherein the genetically engineered organism is selected from the group consisting of *Aspergillus niger, Bacillus subtilis, Chlamydomonas reinhardtii, Corynebacterium glutamicum, Escherichia coli, Hansenula polymorpha, Kluyveromyces marxianus, Saccharomyces cerevisiae, Synechococcus elongatus*, or *Yarrowia lipolytica.*

Exemplary Methods of the Invention

In certain embodiments, the invention relates to a method, comprising the step of contacting any one of the aforementioned genetically engineered organisms with a substrate, wherein the substrate comprises a phosphorus-containing fraction and a non-phosphorus-containing fraction:

the phosphorus-containing fraction comprises, in an amount from about 10% by weight to about 100% by weight, a phosphorus-containing compound of any one of Formulas I-III;

a native organism of the same species as the genetically engineered organism could not metabolize (i.e., use as a source of phosphorus) the phosphorus-containing compound; and the genetically engineered organism converts the substrate to a product.

In certain embodiments, the invention relates to any one of the aforementioned methods, wherein the phosphorus-containing compounds have a low molecular weight. In certain embodiments, the invention relates to any one of the aforementioned methods, wherein the phosphorus-containing compounds have a molecular weight between about 30 Da and about 800 Da. In certain embodiments, the invention relates to any one of the aforementioned methods, wherein the phosphorus-containing compounds have a molecular weight between about 40 Da and about 600 Da. In certain embodiments, the invention relates to any one of the aforementioned methods, wherein the phosphorus-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the phosphorus-containing compounds have less than 12 carbon atoms. In certain embodiments, the invention relates to any one of the aforementioned methods, wherein the phosphorus-containing compounds have less than 8 carbon atoms. In certain embodiments, the invention relates to any one of the aforementioned methods, wherein the phosphorus-containing compounds have 1, 2, 3, 4, 5, 6, or 7 carbon atoms.

In certain embodiments, the invention relates to any one of the aforementioned methods, wherein the phosphorus-containing compounds are between about 8% and about 75% phosphorus by weight. In certain embodiments, the invention relates to any one of the aforementioned methods, wherein the phosphorus-containing compounds are between about 15% and about 47% phosphorus by weight. In certain embodiments, the invention relates to any one of the aforementioned methods, wherein the phosphorus-containing compounds are about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, or about 74% phosphorus by weight.

In certain embodiments, the invention relates to any one of the aforementioned methods, wherein the phosphorus-containing compounds have an octanol-water partition coefficient (log P) less than about 5. In certain embodiments, the invention relates to any one of the aforementioned methods, wherein the phosphorus-containing compounds have an octanol-water partition coefficient (log P) from about −0.5 to about 5. In certain embodiments, the invention relates to any one of the aforementioned methods, wherein the phosphorus-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the phosphorus-containing compounds are soluble in water at about 20° C. at a concentration of between about 0.01 g/L to about 1000 g/L. In certain embodiments, the invention relates to any one of the aforementioned methods, wherein the phosphorus-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the phosphorus-containing compounds move through the cell membrane by passive transport. Passive transport includes diffusion, facilitated diffusion, and filtration.

In certain embodiments, the invention relates to any one of the aforementioned methods, wherein the phosphorus-containing compounds move through the cell membrane by active transport, such as, for example, via an ATP-Binding Cassette (ABC) transporter or other known transmembrane transporter.

In certain embodiments, the invention relates to any one of the aforementioned methods, wherein the phosphorus-containing compounds are transported through the cell membrane.

In certain embodiments, the invention relates to any one of the aforementioned methods, wherein the phosphorus-containing compounds are substantially non-biocidal.

In certain embodiments, the invention relates to any one of the aforementioned methods, wherein the phosphorus-containing compounds are substantially biodegradable.

In certain embodiments, the invention relates to any one of the aforementioned methods, wherein the phosphorus-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction comprises, in an amount from about 10% by weight to about 100% by weight, a phosphorus-containing compound selected from the group consisting of:

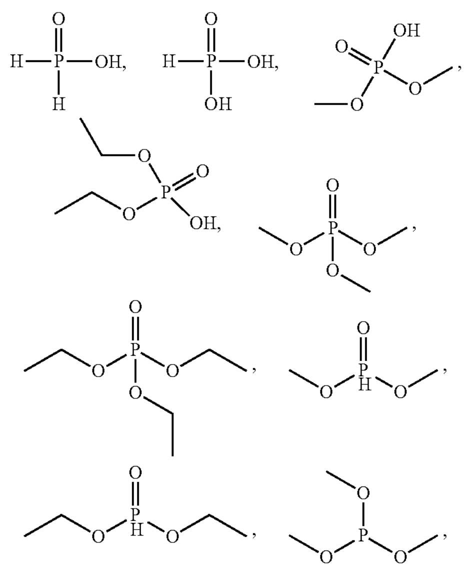

-continued

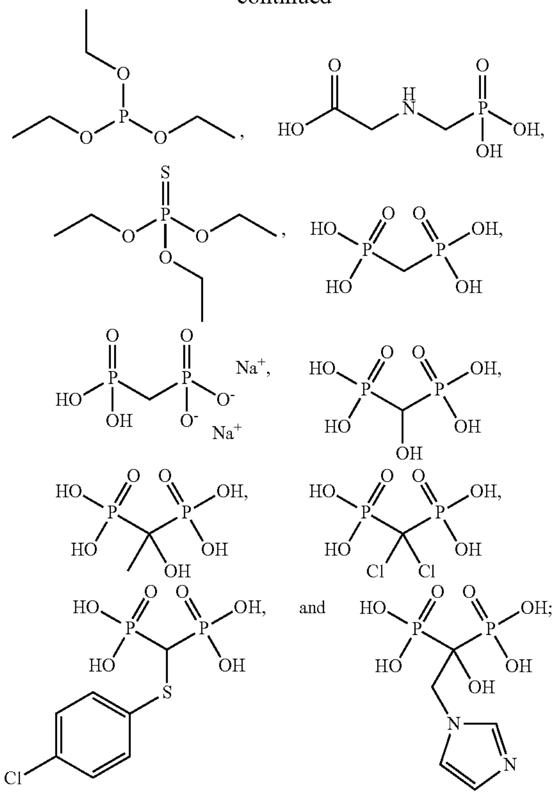

and the genetically engineered organism converts the substrate to a product.

In certain embodiments, the invention relates to any one of the aforementioned methods, wherein the phosphorus-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a phosphorus-containing fraction and a non-phosphorus-containing fraction;

the phosphorus-containing fraction consists essentially of a phosphorus-containing compound selected from the group consisting of -continued

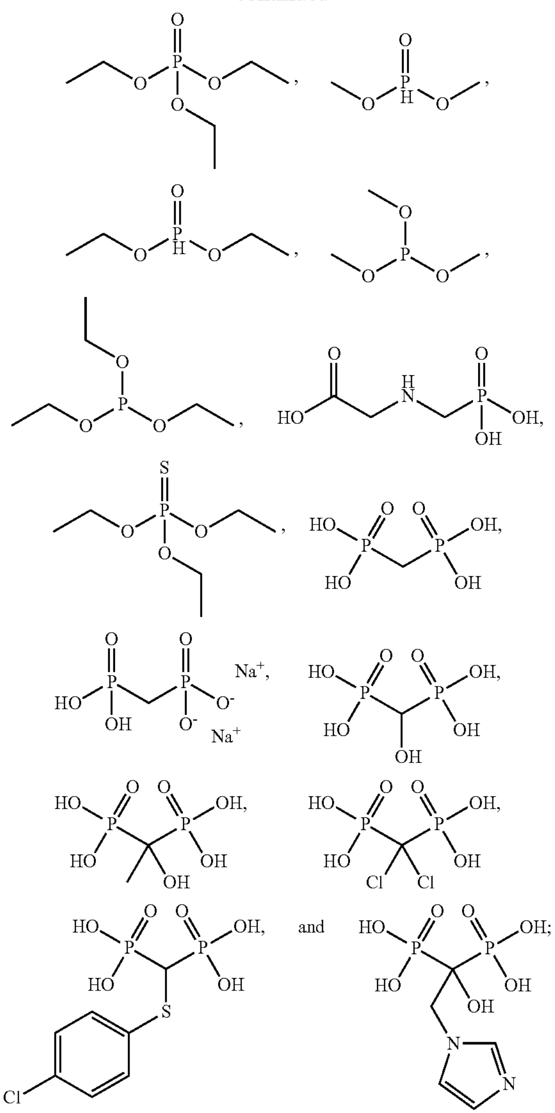

and the genetically engineered organism converts the substrate to a product.

In certain embodiments, the invention relates to a method comprising the step of contacting any one of the aforementioned genetically engineered organisms with a substrate, wherein the substrate consists of a phosphorus-containing fraction and a non-phosphorus-containing fraction;

the phosphorus-containing fraction consists of a phosphorus-containing compound selected from the group consisting of

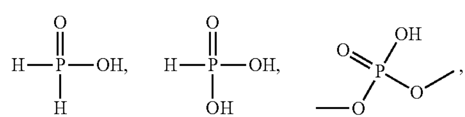

-continued and the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein a non-genetically engineered organism, i.e., a native organism, could not metabolize (i.e., use as a source of phosphorus) the phosphorus-containing compound.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction comprises, in an amount from about 10% by weight to about 100% by weight, a sulfur-containing compound of any one of Formulas IV-XI;

a native organism of the same species as the genetically engineered organism could not metabolize (i.e., use as a source of sulfur) the sulfur-containing compound; and the genetically engineered organism converts the substrate to a product.

In certain embodiments, the invention relates to any one of the aforementioned methods, wherein the sulfur-containing compounds have a low molecular weight. In certain embodiments, the invention relates to any one of the aforementioned methods, wherein the sulfur-containing compounds have a molecular weight between about 30 Da and about 800 Da. In certain embodiments, the invention relates to any one of the aforementioned methods, wherein the sulfur-containing compounds have a molecular weight between about 40 Da and about 600 Da. In certain embodiments, the invention relates to any one of the aforementioned methods, wherein the sulfur-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the sulfur-containing compounds have less than 12 carbon atoms. In certain embodiments, the invention relates to any one of the aforementioned methods, wherein the sulfur-containing compounds have less than 8 carbon atoms. In certain embodiments, the invention relates to any one of the aforementioned methods, wherein the sulfur-containing compounds have 1, 2, 3, 4, 5, 6, or 7 carbon atoms.

In certain embodiments, the invention relates to any one of the aforementioned methods, wherein the sulfur-containing compounds have an octanol-water partition coefficient (log P) less than about 5. In certain embodiments, the invention relates to any one of the aforementioned methods, wherein the sulfur-containing compounds have an octanol-water partition coefficient (log P) from about −0.5 to about 5. In certain embodiments, the invention relates to any one of the aforementioned methods, wherein the sulfur-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the sulfur-containing compounds are soluble in water at about 20° C. at a concentration of between about 0.01 g/L to about 1000 g/L. In certain embodiments, the invention relates to any one of the aforementioned methods, wherein the sulfur-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the sulfur-containing compounds move through the cell membrane by passive transport. Passive transport includes diffusion, facilitated diffusion, and filtration.

In certain embodiments, the invention relates to any one of the aforementioned methods, wherein the sulfur-containing compounds move through the cell membrane by active transport, such as, for example, via an ATP-Binding Cassette (ABC) transporter or other known transmembrane transporter.

In certain embodiments, the invention relates to any one of the aforementioned methods, wherein the sulfur-containing compounds are transported through the cell membrane.

In certain embodiments, the invention relates to any one of the aforementioned methods, wherein the sulfur-containing compounds are substantially non-biocidal.

In certain embodiments, the invention relates to any one of the aforementioned methods, wherein the sulfur-containing compounds are substantially biodegradable.

In certain embodiments, the invention relates to any one of the aforementioned methods, wherein the sulfur-containing fraction comprises the phosphorus-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a sulfur-containing fraction and a non-phosphorus-containing fraction;

the sulfur-containing fraction comprises, in an amount from about 10% by weight to about 100% by weight, a sulfur-containing compound selected from the group consisting of:

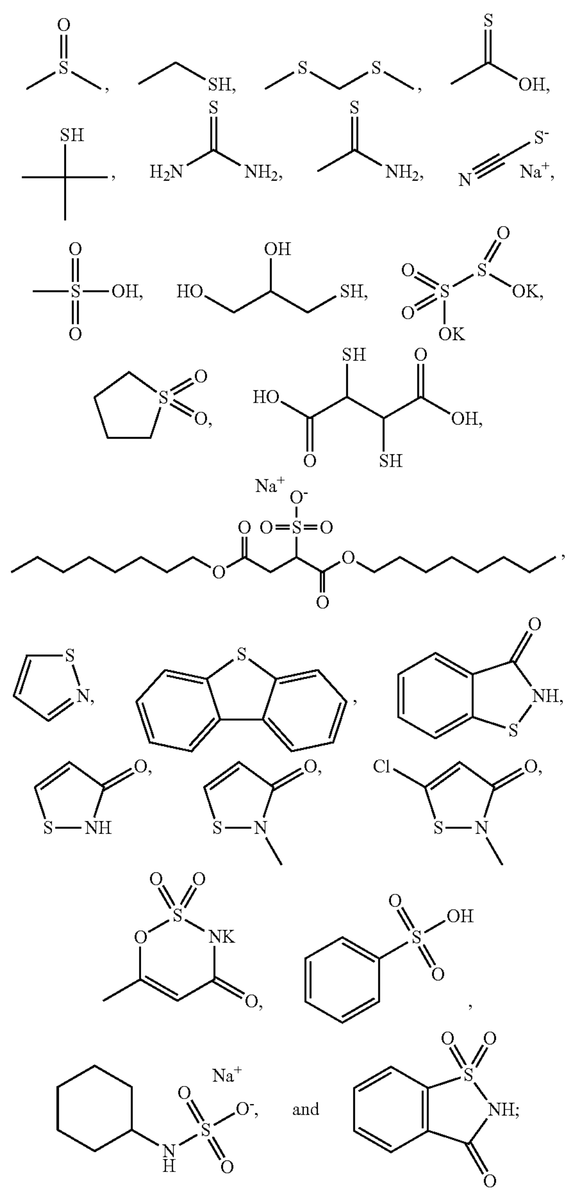

and the genetically engineered organism converts the substrate to a product.

In certain embodiments, the invention relates to any one of the aforementioned methods, wherein the sulfur-containing fraction comprises the sulfur-containing compound in about 10%, about 15%, about 20%, about 25%, about 30%, about 35%, about 40%, about 45%, about 50%, about 55%, about 60%, about 65%, about 70%, about 75%, about 80%, about 85%, about 95%, about 95%, or about 100% by weight.

In certain embodiments, the invention relates to a method, comprising the step of contacting any one of the aforementioned genetically engineered organisms with a substrate, wherein the substrate comprises a sulfur-containing fraction and a non-sulfur-containing fraction;

the sulfur-containing fraction consists essentially of a sulfur-containing compound selected from the group consisting of

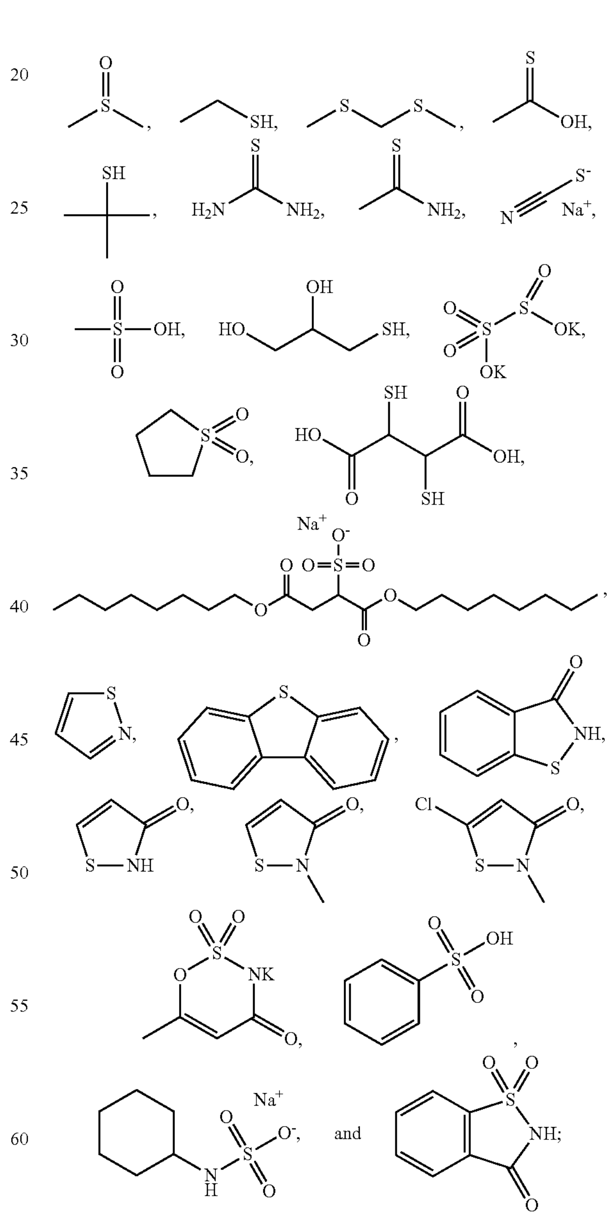

and the genetically engineered organism converts the substrate to a product.

In certain embodiments, the invention relates to a method comprising the step of contacting any one of the aforementioned genetically engineered organisms with a substrate, wherein the substrate consists of a sulfur-containing fraction and a non-sulfur-containing fraction;

the sulfur-containing fraction consists of a sulfur-containing compound selected from the group consisting of

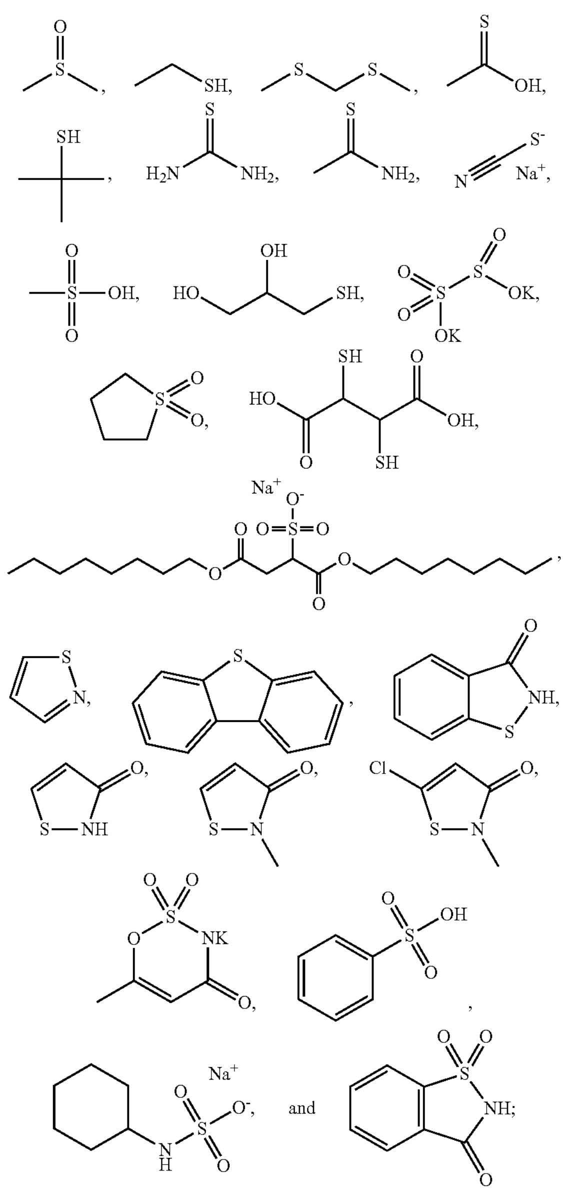

and the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein a non-genetically engineered organism, i.e., a native organism, could not metabolize (i.e., use as a source of sulfur) the sulfur-containing compound.

In certain embodiments, the invention relates to any one of the aforementioned methods, wherein the substrate comprises lignoccllulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

Exemplary Products

In certain embodiments, the invention relates to a product made by any one of the aforementioned methods.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

Use of Phosphite as Phosphorus Source for ptxD-Expressing *Yarrowia lipolytica*

A) Expression of Bacterial ptxD in *Yarrowia lipolytica*

Figure 8:
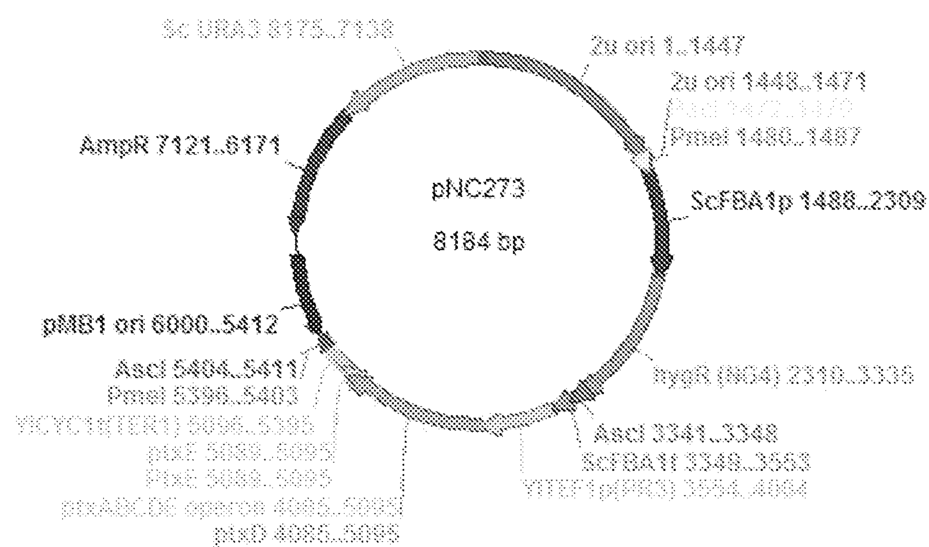
FIG. 8 depicts a plasmid map of vector pNC273, which was used to construct strain NS392.

Vector pNC273 was used to construct strain NS392. See FIG. 8.

Vector pNC273 was restriction digested with enzyme PmeI, and the linear fragment containing hygR and ptxD under control of the 1*Y. lipolytica* TEF1 promoter and *Y. lipolytica* CYC1 terminator. Transformation was via standard protocols (Chen D. C. et al., Appl Microbiol Biotechnol. 1997 August; 48(2):232-5). See FIG. 9.

B) Competition experiment between ptxD-expressing *Y. lipolytica* and wildtype *S. cerevisiae*

Figure 10:
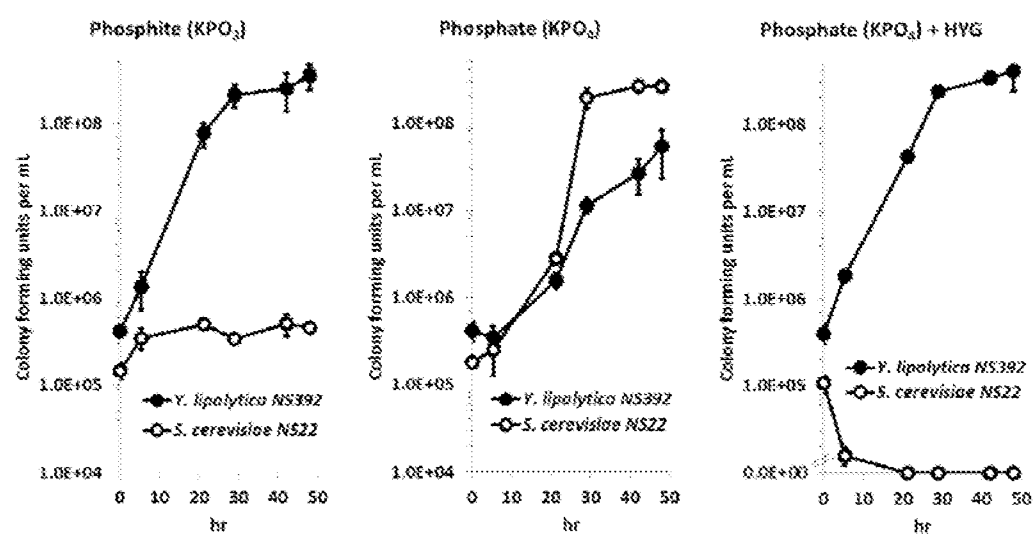
FIG. 10 depicts the growth of two organisms (modified *Y. lipolytica* NS392 (solid circles) and wild-type *S. cerevisiae* NS22 (open circles)) on three different growth media: potassium phosphite as the sole phosphorus source (left), potassium phosphate as the sole phosphorus source (middle), and potassium phosphate plus hygromyic as a control condition.

*Yarrowia lipolytica* NS392 (ptxD $HYG^R$) and *Saccharomyces cerevisiae* NS22 (wildtype, $HYG^S$) were pre-cultured overnight in defined medium with 10 mM potassium phosphate (NS22) or 10 mM potassium phosphite (NS392). After pre-culture growth, cells were washed twice in water and added to three experimental media conditions at an $OD_{600nm}$ of 0.06 for NS22 and 0.6 for NS392. The three media conditions were with potassium phosphite as sole phosphorus source, potassium phosphate as sole phosphorus source, and with potassium phosphate plus hygromycin as a control condition to select to $HYG^R$ *Y. lipolytica* and against $HYG^S$ *S. cerevisiae*. See FIG. 10.

Defined Media Composition

| Macro nutrients | g/L |
|---|---|
| Glucose monohydrate | 44 |
| Urea | 3 |
| $MgSO_4 \cdot 7H_2O$ | 0.5 |
| Potassium hydrogen phthalate | 1 |
| Disodium phthalate | 4.25 |
| **Vitamins** | **mg/L** |
| Biotin | 0.05 |
| Thiamine | 1.0 |
| D-Pantothenic acid | 1.0 |
| Nicotinic acid | 1.0 |
| myo-inositol | 25 |
| Pyridoxine | 1.0 |
| p-Aminobenzoic acid | 0.2 |
| **Micro elements** | **mg/L** |
| EDTA | 15 |
| $CaCl_2 \cdot 6H_2O$ | 7.5 |
| $(NH_4)_2FeSO_4 \cdot 6H_2O$ | 3.0 |
| $CuSO_4 \cdot 5H_2O$ | 0.2 |
| $ZnSO_4 \cdot 7H_2O$ | 1.0 |
| $MnSO_4 \cdot H_2O$ | 0.5 |
| $Na_2MoO_4 \cdot 2H_2O$ | 0.2 |
| **To this base medium, add either** | **g/L** |
| $KH_2PO_4$ | 1.3 |
| $KH_2PO_3$ | 1.2 |

Example 2

Use of Hypophosphite as Phosphorus Source for ptxD-expressing *Yarrowia lipolytica*

*Y. lipolytica* expressing ptxD also grows on hypophosphite. As shown in Table 1. NS18, wildtype *Y. lipolytica*, does not grow on phosphite or hypophosphite, and neither does NS184, a *Y. lipolytica* strain engineered for increased lipid production. NS324 (created by transforming NS18 with pNC273) and NS392 (created by transforming NS184 with pNC273) are able to grow on both phosphite and hypophosphite. However, *E. coli* W3110, which has the native ability to convert phosphite to phosphate, is unable to grow on hypophosphite. Additionally, W3110 was unable to grow on hypophosphite pre-incubated in defined yeast medium, suggesting that hypophosphite is not degraded to phosphite by incubation in medium alone. Additional measurements of growth with phosphate, phosphite, and hypophosphite are shown below in Table 2 for strain NS324.

TABLE 1

| Phosphate Source | NS18 | NS184 | NS324 (ptxD) | NS392 (ptxD) | W3110 |
|---|---|---|---|---|---|
| 0 Phosphate | – | – | – | – | – |
| 10 mM Phosphate | + | + | + | + | + |
| 10 mM Phosphite | – | – | + | + | + |
| 10 mM Hypophosphite | – | – | + | + | – |

TABLE 2

| NS324/phosphate source | 0 hr $OD_{600}$ | 19 hr $OD_{600}$ | 28 hr $OD_{600}$ | 44 hr $OD_{600}$ |
|---|---|---|---|---|
| 0 Pi | 0.021 | 0.034 | 0.00 | 0.001 |
| 0.2 Mm Pi | 0.021 | 0.812 | 4.68 | 6.86 |
| 2 mM Pi | 0.021 | 0.736 | 4.92 | 5.04 |
| 20 mM Pi | 0.021 | 0.804 | 5.50 | 5.98 |
| 0.2 mM Pt | 0.021 | 0.704 | 2.71 | 5.43 |
| 0.4 mM Pt | 0.023 | 0.568 | 2.57 | 5.01 |
| 1 mM Pt | 0.023 | 0.7 | 3.77 | 6.2 |
| 2 mM Pt | 0.022 | 0.568 | 3.08 | 5.9 |
| 4 mM Pt | 0.023 | 0.68 | 3.23 | 4.45 |
| 10 mM Pt | 0.023 | 0.696 | 2.94 | 4.36 |
| 20 mM Pt | 0.023 | 0.840 | 3.69 | 5.24 |
| 0.2 mM Hpt | 0.021 | 0.008 | 0.21 | 0.454 |
| 0.4 mM Hpt | 0.021 | 0.04 | 0.71 | 0.732 |
| 1 mM Hpt | 0.021 | 0.24 | 1.13 | 1.66 |
| 2 mM Hpt | 0.023 | 0.712 | 1.96 | 2.99 |
| 4 mM Hpt | 0.023 | 0.896 | 3.24 | 5.36 |
| 10 mM Hpt | 0.023 | 0.632 | 2.17 | 3.17 |
| 20 mM Hpt | 0.022 | 0.452 | 1.26 | 1.72 |

Example 3

Use of Phosphite as Phosphorus Source for ptxD-expressing *Saccharomyces cerevisiae*

Figure 11:
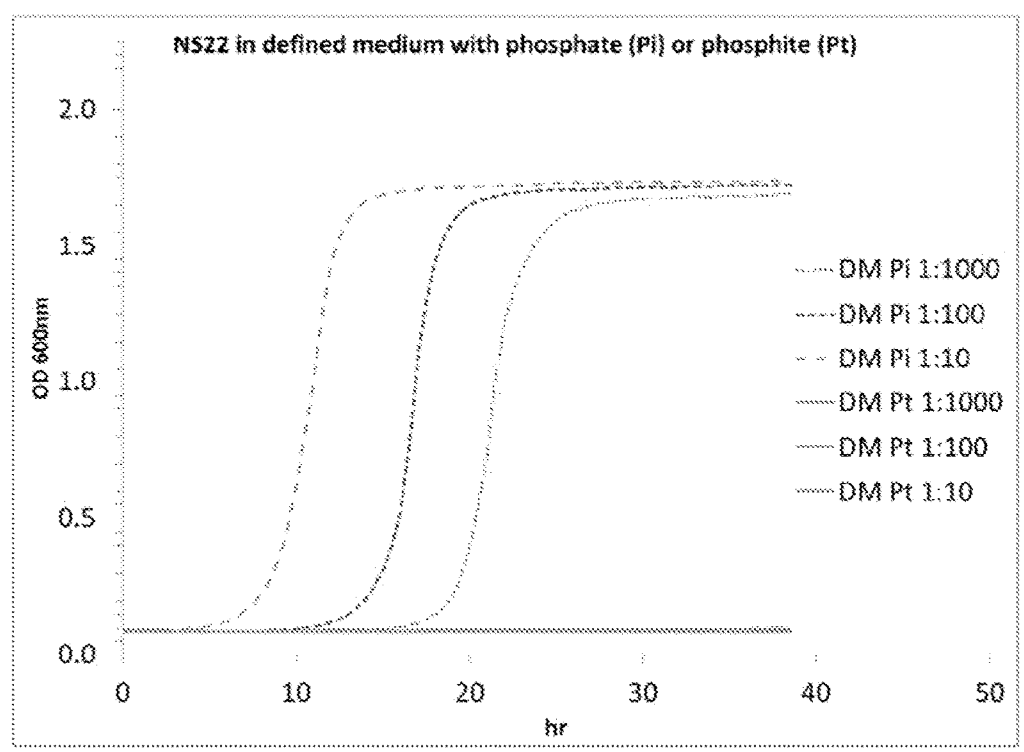
FIG. 11 depicts the growth of NS22, wildtype *S. cerevisiae*, with phosphate or phosphite as phosphorus source in defined medium. Different 10-fold serial dilutions of the inocula were made to observe the possible occurrence of a lag phase.
Figure 13:
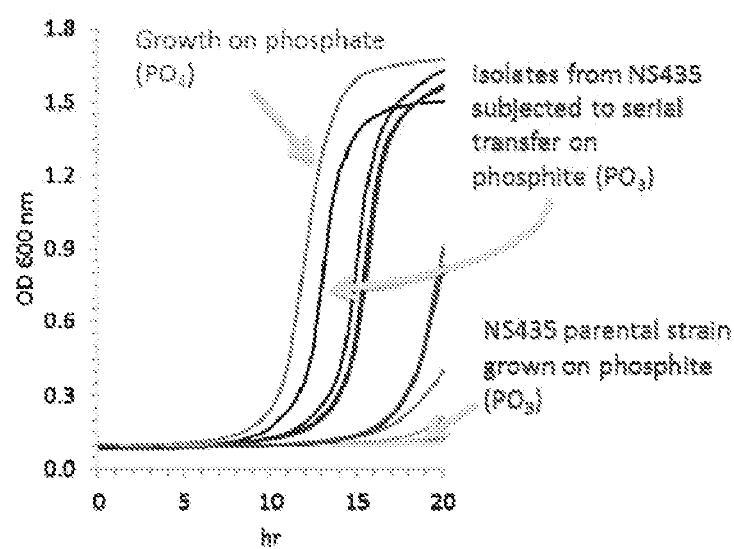
FIG. 13 depicts the growth of isolates after serial transfer of NS435 in phosphite media.
Figure 17:
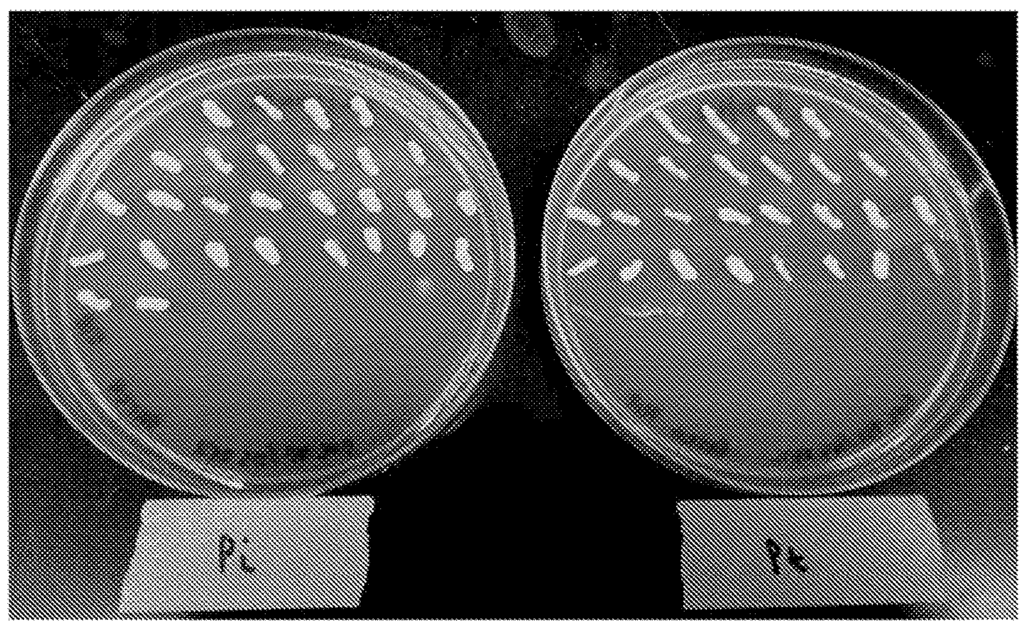
FIG. 17 depicts NS252+ptxD transformants patched on defined medium agar plates with phosphate (Pi, left) or phosphite (Pt, right) as phosphorus source. Untransformed NS252 was also patched.

Wildtype *S. cerevisiae* was shown to not grow with phosphite supplied as phosphorus source (FIG. 11). Plasmid pNC273, containing ptxD under control of the *Y. lipolytica* TEF1 promoter, was transformed into *S. cerevisiae* NS22. Despite evidence of functional ptxD expression in *Y. lipolytica* with the same vector, and prior evidence of *Y. lipolytica* TEF1 promoter function in *S. cerevisiae* expressing an antibiotic resistance marker, no growth was seen with this transformed construct with phosphite as phosphorus source. Subsequently, ptxD was placed under control of the *S. cerevisiae* TEF1 promoter in vector pNC360. With this transformed strain, NS435, growth was observed with phosphite as phosphorus source, although a lag phase was present. (FIG. 12). To reduce the lag phase, NS435 was serial transferred 10 times in 5 mL defined medium with 1 mM potassium phosphite replacing potassium phosphate. Serial transfers were performed after cultures reached stationary phase, with approximately 70 generations occurring during the transfers. From the final serial passage whole culture was streaked to single colonies on phosphite containing solid agar medium. Several of these isolates were grown in defined medium with 1 mM phosphate, washed, and evaluated in medium with 10 mM phosphite for growth rate and lag phase (FIG. 13). Of these, a top performing isolate was retained and designated NS473.

Example 4

Use of Hypophosphite as Phosphorus Source for ptxD-expressing *Saccharomyces cerevisiae*

*S. cerevisiae* functionally expressing ptxD also surprisingly grows on hypophosphite. As shown in Table 3, NS22, wildtype *S. cerevisiae*, does not grow on phosphite or hypophosphite. NS435 (created by transforming NS22 with pNC360) is able to grow on both phosphite and hypophosphite. However, *E. coli* W3110, which has the native ability to convert phosphite to phosphate, is unable to grow on hypophosphite. Additionally, W3110 was unable to grow on hypophosphite pre-incubated in defined yeast medium, suggesting that hypophosphite is not degraded to phosphite by incubation in medium alone. Additional measurements of growth with hypophosphite are shown below in FIG. 16 for strain NS435.

TABLE 3

| Phosphate Source | NS22 | NS435(ptxD) | W3110 |
|---|---|---|---|
| 0 Phosphate | – | – | – |
| 10 mM Phosphate | + | + | + |
| 10 mM Phosphite | – | + | + |
| 10 mM Hypophosphite | – | + | – |

Example 5

Use of Phosphite as Phosphorus Source for ptxD-expressing *Arxula adeninivorans*

*A. adeninivorans* strain NS252, a wildtype strain, was transformed with plasmid pNC351, containing the ptxD gene under control of the *A. adeninivorans* PGK1 promoter. Transformation was performed with an electrotransformation protocol with selection on defined medium plates with 1 mM potassium phosphite as phosphorus source (see below). Colonies grew on plates spread with cells from the NS252+pNC351 transformation, and 25 of these colonies were patched onto phosphate and phosphite defined media agar plates, and evaluated for the presence of ptxD via colony PCR. 24 of the 25 the putative transformants were positive for ptxD by colony PCR, and 25 of 25 displayed rapid growth on phosphite plates.

*Arxula adeninivorans* Transformation Protocol

1. Inoculate 5 mL of YPD media in a 14-mL culture tube with *A. adeninivorans* strain NS252 from a YPD plate and put it in the 37° C. drum roller for overnight incubation.
2. Add about 2.5 mL of the overnight liquid culture into a 250-mL flask containing 22.5 mL of fresh YPD and incubate in the 37° C. shaker for 3.5-4 hrs.
3. Centrifuge the culture at 3000 rpm for 3 mins. Discard the supernatant, wash the cells with water followed by centrifugation and discard the supernatant again.
4. To the cell pellet, add 2 mL of 100 mM lithium acetate solution and 40 μL of 2 M dithiothreitol. Transfer into an Eppendorf tube.
5. Tape the tube on the 37° C. wheel and let it incubate for an hour.
6. Centrifuge at 1000 rpm for 10 seconds, discard the supernatant.
7. Wash cells with 1 mL water, and mix by gentle pipetting.
8. Centrifuge, discard supernatant, wash with cold 1M sorbitol, mix by pipetting, centrifuge, discard supernatant.
9. Add 2 mL of cold 1 M sorbitol to cell pellet, place it on ice.
10. Into the pre-chilled 0.2-cm electroporation cuvettes, add 40 μL of the cells and 5 μL of DNA to be transformed, ideally at >100 μg/mL DNA concentration.
11. Electroporate at 25 μF, 200 ohms, 1.5 kV, ~4.9-5.0 ms time constant.
12. Recover transformed cells using 1 mL YPD at 37° C. overnight.
13. Plate 100 μL-500 μL of the recovered culture onto appropriate selective plates, and incubate at 30° C. or 37° C. until colony formation.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A genetically engineered yeast organism wherein the genetically engineered organism has been transformed by a nucleic acid molecule; the nucleic acid molecule comprises a non-native gene comprising ptxD; and the non-native gene encodes for a non-native enzyme comprising NAD:phosphite oxidoreductase (phosphite dehydrogenase).

2. The genetically engineered organism of claim 1, wherein the non-native gene comprises *Pseudomonas stutzeri* WM88 ptxD.

3. The genetically engineered yeast organism of claim 1, wherein the genetically engineered organism is a species of the genus *Yarrowia, Saccharomyces*, or *Arxula*.

4. The genetically engineered organism of claim 1, wherein the genetically engineered organism is selected from the group consisting of *Yarrowia lipolytica, Saccharomyces cerevisiae*, and *Arxula adeninivorans*.

5. A genetically engineered yeast organism of the genus *Yarrowia, Saccharomyces, or Arxula*, wherein the genetically engineered organism has been transformed by a nucleic acid molecule comprising SEQ ID NO:11.

6. A genetically engineered organism, wherein the genetically engineered organism has been transformed by a nucleic acid molecule; the nucleic acid molecule comprises a non-native gene; and the non-native gene encodes for a non-native NAD:phosphite oxidoreductase (phosphite dehydrogenase) enzyme comprising SEQ ID NO:10.

* * * * *

SEQUENCE LISTING

```
<160> NUMBER OF SEQ ID NOS: 14

<210> SEQ ID NO 1
<211> LENGTH: 4127
<212> TYPE: DNA
<213> ORGANISM: Pseudomonas stutzeri

<400> SEQUENCE: 1

atgacgcccc atccgataca ggacgccgtg ctgcgggtcg accggttgag cgtcgtctat     60

ccaggcggcg tgacagccct acgcgatacc tcgattgcat ttcggcgtgg tgagttcacc    120

gtgctgcttg gtctctcggg cgcaggcaag tcgaccttgc tccgtagtct caatcgactc    180

gtcacgccca ctggcggcag tgtcaccagc gaactcggtg aactcggcag cggctcggcc    240

ttgcgtcagc atcgtcggcg taccgccatg atctttcagc accaccagct aatcgaacgt    300
```

```
caaagcgcac tggctaatgt gctgaccggt cggctggcct ttcacaacac gctccgctcg    360
ctgtttcctc tgccgcgtgc cgatcaggag attgcgctca gttgcctcgc tcgggtcggt    420
ctggcagaca aggcgctaag ccgggtggac aaactgtccg gtggccagca gcagcgggta    480
ggcatcgcgc gtgcgctagc gcaacagccg gcgatcattc tggccgatga gccggtagcc    540
agtctcgacc cggccacttc ggtccgtgtt ctcggattgc tgcgcgacat ctgcaaggaa    600
gacggcatca ccgccatcgt ttcgctgcat caactcgaat atgcccgccg cttcgccgat    660
cgcgtcgtcg ggctggccga ttctcagatc gttttcgatg ccgcgccctc ggaactcacc    720
gatgcgcagc ttgagcgcat ctatgcaggc cgctctacga ctcagccagc gaatgctccg    780
gctgaaccac ctgtcatgct cgaaccttca ctggagatgt cccgatgaaa cgcttatccg    840
cgctcttatt gacttgcttg ctgtccgctg tttcaagttt gtccgcccta gcggccgatg    900
ccgatccgga tgtgctaaag gttgccctgc tgccggacga aaacgcctcc gagctgatca    960
agcgtaacca gccgctgaag gattatctgg aagagcatct ggacaagaag gtgcagctga   1020
tcgtaaccac cgactattcc tcgatgattg aggcgatgcg ctttggccgt atcgacctgg   1080
cgtatttcgg tccgctgtcc tacgtcatgg ccaaaagcaa aagcgacatc gagcccttcg   1140
ctgccatggt catcgacggc aagccgacct atcgctcggt gattatcgcc aatgtggcgt   1200
caggcgtgaa tgagtatgcc gaccttaagg gcaagagaat ggcctatggt gaccgggcat   1260
cgacgtccag ccatttgatt cccaaaaccg tgcttcttga gacggccgat ttgacgggtg   1320
ggcaggacta cgaacaacat tttgtgggca cgcatgacgc cgttgccgtc aacgtggcga   1380
acggcaacgc cgatgcgggt gggctgtcgg aggtaatttt caatcacgca gccgaacgtg   1440
gcctgatcga tccgagcaag gtgaaagtac ttggttacag cggcgaatac cccccagtacc   1500
cctgggcgat gcgctcgaac ctgagccccg agctgaaaac caaggtgcgg gatgtattcg   1560
tcggtatcga cgatcccgaa gtgctgcgca acttcaaggc cgaggccttc gcgccaatca   1620
ccgacgccga ctacgatgtg atccgcaaca tgggatcgct gctcggcctc gacttcgcca   1680
cgatgtgagc accgatatgt cttctcatta cgacgtgcag gcgctgcctg cagagcaacg   1740
cgagcacatc cttcgaggct tcggcctcgg ttggtggcgc cagctggggc aggtggcgat   1800
tgtattcgga gtggtgctgt tggcctgctg gtacgtgggg ctgctcgatg ccaccacgct   1860
gctgaacggg ctgccctcca tcgcgaccct ggcaggcgag gccatgccgc cagacttttc   1920
gggctatcga agctggattc gccccttgat cgacaccttg gcgatgagca tcgccggtac   1980
ggccatcgca gtggtgttct cgctggtggt ggccttcgtt gcagcgcgca atacggcgcc   2040
gcaccccctt gtgttcggtg ttgcccgggt gctgctcaat gccctgcggt cggtgccgga   2100
gctgatcatg ggcatcatct tcgttgcagc cgtagggttc ggcgccttgc cgggcgtgct   2160
tgccctgggt ctgcattcgg tcggcatggt cggcaagttc ttcgccgagg ccatcgagca   2220
cgtcgacgaa gcgccggtgg aagccgctcg ggcggcgggg gctacgccga tgcaagtgct   2280
gctgcacgcg gttttgccac aggtgacgcc gcagttcgcc gacgtggcga tctaccgctg   2340
ggaatacaac tttcgcgcct ccaccgtgat gggcatggtt ggcgccggcg gtatcggctt   2400
cgaactcatg ggctcgctgc gcatcatgca gtaccaggag gttgcagcaa tcctgctggt   2460
catcctggcc atggtcacgc tagtagacgc cttcagtggc gtgctgcgca aacatttcaa   2520
ataggacaaa ccatgctgcc gaaactcgtt ataactcacc gagtacacga tgagatcctg   2580
caactgctgg cgccacattg cgagctgatg accaaccaga ccgacagcac gctgacgcgc   2640
```

```
gaggaaattc tgcgccgctg tcgcgatgct caggcgatga tggcgttcat gcccgatcgg   2700
gtcgatgcag actttcttca agcctgccct gagctgcgtg tagtcggctg cgcgctcaag   2760
ggcttcgaca atttcgatgt ggacgcctgt actgcccgcg gggtctggct gaccttcgtg   2820
cctgatctgt tgacggtccc gactgccgag ctggcgatcg gactggcggt ggggctgggg   2880
cggcatctgc gggcagcaga tgcgttcgtc cgctctggcg agttccaggg ctggcaacca   2940
cagttctacg gcacggggct ggataacgct acggtcggca tccttggcat gggcgccatc   3000
ggactggcca tggctgatcg cttgcaggga tggggcgcga ccctgcagta ccacgaggcg   3060
aaggctctgg atacacaaac cgagcaacgg ctcggcctgc gccaggtggc gtgcagcgaa   3120
ctcttcgcca gctcggactt catcctgctg gcgcttccct tgaatgccga tacccagcat   3180
ctggtcaacg ccgagctgct tgccctcgta cggccgggcg ctctgcttgt aaacccctgt   3240
cgtggttcgg tagtggatga agccgccgtg ctcgcggcgc ttgagcgagg ccagctcggc   3300
gggtatgcgg cggatgtatt cgaaatggaa gactgggctc gcgcggaccg gccgcggctg   3360
atcgatcctg cgctgctcgc gcatccgaat acgctgttca ctccgcacat agggtcggca   3420
gtgcgcgcgg tgcgcctgga gattgaacgt tgtgcagcgc agaacatcat ccaggtattg   3480
gcaggtgcgc gcccaatcaa cgctgcgaac cgtctgccca aggccgagcc tgccgcatgt   3540
tgaatccggt ctggctgaag agcctggtag cgatcgttca aacaggcagt tttcagagcg   3600
cggcgagggc gttggggctg gcccagccga cggtgtcgca gcacttgcag aagcttgaag   3660
agcaggtcgg cgtaacgctg gtgcagcgca gtcgtagcgg ctgccagcct accacacggg   3720
cgctggcctt catgccgcat gcgaccgcct tgctcgacat gcacgcccgg gcgctagaag   3780
ccctgcatgg caatcgtgag cgcgtcgggg ccagctccaa catcggcacc taccttctcc   3840
agccattcgt gcgcaactat ctgacgaccg caaatgagag gggcgaggtg gatctgcgca   3900
tcgccgccaa cccggatgtg gccgaccagc tactggcggg ccagctcgac gccgcgatca   3960
tggaatggtg gctacctcac cccgacttcg aataccgcct ctggcgggtc gagccgctgg   4020
tgcttatcgt cagccccgac catgcgctgg ctgaagcagg gtgcatagaa cgtgatcgtc   4080
tggtggacct gccgatgctg ggaggtgaac cgggtagcgg tacctag                 4127
```

<210> SEQ ID NO 2
<211> LENGTH: 13771
<212> TYPE: DNA
<213> ORGANISM: Pseudomonas stutzeri

<400> SEQUENCE: 2

```
atgtttgcag agcagcaacg cgaatatctc gacaagggat atacgaagat tgaaagcttt     60
ttctccgcgg aggaagtagc gaagattctt gaagacgtca agcaaattga attgggagct    120
attggcgtag cttcggacaa tgagacttac cagttcgaaa agaagaatgg cgagacgacg    180
aagctactgc gtcgcgtcga gaatcctcac ctttatttcg atgcaataga ttctttggtc    240
aggtcggaaa aaatcgtcga tttgcttcgg catttcctgg gcgaaaacat ccgtttgcac    300
aatagcaaaa tcaacttcaa gccgccatca ggcgcgccag tccagtggca tcaggactgg    360
gcattctatc cccacacaaa cgatgatttt cttactctcg gaattttcct cgacgagaca    420
agtgagaaaa atggcgcgat ggcatgcttg ccaggctccc acaaaggaaa agtgtacgac    480
caccggaacg tcgagacggg cgagttttgc cacgcgatct ctcgctccaa ctgggacgaa    540
gcgctcgacc cgacagaagg ggagttactg acgggacccg taggaactgt cacgttgcat    600
cacgtccgga cccttcatgg ttcaggccca aaccactcaa cgatcaggcg gcgttttctg    660
```

```
ctcatcggct atgccgcggc tgatgcctgg ccacttctgg gctgtggcaa ctatggggat    720
tatgaaagcc tcatggtctc tggccgatcc accgtattcc cgcgcatggt ggaactccct    780
ttgactgtcc cgtatccgtt gtcgatgtac ggtgatcgca tctttgaaag tcaacgagct    840
ttgactcaaa agtactactg aagtctttaa ctcactgagg tcataatgca agtttttact    900
ctgttttcga aattcaagaa ggcgttaacg cgcgccattc ttgcctttat cgccacaatc    960
atagtgtgca cacccgcgca ggcagctgag gttgtcaatg gtaaacttca cctgcgtttt   1020
gcaattgcgc cgatgcgtcc aacgcctagc cagaccatca aagagtttga gccgatattc   1080
aagtatctcg ccgaccagct cggcgcgacc tatgaaatcg tctccccgga aagctgggcg   1140
gcaatatctg tggcaatgac aaatggccat gtcgatgtgg gctggctcgg accctggggc   1200
tatgtcttgt cgaataaaaa ggccggcacc gaagtgcttg caacggtcaa gtaccgcggg   1260
gagccgttct acaaagccct cattgtcggt cgcgccgatc tgccgatcaa aaaatggccc   1320
gaggacgcga agggtttgaa gctgtcactc agtgatcagg gcaacacttc tggctggctc   1380
atcccgatgg cgtacttcaa gagcatcggc atcgaccctg cgagctattt tgaatatcgt   1440
gaaggtgcca cgtttggcca gaacgaatca cagattcagc acggactgat cgacctcgga   1500
tccgatatgg atcggggccg gaacgggatg atcgaagcgg gtcaaatcga tccttcgaag   1560
tccaagatcg tgtgggaatc cagcaagctg ccgaacgacg cgatatccgt gccgaaggat   1620
tttgatcctg ctctgaaagc gcgcatcacg gaaatactga cgtccttgtc cgaagagaaa   1680
gcacagtcgc tgatgggctc gggctataac ggcttcgtga aggcaaagca cagcgattac   1740
aaggtaatcg aagacgccgg ccgcatcctg ggaaaactgt aaagcacgag ggtccgttc    1800
ttggatgagg gcagcggacg acaaggtgga ctgacgcacg ccagctcctt gtctccgctg   1860
cacgaacata cgggcgcgca tcgcaatacc acagaggatg aaccaatgaa tcagcgaatc   1920
gaagaagtca tgctggctaa tgtcaagagg gacgtagcca ggagaaagcg gcattttgca   1980
acgtcggtcg tagtactcag tttgctggca gtggcctggt acgtgtgtca gatagaattc   2040
cagaagctag gcgccggttt accgagacta tggtcattcg tcgtgcagat gtttccaccc   2100
gacctgagcg acctggacgt cattctaaaa ggggctggcg agacgctcgc catggcgacg   2160
attggcacga tattcgccac aatcattgca tttccgctgg cactcatggc tgcgcgtaat   2220
acctgtccga acaagtggac ctatcgggta tcccgcgcca tcctgaacgc cagccgcggc   2280
acggagacat ttgtctatgc acttgtattt gtagcagcag tgggcttcgg tccgttctcc   2340
ggcgtactgg ccattacttt ccacatggta ggggcaatcg gcaaaatgtt tgctgaagcc   2400
atcgagcccg ttgaccaagg gccgttggat gcgctcgcct tgaccggtgc cagcagggca   2460
aagattatcc gctacggtct gatcccggat gttatgccgc acctgatcgc gagcgttcta   2520
tacatttggg aattcagtgt cagaacgtcc acagtactgg gcatcgtagg cgcaggtgga   2580
attgggcaga ccctgaaaga tactgtggac ttgttggaat tcaacaagat gattacggta   2640
ctggcggttg tattgctgat ggtgtcggca atcgatttca tcagtgaccg gctcaggtac   2700
ttgatattgg acacaaaacg cgagggattc gaaactctcc ctgcgaataa ctgattgctt   2760
cacgtattac tggaagggag gttcgcaatg aaagatgtag cgttgcagtt aaagaatgtc   2820
ggtaagtcat acggcaataa agttgtcctg gaatcgattg acttcgaagt acgtcacggc   2880
tcaatggttg ccttgctcgg cacaagcggg gcagggaagt cgacgctttt ccgatgtctc   2940
actggccttg agccgattga ctccggttct atcgtggcgc tcggagaatc catacatgaa   3000
```

```
ctgtctccgg cgcgtctgcg ggcagtacgt ggccagatcg ggttcgtgtt ccaacaactg   3060
cacctggtga aaaggttctc agcactcgag aatgtattgg gtgcgcgtct ggcagagatg   3120
cccatttggc gcgtcacatt gaaaagcttc agccgggctg acaaagtgct cgcgttcgaa   3180
tgtctggacc gggtcggcat gctcgattat gcaaacacgc ctacgcaact gctgtcaggc   3240
ggtcagcaac agcgtattgc gatagcgcga gccttggcgc agaagcccaa gattattatt   3300
gcggacgaac ccgtctccag cctcgatccg ctgacggcgc gctcggttct gcaaacgctg   3360
aaagccgcgg ctacagatct taatgtcgcg gtcctgtgca gcctgcacca ggtagacctg   3420
gcccgtgagt ttggcgaccg catcgtgggc atgcgcgacg gacgtgtcgt tttcgacggc   3480
acgccagcgg aattcaccga cgagcgcgtg catgcgcttt accaggtgcc cgctgggaag   3540
atgcaccagc ggccgagagc gacgcgcagc actcggtggc cggtctggct gtggcatgag   3600
gggcgaagcg atgaccacat ccacacgccc catacccgtg ccgcccccagg gcaccgcact   3660
gcactggcac ctgagcgcgc cctacaacgc caaacatctg ctggtgctga tcgccgtcat   3720
ggtgctgttg ttcgtgaccg gacaacgcac cgaaatggac cgcatggtgg ccatgacggc   3780
acaggccgtg gccaagaccg tgggcctggc tgacgattca caagtcgcgc gcggcttgtc   3840
gcgcgtcggt caagccatgt ggccacccgc catcgcagaa accgaagagg tgggccggat   3900
tcaggacctg gatcgccaga agctgcccct gttctcgcac atcgagaccc aggagcgcgt   3960
cgagcagaag atgaatctgg acacgctgaa gatggaagcc acgacggaaa ccgtcgaagt   4020
gctggtcaag ccggtcggct atgtctggac ggttttcatc aagatgatcg agacctggag   4080
attgcgctgt ggggcacgat cctgtcggtg ctggtgtcga ttcccctggc gtatttcgcg   4140
gcccgcaact actagcccca accgttttac ctacaccgct gcccgcggca ccatcagtct   4200
gctgcgttca gcgccggaac tcatcgtcgc tttgttcctg gtgctggcct acggctttgg   4260
ccccatcgct ggcgtgctgg cgctgggcct gcatgcggcc ggcttcctgg gcaagttcta   4320
cgccgaggac atcgagaacg ccgacaagaa gccgcaagag gcgctggagg ccatcggcgc   4380
gggcaagctc aagacgctgt ggtacggcgt catcccccag gtcttgccgc aatacatcgc   4440
ctacaccgcc tacatcctgg accgcaacct gcgcatggcc accgtcatcg gtctggtggg   4500
cgcgggcggc atcggccagg aactcaaggg ccgttttgac atgttccagt acggccatgt   4560
catgaccatc ctgatcgcga tcttcgtctt tgtgttcgtg ctggaccagt tgcaggcgcg   4620
catccgcgcc aagctgatct gaggcgaccg ctgacaacaa ggaacaacat gacaaacact   4680
tctgaagcac cggatcgtgc gcagtggctg cggctgtggt cggccttgcc ggccgcagcg   4740
gtcaaggccc tggcggccga tctggcgggc cagcaccggg tcgaagacct ggcgttgccg   4800
caatccggtc tgggcctgct gccgctgacc gacagcgccc tgggcgatac ctatttcatc   4860
ggtgagattc ccttggcaca agcgcatgtg cgggtcacga ccacccaagg gcagtcgatc   4920
gaaggcgcgg ccattctggt ggacgaccgt gccggtgtgg cccgttccat ggccatcctg   4980
gacgcggtgc tggcggcccg catgccaggt tgtgaagcgg ccctgcggtt gctcacccag   5040
ggtgcgaccg ccgtggcgga acaaggccgc cagcgccgcg ccttactcgc ggccacgcgg   5100
gtggactttg ccctgctggg aacgaacgag gaggacgatg atgaatgaga ctgggatggc   5160
ggcggcaccg gcagaagccg cgtggcgcat ctggcaagcg ccgcgccagc aaacggcgtt   5220
tcgccagttg atgaccgcgt tttcctatcc gggccgcgtg gtgccactgg ccgatggcgc   5280
tgaatcggcg ctcctgctgg tgttgaccac cctggtggac agcgcctgtg cgctggccga   5340
tccgctgcac gcgctatcaa gcgacgatct gcgccgactg ggcgtgcgct cggccagtgt   5400
```

```
ggaggcggcc gagttcgtgc tggccgatgg caaccgtttg ctggaggcca cgccgcgcct   5460
gggatcgctg gaaaaccccg aacaaggcgc gaccgtggtg atgcgcgtct cccgtttcgg   5520
tgagggtccc catctgcggc tcaccgggcc gggtattcaa cacgagcagg tgctgcaggt   5580
cagcggcatc gatccgggct ggtggaagca acggtccgaa tggaatgccc acttcccgct   5640
gggcgtggac ctgattctgg tgagcgggca cgaggtcgcg gtattgcccc gaaccaccca   5700
catcaacctc aaaggagccc actgatggga tacgttgcca tcaagggcgg tggccgggcc   5760
atcgccggtg ccgaagccgc cgtcgaagcc ctgcgctgcg ccgaagggcc agcgggtacg   5820
ccgctcacgc tgtcggccat cgaacagcag ttgcggttgc tgacatcgcg cgtcgtgtcg   5880
gaagggggcc tctaccaccc acgcctggcc gctctggcca tcaaacagat gcagggcgac   5940
acactggaag cggcgttcgc tctgcgcgcc taccgctcca ccaagccacg cctgatggat   6000
gtgccggtgc aggacacgag ccgcatgcgc ctaatccgcc ggatttcgag cgctttcaag   6060
gacatccccg gcggacagat gctgggcccg accaccgact acgcgctgcg cctgatgcgt   6120
ctggatttgg ccaacgagtc gcccgaggac tttcgcgcgg tctcgcggcg gtttctggac   6180
agcgtggccg acaccgacct gcccgacagc ttccccaagg tggtcgatgc cttgcgtgac   6240
gaaggcttgc tgccgccgct gacccggcgc gcccatgcgg cgttcgacat cacccgcgac   6300
ccgctggttt tcccagtgcc gcgttcggcg gccctggcca ccatggcacg cgccgaaacc   6360
ggctcgctct tggcgattgc gtattccaac atgcgtggct atggcgacgt gcaccccacc   6420
atcgccgagc tgcgcgtggg ctatgtgccg gtgatgctgc cgcacccggt gacaggcgag   6480
cccatcgaag ccggtgaggt actgatgacc gaatgcgaag tggtggccat gtttgagggt   6540
gatgctaccg acggcccacc cactttcacc ctaggctatg gcgcctgttt cggtcacaac   6600
gaagtcaagg ccatcgccat ggccatcctc gaccgcgccc tgcaaaaggg tatgcgcgac   6660
ggtcccagca acccgtcgga agacccggaa ttcgtgctgc tgcacgtcga tggcgtggat   6720
tcgatgggct ttgccagtca ctacaagatg ccgcactacg tgaccttcca gtccgacatg   6780
gaccggctgc gcaccacgca ggacaaggca accgcacaac cgacccaaga aggagcgcca   6840
tcatgaaccc gggctacgaa ctgcccctgg acgaggcggg ctacagcttc ggcttcctgg   6900
acgaatacgc caagcgcgag gtgcgccgca ccatcctcaa ggcgatcagc atccccggtt   6960
accagacgcc ctatgcctca cgcgaaatgc ctatggggcg cggctttggc accggcggtc   7020
tgcaggttac gctgtcgctg attggcgagg gcgacaccct gaaggtgatc gaccagggcg   7080
cggacgactc cgtcaacgcg gtgaacctgc gtcactttgt ggaactgacc tgcccgggcg   7140
tggacaccac agaacacacg cttgatgcca ctctgatcca gtcgcgccac cgcattccgg   7200
aaacgccgct gaccgaagcg caggtgttga tcctgcaagt gccgtatccg gacccactgg   7260
tggtggtgga accctccgag gctcgacgca aggtcatgca cggcgaaggc gactattcgc   7320
ggctgctgac caagctgtac gaggacatcg tgcagtttga cgagatcacc atctcgcacc   7380
gctaccccac gcgcatcaac ggccactatg tgatcgaccc cagcccgatc ccgcgctacg   7440
acgtgccgca gttgcaccag agcccggcgc tgatcctgct gggtgcgggg cgcgagaaaa   7500
aaatctatgc ggtgccgccg tacacccgcg ccgacccgct ggcgttcgac gacgtgccat   7560
tccgcaccga agacttcacc aacgaacacg gccagcgccg cgcctgcgaa cggtgcggcg   7620
ccaccgacag cttcctcgac gagctcattg ccgacgatgg cggcaagcac tggcattgct   7680
cggactcgga tttttgcaat agccgtatgg cccgccaggc tgaacaagct caggagacca   7740
```

-continued

```
cggtatgaaa aaaattctgg aagtacgcgg actgaccaag atccacggcc ggggttgcga   7800
actctgcctg gagagcactg gccccgacat ggacaccaac atctgcccac actgtggctc   7860
ggtggtggcc tgccacaaca tcagcctgga cctgcacgag ggcgagatcc tcggcatcat   7920
gggcgagtcc ggcagcggca agtccaccgt ggtcaagacg ctgttcttcg acgatgagcc   7980
caccgctggt gaagccctgt tttttgacgg cgagcgccag tgggacatgt tcgcgctcaa   8040
cgccgcgcag cagcgctggc ttgcgcaacc accgctttgg catggtgtac cagaacccgc   8100
atctgggact caatttcaac gtctcggccg gcggaaacat ttgccgagcg ccttgctgat   8160
gagcgacctg gcccactacg gcgaaatccg cgaacgggcg cgcagcttgt tggcgcgcac   8220
tgaggtgttg gcagaacgca tggacgagtc gcccaagaag ttctcgggcg gcatgcagca   8280
gcgcgtgcag atcgccaagg cactggccac ccagccgccg ctgctctacc tcgacgaggt   8340
caccaccggc ctggaccttt cggtgcaggc gcgcatcctg gacctgattc tggaaatcca   8400
gcaggagctg ggcaccgcca tgatcgtggt cacccacgat ctgggtgtca tccgcctgct   8460
gaccggacgc acgatcgtca tgaaatacgg ccgcggtcat cgaagtccgg gctgaccgac   8520
cagatcctcg aagaccccca gcacgcctac acccagcgcc tggtcgcgtc ggcttctctg   8580
aggaaacctg aatcatgcaa gaagccatcc tcaaaatcga aggtctctcc aaacagttcc   8640
agctgcacga ccagaacaaa ctgatcccgt cgtgtgcaca ggttcaactg gaggtgtttg   8700
ccggcgagct gaccgcgctg atcggcccga ccggcgccgg caaatcgtcg gtgctcaagg   8760
ccatttaccg cacctacctg cccagcagtg ggcgcatcct ttaccgggac gccaacggtg   8820
ccatcaccga tctggcccag gccagcgaac accgcatgct ggagctgcgc aagcaggacc   8880
tgggtttcgt cacccaattt ctgcactgtc taccgcgcaa gtcggcggtc gaggtagtgg   8940
ccgagccgct ggtgcagcgg ggcagcccgc gcgaagctgc tgccgagcgc gcgcgcgaac   9000
tgctggccct gctcaacgtg ccggaacgct tgtgggcggt accacccgcc accttctcgg   9060
gcggcgagaa acagcgcgtc aacctggcac gcgggctgat cgcccggcct cggctgctgt   9120
tgcttgacga acccacggcc agcctagacc cgtccaccac cgaccgcgtg gtggagctgt   9180
tgaagtccat caaggccgaa ggcgtggcca tgctggccat cttccacgac cccgaacttg   9240
tccgacgcct ggccgatcgc gtcgtaaccc tcacgccccc ggtgtctgcg gcggcattgc   9300
tggagacctg tgcctcatga atcccatttt gctgacccat gcccgcgtgg tgttccccac   9360
cgaagtccgt gacaacgtgg ccatcctgat cgaaggcgac accatcacag catcgacccg   9420
gccagcagcg caggtgccac cgagatcgac ctgcgcggct cgcaccctga tgccaggtct   9480
gatcgacctg cactgcgacg caatggagaa agaggtggag ccgcggcccg gcgtgcactt   9540
cccgctggag ttcgcctgtg cccaggccga caagcgcaat gcggcggccg gcatcacgac   9600
ggtgtttcat gccctgtcct ttgccaacca cgagctgggc gtgcgcaaca acgccttcgc   9660
cgccgagatc gcccgttcga ttggcgactg gcaggcccat gccctgatcg acaaccgggt   9720
gcatgtgcgt tacgaggtga cggacgaaac ggcgccgccg gtgctgtcgg cgctgctgca   9780
ggacggtcat gcgcacctca tgtctttcat ggatcacagc cccggtcagg gtcagttccg   9840
cgatgtcgag gcgtaccgcg cctacctggc caagacctac aagaccgatg aggcgcagat   9900
cgacgacatc ctggcgcgca aagccggggc cgcacagggc gccatgcggc gcatggagca   9960
gcttgcggaa ctggcccgtg cgtgcggcgt gtccattgcc agccacgacg acgacagccc  10020
gcagaaagtg gcgaccgtca aggccctggg cgctgtggtg tcggagtttc cggtgaacct  10080
ggagacggca caggccgccc gtgcacaagg cctggccacc ttgtttggcg ctcccaacat  10140
```

```
cctgcgcggc aagtcccagt cgggcaacat gcgtgccctc gatgccgtgc tggccggtgt  10200

cgccgactgc ctgtgcggtg actactcgcc agcggcgctg ttgccgtcgg tcatgcgctt  10260

gcccgatctg gccggcatcc ccctggccga ggctgtggcc ctcgtcacgt gcaacccagc  10320

tcgtgctgca ggtttgcacg accggggcga gatcgccgtg ggcaagcgcg cagacctgat  10380

tgcggtcaaa accatgggcg gactgccaca ggccgagcgg gtctggtcgg gcggtaaagc  10440

ttcgctggtc gcgcattttg accacgcctg agagggactg gcacatgcga actcgcctca  10500

tctacgtggt cggcgcctcg ggcagcggca aggacacgct catgggccat gcccgccaga  10560

agctggcggg tgatcccagg gtgtgttttg cccatcgcta catcacccga cccgcaacgg  10620

caggcggcga aaaccatgtg gccttgacca cggaggaatt caccgctcgc cagaacggca  10680

agctctttgc catgcactgg tccagccacg gcctgcatta cggaatcggc atcgagatca  10740

accagtggct gggcaaaggc atcacggtgg tgatcaacgg ctcgcgggaa tacctggacg  10800

aggcccgcca acgttacccg gagctgctgc cggtgacgat tgacgtggcc accaccgtgc  10860

tgcgtgatcg gctgctggcc cgtggccgcg aggatgccga atccattgag cagcgcctgc  10920

accgccatga aacgttgcgc ctgcagcccg tgcccggtgt gctcatccag aacaacggac  10980

ccgtcgaggt ggccggcgaa gcgctgatcc ggttgatcgc agaacacacc caaggagcgc  11040

cagtatgcgt gtgagttttc tgggcacggg cgctgcgggc ggggttccgc tctacggttg  11100

cacctgccgg gcctgtgaac gcgcaaggac cgagccacac ttcgtccgcc gcccttgcag  11160

cgccctgatt gaatccggag gtacccgggt gctactggat gccgggctga tggaccttca  11220

cgaacggttt gcgccgggta gcctggacgc gattgttctc acgcactacc accccgacca  11280

cgtgcaggga ctctttcatc tgcgctgggg taaggggacg cccatcacag tctatggccc  11340

accagacagc gaaggctgcg ccgatttgtt caagcaccct ggtgtactgg ccttcgagac  11400

ggtgcacaag ttcgaggcct tcaccgtcgg ggcgctgcgc ctgacgcccc tgccgctgct  11460

tcactccaaa cccacgctgg gctatgccat cgagggcacc cagggccaac gcttcgccta  11520

cctcacagac accctgggtt tgccgccgaa gtcggccaag ttcctgcgcg cctggggcga  11580

ctttgacatg gccatcgact gttcctatcc gccgcacccg accccgaaaa accacaacga  11640

ttgggacgaa gcacatcggt gtgccatcga atctggtgcc cgcatcacct ggctcaccca  11700

tgccggtcat gcgctggacg actggatgat ggaagagacg ccgagcgtcg caagtcatat  11760

ccggctggcc cgggacggca gcacggccga cataccgtcc caaacgcaat gaacgcgccg  11820

ctggcactgg ccctgtcggt ggccatgcac gtcacctgga acctgatggc acggcatttg  11880

cccagggaat cgaacccgct gtggtgggtg ttgctcgccc atctggtgct gtttgcgccc  11940

tgggggttct gggagctggc gacaaccgtc gtttggtcac tggagatgac gctgctactg  12000

atcgtatcgg ccactgcgaa tgtggtttat ttctccggtc tggccagggc ctacgagcac  12060

gcaccggtcg cactggtcta tcctctggtg cgcagttcac ctcttttcat tgcgatctgg  12120

ggcacgctgt tcttcggtca aaatctcccg cccattgcct ggctgggcat tggcatcagc  12180

gtgctgggct tgctcgtcat ggcatcgagt gctcaacagg ggtcggatcg acgagcattc  12240

cgatgggcca tgctggccat gttggcgaca agcgtttatt ccctgagtga caaggcggcc  12300

accgaacaca tcccaagctt catggggctc gtgggttttc tgtccgtcgg ctacctggca  12360

tcctggatca gcatgacctt gcgcatgcat cggcacaccc gcagttgggt gccggcacag  12420

cgcattgatc tcgcgtcgct ggctcttggc ggaacctgta tcggtctcgc ctacgccttg  12480
```

```
gttatccacg ccatgcgcca gttgcctgcg gcggaggtcg tgtcgtacac caacgccggt  12540

atcgtgctcg ctgcagttct ctccattttt ttgttcaatg acaaagtcgg atggcaaaag  12600

agaatcatgg gggtcgtgat catcacgagt ggtttggggg tgcttgccat gaggtgagcg  12660

acacaatacc aaccatcgca caccagcatt ccaacccggc tcgcgacctg ccggtgaagt  12720

aaaagcgact tccgatatgt cccaaatttc ccgatacgtc gaggccgccg agcgtgacaa  12780

cacgcgtcga agctatgccg cagccattcg ccatttcgag gtggagtgga aaggcttgct  12840

gccaacgacc gctgatgcaa cctcccgtta cctggctgac cacgcggcca cgctggcgat  12900

cagcaccctc cgtcagcggc tcgccgcgct ctcgcgctgg cacatcgacc atggttttgc  12960

agacccgacc aaggcaccct tggtgcgcca ggttctcaaa ggcattcgct ccattcactc  13020

ggttgcagaa aagcgggcac gccccttga aatcgatgtc gtccagcaga tcgatcaatg  13080

gctgggggtg gccatcggca acgcagaacg cagcgatgac cgattggcgc tgcttcgcca  13140

cacccgcaac cgcagtttgc tgctgctggg tttctggcgg ggatttcgat cggacgagtt  13200

ggtcaacctg cgggtggaga acgtggaagt ctcgcctggc gaagggctgt cgtgctacct  13260

gagccgcagc aagggcgatc ggcagatgct gggccgcgta tacaaatgtc cggcgctgtc  13320

ccgcctgtgt cctgtgacgg ctttcacggc atgggtcagt ctggtcggcc tgacccaagg  13380

cccggtgttt cgcaagatcg accgctgggg gcgaatcggt caagaagggc tgcatgccaa  13440

cagcctgatc ccattgttgc gcagcctttt ggctgaggcc ggggtccccg cttccgaggc  13500

atacagcagc cactccctgc gtcgcggatt tgccggttgg gctcgcgcca gcggttggga  13560

catcaaggaa ctcatggagt acgtgggctg gaaggatgtc aaatcggcca tgcgttatct  13620

ggatgcctcc ggcagcgcac ttcaggcccg gtttgaggcg ggtctcgcaa cactggcccc  13680

agcagatcga gcggatcggt caccaccgcc ttcgatgcac gcgccggccg agcaaaccaa  13740

gggaacaggc ccagaggccc cgtctgcctg a                                13771


<210> SEQ ID NO 3
<211> LENGTH: 792
<212> TYPE: DNA
<213> ORGANISM: Delftia acidoorans

<400> SEQUENCE: 3

atgcacaagt tcatccacat cacggacatt catcttgtcg agcagggtcg cgccctctac     60

ggccatgacc ccggcaaacg gttcgagcgc tgcatcgaca gcgtgatcgc cgagcacgcg    120

gacgcagcgt cttgcgtgat cacgggcgac ctcgcacatg tcgggcaccc ggacgcctac    180

cgccagctgt cggagcaatg cgcgcggttg ccaatgccgg ttcatctgat tctcggcaac    240

cacgacagcc ggaccaactt ccgcgagcgc ttcccacagg tgccggtgga cagcaatggg    300

ttcgtccagt acgagcaggc catcgggagg ttcaggggtc tgtttctgga taccaacgaa    360

ccgggaacgc attgcggcgt cttctgcgag caacgggcaa actggctttc ccagcgcttg    420

gcggaggatg attcaccggt gctcctgttc atgcatcatc cggcattcca ccttggcatc    480

ccggtcatgg atcgaatcgg attggtcgac aacgaatggt tgctgacggc gttgaagggc    540

cacgagcacc gcgtcaagca cttgttcttc ggccacattc atcgccccat ctcgggcagc    600

tggcgcggca tcccgttctc gacattgcgc ggaaccaacc accaggtggc gctgcacctt    660

cgggaatcgg aagacatccc gggaagcttc gagccaccac agtacgccgt cgtcctgctc    720

gacgacgatt cggtgatcgt gcacctgcat gactttctcg atcgcagcga gagattctgg    780

ctaggcgcgt ag                                                        792
```

<210> SEQ ID NO 4
<211> LENGTH: 4967
<212> TYPE: DNA
<213> ORGANISM: Enterobacter aerogenes

<400> SEQUENCE: 4
atgaataagc gctggctccc ctggctgata ctgtcgcctt ccctgttgtt tttactgctg 60
tttacctggt ttccgcttgg ccgttcggtc tatgacagcc tgtttgatac ccgcatggcc 120
agcgacggcg cacagtacgt cgggctggat aacttcgccc gcctgtttgc cgacggcgtt 180
ttctggcaat cgctggtcaa taatctgctc tatatcctgc tgacggtggt gcccggcgtg 240
acgctcgctc tgctgctggc ggtggcgctg agcgagaatc accgcgtcaa ccgctggctg 300
cgcaccgcct ttttcttccc gatgattatc ccgatggtta gcgccgccgc gctgtggctg 360
tttattttta tgcccggcct cggcctgctc gatcactatc tggcgaagct atttggccct 420
cagaacaaca actggctggg gcgcagcaac agcgcgctgc tggcgctggc gctgattggc 480
gtgtggaaat tcgctggcta ctacatgctg tttttcctcg ccgggctgca gagcattccg 540
gcctcaacgc gggaagcggc gctgatggaa ggggccagcc gcacccaggt gtttttttaag 600
gtcacgctgc cgctgctgcg cccgacgctg agctttgtta tcaccaccgc gctgatttac 660
tccattaccc agattgatca cgtcgcggtg atgacgcgcg gcgggccgga taacgccacg 720
accgtgctgc tctattacat ccagaatctc gcctgggata cccacgacct cggcaaagcc 780
tccgccgcca ccttcctgac gctggccggg ctgtttgcct tctcgctgat taacctgaaa 840
ttgctggaaa aaggagccca ctatgagcgc tgaaatctcg ccgctgatgg tccgctcgcc 900
cgccgctgcg cgtccgctgt ggttgcgcct gcgtcgctca cagcccttta ccctgacggt 960
aatcatgtgc tgcctggcgc tgctatgggt gagcccgttt atctggatgc tggcgacctc 1020
gttcagcgcc accaccttcg gcgaagatat ggcctcattg ctgccgcgcc tgccgctgac 1080
cctcgataac ttccgcgacg cctgggacag cgccgactgg ctgagcctgt acgccaacac 1140
ccttatcttt accttcggca ctttcttcgt gcagctactc accatcacca ccgccggcta 1200
cgtcttcgcc tgccacgaat ttcgcggcaa gaaaatgcta tttctgctgt ttctcgtcca 1260
gctgatgatc atgccggtgg tgatgatggt gccgaacatg ctgaccctga aaaccttcgg 1320
cctgctcaac actctgaccg gcgtgatgat gccttacttt acctcggcgt tcggcgtgtt 1380
tctgatgcgc caggcgttcc tcgccatccc gaaagagctg gaagaggcgg cgctgatgga 1440
gggatgccgc tggtggcagg tgctattccg cgtactgctg ccgatgtcct ggccgtcggt 1500
gctggccttc gccaccgtca gcattaccta ccactggaac gagtacctgt ggccgctgat 1560
gatgctcaac gatcccgata agcaggtgct gacggtcggg ctggtctctt tcgccatggg 1620
cgctgaatcc ggcggccagt ggggcaccat cggcgccggg acgctgatgg tctgcctgcc 1680
gctgatgctg gcgttcatcc ttttccagaa acagttcctg cgaagcttcg gcttctccgg 1740
gatcaaataa ggagttattc atgctgttag cgcacatttc cgatacccat ttccgcagcc 1800
gcggcgagaa gctgtacggc tttatcgacg tcaacgccgc caatgctgat gtggtttctc 1860
aacttaacgc gctgcgcgaa cgcccggatg cggtggtggt gagcggcgat atcgtcaact 1920
gcggccgtcc ggaggagtat caggtcgccc gccagatcct cggcagcctg aactatccgc 1980
tgtatctcat ccccggcaac cacgatgata aagcgctgtt tctggagtac ctgcagccgc 2040
tgtgtccaca gctcggtagc gatgccaata atatgcgctg tgcggttgac gacttcgcta 2100

```
cccgcctgct gtttatcgac tccagccgcg ccggcacttc aaaaggctgg ctgaccgacg   2160
agaccattag ctggctggaa gcgcagctgt tcgagggcgg cgacaaaccg gcaacgatct   2220
ttatgcacca cccgccgctg ccgctgggca atgcgcagat ggacccgatt gcctgcgaaa   2280
acggccaccg tctgctggcg ttggtagagc gtttcccgtc gctgacgcgc atcttttgcg   2340
gtcataacca tagcctgacc atgacccagt atcgccaggc gctgatctcc accctccccg   2400
gcaccgtcca tcaggtgcct tactgccacg aagacactcg cccgtattac gatctctcgc   2460
cggcttcgtg cctgatgcac cgccaggtcg gcgagcaatg ggtgagctac cagcactcgc   2520
tggcccacta cgccgggccg tggctgtacg acgaaaacat cagttgtcca acggaagagc   2580
gctaaccgcc atgctcagtc tgcaaaacat cagtaaacat ttcgacggta aaccggcgct   2640
cagcgcgctg tcgcttgata tccacgaagg tgaatttgtg gtgctggtcg gcccgtcggg   2700
ctgcggtaaa agcaccctac tgcgcctgct tgccgggttg gatcaggtca gcgaaggcga   2760
aatctggctg catgatgaga acatcaccga caccacgccg cgcgaacgca attttgcgat   2820
gatcttccag aactatgcgc tgtttccaca tctctctgtg cgcgacaaca tcaccttcgg   2880
catgaaggta cgcaaggaag agaaaagcgg ctggcagccg cgggtagata aagtggcgca   2940
gatgctgcag ctggaggcgc tgctcgatcg caaaccggcg aagctctccg gcggccaacg   3000
gcagcgggta gcgatggcgc gggcgatcgt gcgtaatccg cggctgttct taatggatga   3060
accgctgtcc aacctcgacg ctcgtctgcg cagcgaagtc cgcgacagca ttatggacct   3120
ccaccagcag ttaaaaacca gtaccgtcta cgtcacccac gatcaaaccg aagccatgtc   3180
gatggccgac cgcatcgtgg tgatgaacgg cggccacgtg cagcaagtgg ggcggccaga   3240
gtatctgtat gccaacccgg ccaatctgtt cgtggccaga tttatcggtt caccggcaat   3300
gaatctgcta tcgctcccct gcgttgacgg caacgttcag cttggcgaac aacgccatcc   3360
gctaccgccg cgccatcgca gccagacccg tgtctggctg ggcattcgcc cggaacatat   3420
taccgaccgc gtggagcacg gccatctgcg cctgccgggc accgtcctgc aacgagaact   3480
gatgggagcc gattatctgc tccacgtcag caccccgatc ggcaccctgc gctttagccg   3540
ccgccaccgt ggcacggtgc cggaaaaagg cgaatcgctg atcctcggct tctcgcctgc   3600
cgatgtgcat ctttttcatg ctgagaccca gcataattta ctgatggagt gtaatcatgt   3660
ttaacccccct caccgccctg acggttgggc tcagcctcgc cctgagcggc acggcgctgg   3720
cgaaagagaa aatagacttc atgttcccgg ccccggtaga cggcaagctg acgatggaga   3780
tgacacgcgt cattaaagcc tttaacgagt cgcagcagga tgtcgaagtg cgcggcatct   3840
tcaccggcaa ctatgacacc accaagatca aagccgaatc cgcgcagaag gccgggcaac   3900
ccccggcgct ggtgatcatg tccgccaact tcaccaccga tctggcgctg aaggatgaga   3960
tcctgccgat ggatgagctg tttaaatatg gcgatcaaaa ggccggcgat tttctgcaaa   4020
aggaattctg gcccgcgatg cataagaacg cccaggtgat gggcaccacc tatgcgatcc   4080
cgttccataa ctcgacaccg atcctctact acaacaagac gctgttagat cgagctggga   4140
tcgcgcaacc accgcagacc tgggccgagc tgctggccga tgccaaaaag ctgaccgacg   4200
agagcaaagg ccagtggggg atcatgctgc cgtcgaccaa cgacgactac ggcggctgga   4260
tcttctcggc gctggtgcgc gccaacggcg gtaaatattt caatgaagac tatccgggtg   4320
aggtttatta caactcgccg accgctatcg gcgctctgcg cttctggcag gatctgatct   4380
acaaagacaa agtgatgcct tccggggtac tgaattcgaa gcagatcagc gcttcattct   4440
tctccggcaa acttggcatg gcgatgctca gcaccggcgc actgggcttt atgcgcgaga   4500
```

```
acagtaaaga ttttgaactc ggtgtcgcca tgctaccagc caaagagcag cgcgcggtgc   4560

caattggcgg cgccagcctg gtgagcttta aaggcatcaa cgacgcgcag aagaaagcgg   4620

cctaccagtt cctgacttat ctggtgagcc cgcaggtaaa cggcgcgtgg agccgcttta   4680

ccggctactt ctcgccgcgt aaggcttctt acgatactcc ggagatgaaa gcttatctgc   4740

agcaggatcc acgagcagcg atcgcccttg aacagctgaa gtacgcgcat ccgtggtact   4800

ccacctggga gaccgtcgcc gtgcgtaagg cgatggagaa ccagctggcg gcagtggtca   4860

acgatgccaa agtaacgccg gaagccgcgg tacaggcagc gcagaaggaa gctgacgcgc   4920

taatgaaacc ttatgttgat aagactgcgc tgggagaagt gcagtag                 4967
```

<210> SEQ ID NO 5
<211> LENGTH: 1014
<212> TYPE: DNA
<213> ORGANISM: Flavobacterium sp.

<400> SEQUENCE: 5

```
atgtcgatcg gcacaggcga tcggatcaat accgtgcgcg gtcctatcac aatctctgaa     60

gcgggtttca cactgactca cgagcacatc tgcggcagct cggcaggatt cttgcgtgct    120

tggccagagt tcttcggtag ccgcaaagct ctagcggaaa aggctgtgag aggattgcgc    180

cgcgccagag cggctggcgt gcgaacgatt gtcgatgtgt cgactttcga tatcggtcgc    240

gacgtcagtt tattggccga ggtttcgcgg gctgccgacg ttcatatcgt ggcggcgacc    300

ggcttgtggt tcgacccgcc actttcgatg cgattgagga gtgtagagga actcacacag    360

ttcttcctgc gtgagattca atatggcatc gaagacaccg gaattagggc gggcattatc    420

aaggtcgcga ccacaggcaa ggcgaccccc tttcaggagt tagtgttaaa ggcggccgcc    480

cgggccagct tggccaccgg tgttccggta accactcaca cggcagcaag tcagcgcgat    540

ggtgagcagc aggccgccat ttttgagtcc gaaggcttga gcccctcacg ggtttgtatt    600

ggtcacagcg atgatactga cgatttgagc tatctcaccg ccctcgctgc gcgcggatac    660

ctcatcggtc tagaccacat cccgcacagt gcgattggtc tagaagataa tgcgagtgca    720

tcagccctcc tgggcatccg ttcgtggcaa acacgggctc tcttgatcaa ggcgctcatc    780

gaccaaggct acatgaaaca aatcctcgtt tcgaatgact ggctgttcgg gttttcgagc    840

tatgtcacca acatcatgga cgtgatggat cgcgtgaacc ccgacgggat ggccttcatt    900

ccactgagag tgatcccatt cctacgagag aagggcgtcc cacaggaaac gctggcaggc    960

atcactgtga ctaacccggc gcggttcttg tcaccgacct tgcgggcgtc atga         1014
```

<210> SEQ ID NO 6
<211> LENGTH: 1431
<212> TYPE: DNA
<213> ORGANISM: Pseudomonas aeruginosa

<400> SEQUENCE: 6

```
atgaccccag gttatcccct cgccctctct cttgccgtct ccatggccgt gctcggcagc     60

gccttgccgg cccaggcgcg ccaggacgat ccgtcactgt tcaaccgcca ggcccgtggc    120

gaactcagcg agtacggcgg cgcacggcgc gtcgagcagg acctgaccca ggccctgaag    180

cagtcgctgt cgaagaagaa ggcgaagaac gtgatcctgc tgatcggcga cggcatgggc    240

gactccgaga tcaccgtggc gcgcaactac gcgcgcggcg cgggcggcta cttcaagggt    300

atcgatgcgc tgccgctgac cggtcagtac acccactact ccctgcacaa ggacagcggc    360
```

```
ctgccggact acgtgaccga ttccgccgcc tccgccaccg cctggtccac cggggtcaag    420

tcgtacaacg gcgcgatcgg cgtggatatc cacgaacagc cgcaccgcaa cctgctggag    480

ctggccaagc tcaacggcaa ggccaccggc aacgtctcca ccgccgagct gcaggacgcc    540

accccccgccg ccctgctcgc ccacgtcacc gctcgcaagt gctacggtcc cgaggccacc    600

agcaagcagt gcccgagcaa tgccctggag aacggcggcg ccggctcgat caccgagcag    660

tggctgaaga cccgccctga cgtggttctc ggcggcggcg ccgcgacctt cgcggaaacc    720

gccaaggctg gccgctatgc cggcaagacc ctccgcgccc aggccgaagc ccgcggctac    780

cggatcgtcg agaacctcga cgagctgaaa gccgtgcgcc gcgccaacca gaagcagccg    840

ctgatcggcc tgttcgcgcc gggcaacatg ccagtgcgct ggctcggtcc gaccgccacc    900

taccacggca acctgaacca gccggcggtg agctgcgagg cgaacccgaa gcgcaccgcc    960

gacatcccga ccctggcgca aatgaccagc aaggccatcg agctgctgaa ggacaatccg   1020

aacggcttct tcctgcaggt cgagggcgcg tccatcgaca agcaggacca tgccgcgaat   1080

ccgtgcggcc agatcggcga gaccgtcgac ctcgacgaag ccgtgcagaa ggccctggcc   1140

tttgccaagg ccgatggcga gaccctggtg atcgtcaccg ccgaccacgc ccactccagc   1200

cagatcatcc cgccggaaac cgccgcgccg gggctgaccc aactgctcac gaccaaggac   1260

ggcgcgccgc tggcgatcag ctacggcaac tccgaggaaa gctcccagga gcacaccggc   1320

acccagttgc gcatcgccgc ctacggcccg caggccgcca atgtcaccgg cctgaccgac   1380

cagaccgacc tgttcttcac catccgtcgc gcactgaacc tgcgcgactg a            1431
```

<210> SEQ ID NO 7
<211> LENGTH: 504
<212> TYPE: DNA
<213> ORGANISM: Pseudomonas monteilii

<400> SEQUENCE: 7

```
atgaaagaac taaaaacctg gaagtgggaa gataaagaga gaacaatgct gagaaaaatc     60

tctgttggag atatattttg cctcaccaaa gacaacagca actatcattt cggtaaaatc    120

ttgtcaaaaa tgattgtagg ccacgcagtc gaaatattaa atatcactaa agacagccca    180

tcaatcaccc agcaagaact tgaacaatca gccttagcag gccgaccgct actgctagat    240

agttacgctt tattcgacaa gaaaattgac aaaggtggcg actggagaat aattggccat    300

caagagatat catcaccaga atcctatcga aactactact tcctgttcct gtacggaaca    360

cacaacaact ggaaaaaagt caacatcctc aatgaggaag ttgaaatatc aaatacagag    420

gccctaacgc tccccttgct taaagctctt agcaatcaca gattctggga aacaataaac    480

gaagaactaa agctaaactg gtaa                                            504
```

<210> SEQ ID NO 8
<211> LENGTH: 579
<212> TYPE: DNA
<213> ORGANISM: Rhodococcus sp.

<400> SEQUENCE: 8

```
ttgtctgaca agccgaatgc cgtttccagc cacaccaccc ccgacgtccc cgaagtagcg     60

gcgacgcccg agttgtccac cggcatctgc gccggtgact accgcgctgc gcttcgccgc    120

caccccgccg gtgtcaccgt cgtgaccctc gattcgggta ccggcccggt gggtttcacc    180

gccacctcgt tctcgtccgt ctccctcgag ccgccgctcg tctcgttcaa catcgcggag    240

acgtcgtcga gcatcaatgc actcaaggca gccgagtcct tggtgatcca ccttctcggc    300
```

```
gaacatcagc agcatctggc ccagcgcttt gcgcgtagtg ccgatcagcg ttttgcagac    360

gagtcactgt gggcagtgct cgacaccggg gaaccggtgc tgcacggcac ccccagctgg    420

atgcgcgtca aggtcgacca gctgatccct gtcggcgacc acacgctggt catcggactc    480

gtcacgcggg ttcacgccga agaagacgac gaatccgctg ccgcgccgct gctctaccac    540

gagggcaagt actaccgccc gactccgtta ggtcaatag                           579
```

<210> SEQ ID NO 9
<211> LENGTH: 3720
<212> TYPE: DNA
<213> ORGANISM: Rhodococcus sp.

<400> SEQUENCE: 9

```
atgactcaac aacgacaaat gcatctggcc ggtttcttct cggccggcaa tgtgactcat     60

gcacatgggg cgtggcggca cacggacgcg tcgaatgact ttctgtcggg gaagtactac    120

caacacatcg cccgtactct ggagcgcggc aagttcgatc tgttgtttct gcctgacggg    180

ttggccgtcg aggacagcta cggggacaac ctggacaccg gtgtcggcct gggcgggcag    240

ggtgcagtcg ccttggagcc ggccagtgtg gtcgcaacca tggccgcggt gaccgagcac    300

ctgggtcttg gggcaaccat ttcggcgacc tactatcccc cgtatcacgt tgctcgggtg    360

ttcgcgacgc tcgatcagtt gtcagggggt cgggtgtcct ggaacgtcgt cacctcgctc    420

aacgacgctg aagcgcgcaa cttcggcatt aatcagcatc tggaacacga cgcccgctat    480

gaccgcgccg atgagttctt ggaagcggtc aagaaactct ggaacagctg ggacgaggac    540

gccctcgtgc tggacaaggc ggccggcgtg ttcgccgatc ccgcgaaggt gcactacgtc    600

gatcaccacg gggagtggct gaatgtgcgc ggacctctgc aggtaccgcg ttcacctcag    660

ggtgagccgg tgatcctgca ggccggcctg tcgccccggg gtcggcgctt cgccgggaag    720

tgggccgagg ccgtcttcag tcttgcaccc aacctcgagg tgatgcaggc cacctaccag    780

ggcatcaaag ccgaggtcga cgctgcgggg cgcgatcccg atcagacgaa aatcttcacc    840

gccgtgatgc cggtactcgg cgaaagccag gcggtggcac aggaacgact ggaatatctc    900

aacagtctgg tccatccgga agtgggactg tcgacgctat ccagtcacac cggcatcaac    960

ctggcggcgt accctctcga cactccgatc aaggacatcc tgcgggatct gcaggatcgg   1020

aatgtcccga cgcaactgca catgttcgcc gccgcaacgc acagcgaaga gctcacgctg   1080

gcggaaatgg gtcggcgcta tggaaccaac gtggggttcg ttcctcagtg ggccggtacc   1140

ggggagcaga tcgctgacga gctgatccgc cacttcgagg gcggcgccgc ggatggtttc   1200

atcatctctc cggccttcct gccgggctcc tacgacgagt tcgtcgacca ggtggttccg   1260

gttctgcagg atcgcggcta cttccgcacc gagtaccagg gcaacactct gcgcgaccac   1320

ttgggtctgc gcgtaccaca actgcaagga caaccttcat gacaagccgc gtcgaccccg   1380

caaaccccgg ttcagaactc gattccgcca tccgcgacac actgacctac agcaactgcc   1440

cggtacccaa cgctctgctc acggcatcgg aatcgggctt cctcgacgcc gccggcatcg   1500

aactcgacgt cctcagcggc cagcagggca cggttcattt cacctacgac cagcctgcct   1560

acacccgttt tgggggtgag atcccgccac tgctcagcga ggggttgcgg gcacctgggc   1620

gcacgcgtct actcggcatc accccgctct tggggcgcca gggcttcttt gtccgcgacg   1680

acagcccgat cacagcggcc gccgaccttg ccggacgtcg aatcggcgtc tcggcctcgg   1740

caattcgcat cctgcgcggc cagctgggcg actacctcga gttggatccc tggcggcaaa   1800
```

```
cgctggtagc gctgggctcg tgggaggcgc gcgccttgtt gcacaccctt gagcacggtg   1860

aactgggtgt ggacgacgtc gagctggtgc cgatcagcag tcctggtgtc gatgttcccg   1920

ctgagcagct cgaagaatcg gcgaccgtca agggtgcgga cctctttccc gatgtcgccc   1980

gcggtcaggc cgcggtgttg gccagcggag acgttgacgc cctgtacagt tggctgccct   2040

gggccgggga gttgcaagcc accggggccc gcccagtggt ggatctcggc ctcgatgagc   2100

gcaatgccta cgccagtgtg tggacggtca gcagcgggct ggttcgccag cgacctggcc   2160

ttgttcaacg actggtcgac gcggccgtcg acgccgggct gtgggcacgc gatcattccg   2220

acgcggtgac cagcctgcac gccgcgaacc tgggcgtatc gaccggagca gtaggccagg   2280

gcttcggcgc cgacttccag cagcgtctgg ttccacgcct ggatcacgac gccctcgccc   2340

tcctggagcg cacacagcaa ttcctgctca ccaacaactt gctgcaggaa cccgtcgccc   2400

tcgatcagtg ggcggctccg gaatttctga acaacagcct caatcgccac cgataggaac   2460

atccgcatga cactgtcacc tgaaaagcag cacgttcgac cacgcgacgc cgccgacaac   2520

gatcccgtcg cggttgcccg tgggctagcc gaaaagtggc gagccaccgc cgtcgagcgt   2580

gatcgcgccg gggttcggc aacagccgag cgcgaagacc tgcgcgcgag cgcgctgctg   2640

tcgctcctcg tcccgcgcga atacggcggc tggggcgcag actggcccac cgccatcgag   2700

gtcgtccgcg aaatcgcggc agccgatgga tctttgggac acctgttcgg ataccacctc   2760

accaacgccc cgatgatcga actgatcggc tcgcaggaac aagaagaaca cctgtacacc   2820

cagatcgcgc agaacaactg gtggaccgga aatgcctcca gcgagaacaa cagccacgtg   2880

ctggactgga aggtcagcgc caccccgacc gaagacggcg gctacgtgct caatggcacg   2940

aagcacttct gcagcggcgc caaggggtcg gacctgctgt tcgtgttcgg cgtcgtccag   3000

gatgattctc cgcagcaggg tgcgatcatt gctgccgcta tcccgacatc gcgggctggc   3060

gttacgccca acgacgactg ggccgccatc ggcatgcggc agaccgacag cggttccacg   3120

gacttccaca acgtcaaggt cgagcctgac gaagtgctgg gcgcgcccaa cgccttcgtt   3180

ctcgccttca tacaatccga gcgcggcagc ctcttccggc ccatagcgca attgatcttc   3240

gccaacgtct atctggggat cgcgcacggc gcactcgatg ccgccaggga gtacacccgt   3300

acccaggcga ggccctggac accggccggt attcaacagg caaccgagga tccctacacc   3360

atccgctcct acggtgagtt caccatcgca ttgcagggag ctgacgccgc cgcccgtgaa   3420

gcggcccacc tgctgcagac ggtgtgggac aagggcgacg cgctcacccc cgaggaccgc   3480

ggcgaactga tggtgaaggt ctcgggagtc aaagcgttgg ccaccaacgc cgccctcaac   3540

atcagcagcg gcgtcttcga ggtgatcggc gcgcgcggaa cacatcccag gtacggtttc   3600

gaccgcttct ggcgcaacgt gcgcacccac tccctgcacg acccggtgtc ctacaagatc   3660

gccgacgtcg gcaagcacac cttgaacggt caatacccga ttcccggctt cacctcctga   3720
```

<210> SEQ ID NO 10
<211> LENGTH: 196
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

```
Met Leu Asn Pro Val Trp Leu Lys Ser Leu Val Ala Ile Val Gln Thr
1               5                   10                  15

Gly Ser Phe Gln Ser Ala Ala Arg Ala Leu Gly Leu Ala Gln Pro Thr
```

```
            20                  25                  30

Val Ser Gln His Leu Gln Lys Leu Glu Glu Gln Val Gly Val Thr Leu
        35                  40                  45

Val Gln Arg Ser Arg Ser Gly Cys Gln Pro Thr Thr Arg Ala Leu Ala
    50                  55                  60

Phe Met Pro His Ala Thr Ala Leu Leu Asp Met His Ala Arg Ala Leu
65                  70                  75                  80

Glu Ala Leu His Gly Asn Arg Glu Arg Val Gly Ala Ser Ser Asn Ile
                85                  90                  95

Gly Thr Tyr Leu Leu Gln Pro Phe Val Arg Asn Tyr Leu Thr Thr Ala
            100                 105                 110

Asn Glu Arg Gly Glu Val Asp Leu Arg Ile Ala Ala Asn Pro Asp Val
        115                 120                 125

Ala Asp Gln Leu Leu Ala Gly Gln Leu Asp Ala Ala Ile Met Glu Trp
    130                 135                 140

Trp Leu Pro His Pro Asp Phe Glu Tyr Arg Leu Trp Arg Val Glu Pro
145                 150                 155                 160

Leu Val Leu Ile Val Ser Pro Asp His Ala Leu Ala Glu Ala Gly Cys
                165                 170                 175

Ile Glu Arg Asp Arg Leu Val Asp Leu Pro Met Leu Gly Gly Glu Pro
            180                 185                 190

Gly Ser Gly Thr
        195


<210> SEQ ID NO 11
<211> LENGTH: 8184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

ttatcgatga taagctgtca aagatgagaa ttaattccac ggactataga ctatactaga     60

tactccgtct actgtacgat acacttccgc tcaggtcctt gtcctttaac gaggccttac    120

cactcttttg ttactctatt gatccagctc agcaaaggca gtgtgatcta agattctatc    180

ttcgcgatgt agtaaaacta gctagaccga gaaagagact agaaatgcaa aaggcacttc    240

tacaatggct gccatcatta ttatccgatg tgacgctgca gcttctcaat gatattcgaa    300

tacgctttga ggagatacag cctaatatcc gacaaactgt tttacagatt tacgatcgta    360

cttgttaccc atcattgaat tttgaacatc cgaacctggg agttttccct gaaacagata    420

gtatatttga acctgtataa taatatatag tctagcgctt tacggaagac aatgtatgta    480

tttcggttcc tggagaaact attgcatcta ttgcataggt aatcttgcac gtcgcatccc    540

cggttcattt tctgcgtttc catcttgcac ttcaatagca tatctttgtt aacgaagcat    600

ctgtgcttca ttttgtagaa caaaaatgca acgcgagagc gctaattttt caaacaaaga    660

atctgagctg catttttaca gaacagaaat gcaacgcgaa agcgctattt taccaacgaa    720

gaatctgtgc ttcatttttg taaaacaaaa atgcaacgcg acgagagcgc taatttttca    780

aacaaagaat ctgagctgca tttttacaga acagaaatgc aacgcgagag cgctatttta    840

ccaacaaaga atctatactt ctttttttgtt ctacaaaaat gcatcccgag agcgctattt    900

ttctaacaaa gcatcttaga ttactttttt tctcctttgt gcgctctata atgcagtctc    960

ttgataactt tttgcactgt aggtccgtta aggttagaag aaggctactt tggtgtctat   1020
```

```
tttctcttcc ataaaaaaag cctgactcca cttcccgcgt ttactgatta ctagcgaagc   1080

tgcgggtgca tttttcaag ataaaggcat ccccgattat attctatacc gatgtggatt   1140

gcgcatactt tgtgaacaga aagtgatagc gttgatgatt cttcattggt cagaaaatta   1200

tgaacggttt cttctatttt gtctctatat actacgtata ggaaatgttt acattttcgt   1260

attgttttcg attcactcta tgaatagttc ttactacaat tttttgtct aaagagtaat   1320

actagagata aacataaaaa atgtagaggt cgagtttaga tgcaagttca aggagcgaaa   1380

ggtggatggg taggttatat agggatatag cacagagata tatagcaaag agatactttt   1440

gagcaatgtt tgtggaagcg gtattcgcaa tttaattaag tttaaacgat ccaactggca   1500

ccgctggctt gaacaacaat accagccttc caacttctgt aaataacggc ggtacgccag   1560

tgccaccagt accgttacct ttcggtatac ctcctttccc catgtttcca atgcccttca   1620

tgcctccaac ggctactatc acaaatcctc atcaagctga cgcaagccct aagaaatgaa   1680

taacaatact gacagtacta aataattgcc tacttggctt cacatacgtt gcatacgtcg   1740

atatagataa taatgataat gacagcagga ttatcgtaat acgtaatagt tgaaaatctc   1800

aaaaatgtgt gggtcattac gtaaataatg ataggaatgg gattcttcta tttttccttt   1860

ttccattcta gcagccgtcg ggaaaacgtg gcatcctctc tttcgggctc aattggagtc   1920

acgctgccgt gagcatcctc tctttccata tctaacaact gagcacgtaa ccaatggaaa   1980

agcatgagct tagcgttgct ccaaaaaagt attggatggt taataccatt tgtctgttct   2040

cttctgactt tgactcctca aaaaaaaaaa atctacaatc aacagatcgc ttcaattacg   2100

ccctcacaaa aactttttc cttcttcttc gcccacgtta aattttatcc ctcatgttgt   2160

ctaacggatt tctgcacttg atttattata aaaagacaaa gacataatac ttctctatca   2220

atttcagtta ttgttcttcc ttgcgttatt cttctgttct tctttttctt ttgtcatata   2280

taaccataac caagtaatac atattcaaaa tgaagaagcc cgagctgacc gctacctctg   2340

ttgagaagtt cctgattgag aagtttgatt ccgtttccga cctgatgcag ctgtccgagg   2400

gcgaggagtc tcgagccttc tcctttgacg tgggcggacg aggttacgtt ctgcgagtga   2460

actcgtgtgc cgacggcttc tacaaggatc gatacgtcta ccgacacttt gcttctgccg   2520

ctctgcccat ccctgaggtt ctcgacattg gcgagttctc tgagtccctc acctactgca   2580

tctctcgacg agctcaggga gtcaccctgc aggacctccc tgagactgag ctgcctgctg   2640

tcctccagcc tgttgctgag gccatggacg ctatcgctgc tgctgatctg tcccagacct   2700

cgggtttcgg cccctttgga cctcagggaa ttggacagta caccacttgg cgagacttca   2760

tctgtgctat tgccgatcct cacgtctacc attggcagac cgttatggac gatactgtgt   2820

cggcttctgt cgctcaggct ctggacgagc tgatgctctg ggccgaggat tgccccgagg   2880

ttcgacacct ggtgcatgct gacttcggtt ccaacaacgt tctcaccgac aacggccgaa   2940

tcactgccgt gattgactgg tccgaggcta tgtttggcga ctcgcagtac gaggtggcca   3000

acatcttctt ttggcgaccc tggctggctt gtatggagca gcagacccga tacttcgagc   3060

gacgacatcc tgagctcgct ggatcccctc gactgcgagc ttacatgctc cgaattggtc   3120

tggaccagct ctaccagtcg ctggtggatg gcaactttga cgatgctgcc tgggctcagg   3180

gacgatgtga cgccatcgtg cgatctggcg ctggaaccgt cggacgaact cagattgccc   3240

gacgatccgc tgctgtctgg accgacggat gcgtggaggt cctggctgat tcgggtaacc   3300

gacgaccctc tactcgacct cgagctaagg agtaataaac ggcgcgccgt taattcaaat   3360
```

```
taattgatat agttttttaa tgagtattga atctgtttag aaataatgga atattatttt   3420
tatttattta tttatattat tggtcggctc ttttcttctg aaggtcaatg acaaaatgat   3480
atgaaggaaa taatgatttc taaaatttta caacgtaaga tatttttaca aaagcctagc   3540
tcatcttttg tcaagagacc gggttggcgg cgcatttgtg tcccaaaaaa cagccccaat   3600
tgccccaatt gaccccaaat tgacccagta gcgggcccaa ccccggcgag agccccottc   3660
tccccacata tcaaacctcc cccggttccc acacttgccg ttaagggcgt agggtactgc   3720
agtctggaat ctacgcttgt tcagactttg tactagtttc tttgtctggc catccgggta   3780
acccatgccg gacgcaaaat agactactga aatttttttt gctttgtggt tgggacttta   3840
gccaagggta taaaagacca ccgtccccga attacctttc ctcttctttt ctctctctcc   3900
ttgtcaactc acacccgaaa tcgttaagca tttccttctg agtataagaa tcattcaaaa   3960
tggtgagttt cagaggcagc agcaattgcc acgggctttg agcacacggc cgggtgtggt   4020
cccattccca tcgacacaag acgccacgtc atccgaccag cactttttgc agtactaacc   4080
gcagatgctg ccgaaactcg ttataactca ccgagtacac gatgagatcc tgcaactgct   4140
ggcgccacat tgcgagctga tgaccaacca gaccgacagc acgctgacgc gcgaggaaat   4200
tctgcgccgc tgtcgcgatg ctcaggcgat gatggcgttc atgcccgatc gggtcgatgc   4260
agactttctt caagcctgcc ctgagctgcg tgtagtcggc tgcgcgctca agggcttcga   4320
caatttcgat gtggacgcct gtactgcccg cggggtctgg ctgaccttcg tgcctgatct   4380
gttgacggtc ccgactgccg agctggcgat cggactggcg gtggggctgg ggcggcatct   4440
gcgggcagca gatgcgttcg tccgctctgg cgagttccag ggctggcaac cacagttcta   4500
cggcacgggg ctggataacg ctacggtcgg catccttggc atgggcgcca tcggactggc   4560
catggctgat cgcttgcagg gatggggcgc gaccctgcag taccacgagg cgaaggctct   4620
ggatacacaa accgagcaac ggctcggcct gcgccaggtg gcgtgcagcg aactcttcgc   4680
cagctcggac ttcatcctgc tggcgcttcc cttgaatgcc gatacccagc atctggtcaa   4740
cgccgagctg cttgccctcg tacggccggg cgctctgctt gtaaacccct gtcgtggttc   4800
ggtagtggat gaagccgccg tgctcgcggc gcttgagcga ggccagctcg gcgggtatgc   4860
ggcggatgta ttcgaaatgg aagactgggc tcgcgcggac cggccgcggc tgatcgatcc   4920
tgcgctgctc gcgcatccga atacgctgtt cactccgcac atagggtcgg cagtgcgcgc   4980
ggtgcgcctg gagattgaac gttgtgcagc gcagaacatc atccaggtat tggcaggtgc   5040
gcgcccaatc aacgctgcga accgtctgcc caaggccgag cctgccgcat gttgagcgtc   5100
tacaactgga cccttagcct gtatatatca attgattatt taaagatttg gtcggtaggc   5160
ggttcgtatt gtacaatggg atctgttact gaggtggatc tacccaactt gcgagattca   5220
attgcgagat tcaatcgcga gattcaattg cgagaatcag ttgcgagttg ttctaacact   5280
cagcttctac gagcgcttgt attaggacga gtgatactcc gtggggcgac ggcttctctt   5340
gcgtcttctg ttgtattctt tcttacacta tcgtccatct ccaaccacct cgtacgttta   5400
aacggcgcgc ctttccatag gctccgcccc cctgacgagc atcacaaaaa tcgacgctca   5460
agtcagaggt ggcgaaaccc gacaggacta taaagatacc aggcgtttcc ccctggaagc   5520
tccctcgtgc gctctcctgt tccgaccctg ccgcttaccg gatacctgtc cgcctttctc   5580
ccttcgggaa gcgtggcgct ttctcatagc tcacgctgta ggtatctcag ttcggtgtag   5640
gtcgttcgct ccaagctggg ctgtgtgcac gaaccccccg ttcagcccga ccgctgcgcc   5700
ttatccggta actatcgtct tgagtccaac ccggtaagac acgacttatc gccactggca   5760
```

```
gcagccactg gtaacaggat tagcagagcg aggtatgtag gcggtgctac agagttcttg   5820
aagtggtggc ctaactacgg ctacactaga agaacagtat ttggtatctg cgctctgctg   5880
aagccagtta ccttcggaaa aagagttggt agctcttgat ccggcaaaca aaccaccgct   5940
ggtagcggtg gtttttttgt ttgcaagcag cagattacgc gcagaaaaaa aggatctcaa   6000
gaagatcctt tgatcttttc tacggggtct gacgctcagt ggaacgaaaa ctcacgttaa   6060
gggattttgg tcatgagatt atcaaaaagg atcttcacct agatcctttt aaattaaaaa   6120
tgaagtttta aatcaatcta aagtatatat gagtaaactt ggtctgacag ttaccaatgc   6180
ttaatcagtg aggcacctat ctcagcgatc tgtctatttc gttcatccat agttgcctga   6240
ctccccgtcg tgtagataac tacgatacgg gagggcttac catctggccc cagtgctgca   6300
atgataccgc gagacccacg ctcaccggct ccagatttat cagcaataaa ccagccagcc   6360
ggaagggccg agcgcagaag tggtcctgca actttatccg cctccatcca gtctattaat   6420
tgttgccggg aagctagagt aagtagttcg ccagttaata gtttgcgcaa cgttgttgcc   6480
attgctacag gcatcgtggt gtcacgctcg tcgtttggta tggcttcatt cagctccggt   6540
tcccaacgat caaggcgagt tacatgatcc cccatgttgt gcaaaaaagc ggttagctcc   6600
ttcggtcctc cgatcgttgt cagaagtaag ttggccgcag tgttatcact catggttatg   6660
gcagcactgc ataattctct tactgtcatg ccatccgtaa gatgcttttc tgtgactggt   6720
gagtactcaa ccaagtcatt ctgagaatag tgtatgcggc gaccgagttg ctcttgcccg   6780
gcgtcaatac gggataatac cgcgccacat agcagaactt taaaagtgct catcattgga   6840
aaacgttctt cggggcgaaa actctcaagg atcttaccgc tgttgagatc cagttcgatg   6900
taacccactc gtgcacccaa ctgatcttca gcatctttta ctttcaccag cgtttctggg   6960
tgagcaaaaa caggaaggca aaatgccgca aaaaagggaa taagggcgac acggaaatgt   7020
tgaatactca tactcttcct ttttcaatat tattgaagca tttatcaggg ttattgtctc   7080
atgagcggat acatatttga atgtatttag aaaaataaac agcgatcgcg cggccgcggg   7140
taataactga tataattaaa ttgaagctct aatttgtgag tttagtatac atgcatttac   7200
ttataataca gttttttagt tttgctggcc gcatcttctc aaatatgctt cccagcctgc   7260
ttttctgtaa cgttcaccct ctaccttagc atcccttccc tttgcaaata gtcctcttcc   7320
aacaataata atgtcagatc ctgtagagac cacatcatcc acggttctat actgttgacc   7380
caatgcgtct cccttgtcat ctaaacccac accgggtgtc ataatcaacc aatcgtaacc   7440
ttcatctctt ccacccatgt ctctttgagc aataaagccg ataacaaaat ctttgtcgct   7500
cttcgcaatg tcaacagtac ccttagtata ttctccagta gctagggagc ccttgcatga   7560
caattctgct aacatcaaaa ggcctctagg ttcctttgtt acttcttccg ccgcctgctt   7620
caaaccgcta acaatacctg ggcccaccac accgtgtgca ttcgtaatgt ctgcccattc   7680
tgctattctg tatacacccg cagagtactg caatttgact gtattaccaa tgtcagcaaa   7740
ttttctgtct tcgaagagta aaaaattgta cttggcggat aatgccttta gcggcttaac   7800
tgtgccctcc atggaaaaat cagtcaagat atccacatgt gtttttagta aacaaatttt   7860
gggacctaat gcttcaacta actccagtaa ttccttggtg gtacgaacat ccaatgaagc   7920
acacaagttt gtttgctttt cgtgcatgat attaaatagc ttggcagcaa caggactagg   7980
atgagtagca gcacgttcct tatatgtagc tttcgacatg atttatcttc gtttcctgca   8040
ggtttttgtt ctgtgcagtt gggttaagaa tactgggcaa tttcatgttt cttcaacacc   8100
```

acatatgcgt atatatacca atctaagtct gtgctccttc cttcgttctt ccttctgctc 8160
ggagattacc gaatcaaagc tagc 8184

<210> SEQ ID NO 12
<211> LENGTH: 196
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Leu Asn Pro Val Trp Leu Lys Ser Leu Val Ala Ile Val Gln Thr
1 5 10 15

Gly Ser Phe Gln Ser Ala Ala Arg Ala Leu Gly Leu Ala Gln Pro Thr
20 25 30

Val Ser Gln His Leu Gln Lys Leu Glu Glu Gln Val Gly Val Thr Leu
35 40 45

Val Gln Arg Ser Arg Ser Gly Cys Gln Pro Thr Thr Arg Ala Leu Ala
50 55 60

Phe Met Pro His Ala Thr Ala Leu Leu Asp Met His Ala Arg Ala Leu
65 70 75 80

Glu Ala Leu His Gly Asn Arg Glu Arg Val Gly Ala Ser Ser Asn Ile
85 90 95

Gly Thr Tyr Leu Leu Gln Pro Phe Val Arg Asn Tyr Leu Thr Thr Ala
100 105 110

Asn Glu Arg Gly Glu Val Asp Leu Arg Ile Ala Ala Asn Pro Asp Val
115 120 125

Ala Asp Gln Leu Leu Ala Gly Gln Leu Asp Ala Ala Ile Met Glu Trp
130 135 140

Trp Leu Pro His Pro Asp Phe Glu Tyr Arg Leu Trp Arg Val Glu Pro
145 150 155 160

Leu Val Leu Ile Val Ser Pro Asp His Ala Leu Ala Glu Ala Gly Cys
165 170 175

Ile Glu Arg Asp Arg Leu Val Asp Leu Pro Met Leu Gly Gly Glu Pro
180 185 190

Gly Ser Gly Thr
195

<210> SEQ ID NO 13
<211> LENGTH: 9203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
gtttgtggaa gcggtattcg caatcattta gtcgtgcaat gtatgacttt aagatttgtg 60
agcaggaaga aaagggagaa tcttctaacg ataaaccctt gaaaaactgg gtagactacg 120
ctatgttgag ttgctacgca ggctgcacaa ttacacgaga atgctcccgc ctaggattta 180
aggctaaggg acgtgcaatg cagacgacag atctaaatga ccgtgtcggt gaagtgttcg 240
ccaaactttt cggttaacac atgcagtgat gcacgcgcga tggtgctaag ttacatatat 300
atatatatat atatatatat atatatatag ccatagtgat gtctaagtaa cctttatggt 360
atatttctta atgtggaaag atactagcgc gcgcacccac acacaagctt cgtcttttct 420

```
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaatttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc cccctgacga gcatcacaaa aatcgacgct   2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
```

```
aagaagatcc tttgatcttt tctacggggt ctgacgctca gtggaacgaa aactcacgtt   2880

aagggatttt ggtcatgaga ttatcaaaaa ggatcttcac ctagatcctt ttaaattaaa   2940

aatgaagttt taaatcaatc taaagtatat atgagtaaac ttggtctgac agttaccaat   3000

gcttaatcag tgaggcacct atctcagcga tctgtctatt tcgttcatcc atagttgcct   3060

gactccccgt cgtgtagata actacgatac gggagggctt accatctggc cccagtgctg   3120

caatgatacc gcgagaccca cgctcaccgg ctccagattt atcagcaata aaccagccag   3180

ccggaagggc cgagcgcaga agtggtcctg caactttatc cgcctccatc cagtctatta   3240

attgttgccg ggaagctaga gtaagtagtt cgccagttaa tagtttgcgc aacgttgttg   3300

ccattgctac aggcatcgtg gtgtcacgct cgtcgtttgg tatggcttca ttcagctccg   3360

gttcccaacg atcaaggcga gttacatgat cccccatgtt gtgcaaaaaa gcggttagct   3420

ccttcggtcc tccgatcgtt gtcagaagta agttggccgc agtgttatca ctcatggtta   3480

tggcagcact gcataattct cttactgtca tgccatccgt aagatgcttt tctgtgactg   3540

gtgagtactc aaccaagtca ttctgagaat agtgtatgcg gcgaccgagt tgctcttgcc   3600

cggcgtcaat acgggataat accgcgccac atagcagaac tttaaaagtg ctcatcattg   3660

gaaaacgttc ttcggggcga aaactctcaa ggatcttacc gctgttgaga tccagttcga   3720

tgtaacccac tcgtgcaccc aactgatctt cagcatcttt tactttcacc agcgtttctg   3780

ggtgagcaaa aacaggaagg caaaatgccg caaaaaaggg aataagggcg acacggaaat   3840

gttgaatact catactcttc ctttttcaat attattgaag catttatcag ggttattgtc   3900

tcatgagcgg atacatattt gaatgtattt agaaaaataa acagcgatcg cagctagctc   3960

gtcgtgttca ggaactgttc gatggttcgg agagagtcgc cgcccagaac atacgcgcac   4020

cgatgtcagc agacagcctt attacaagta tattcaagca agtatatccg tagggtgcgg   4080

gtgatttgga tctaaggttc gtactcaaca ctcacgagca gcttgcctat gttacatcct   4140

tttatcagac ataacataat tggagtttac ttacacacgg ggtgtacctg tatgagcacc   4200

acctacaatt gtagcactgg tacttgtaca aagaatttat tcgtacgaat cacagggacg   4260

gccgccctca ccgaaccagc gaatacctca gcggtcccct gcagtgactc aacaaagcga   4320

tatgaacatc ttgcgatggt atcctgctga tagtttttac tgtacaaaca cctgtgtagc   4380

tccttctagc atttttaagt tattcacacc tcaaggggag ggataaatta aataaattcc   4440

aaaagcgaag atcgagaaac taaattaaaa ttccaaaaac gaagttggaa cacaaccccc   4500

cgaaaaaaaa caacaaacaa aaaacccaac aaaataaaca aaaacaaaat aaatatataa   4560

ctaccagtat ctgactaaaa gttcaaatac tcgtacttac aacaaataga aatgagccgg   4620

ccaaaattct gcagaaaaaa atttcaaaca agtactggta taattaaatt aaaaaacaca   4680

tcaaagtatc ataacgttag ttattttatt ttatttaata aaagaaaaca acaagatggg   4740

ctcaaaactt tcaacttata cgatacatac caaataacaa tttagtattt atctaagtgc   4800

ttttcgtaga taatggaata caaatggata tccagagtat acacatggat agtatacact   4860

gacacgacaa ttctgtatct ctttatgtta actactgtga ggcattaaat agagcttgat   4920

atataaaatg ttacatttca cagtctgaac ttttgcagat tacctaattt ggtaagatat   4980

taattatgaa ctgaaagttg atggcggccg catagcttca aaatgtttct actccttttt   5040

tactcttcca gattttctcg gactccgcgc atcgccgtac cacttcaaaa cacccaagca   5100

cagcatacta aatttcccct ctttcttcct ctagggtgtc gttaattacc cgtactaaag   5160
```

```
gtttggaaaa gaaaaaagag accgcctcgt ttctttttct tcgtcgaaaa aggcaataaa   5220
aatttttatc acgtttcttt ttcttgaaaa tttttttttt tgattttttt ctctttcgat   5280
gacctcccat tgatatttaa gttaataaac ggtcttcaat ttctcaagtt tcagtttcat   5340
ttttcttgtt ctattacaac ttttttttact tcttgctcat tagaaagaaa gcatagcaat   5400
ctaatctaag ttttaattac aaaatgctgc cgaaactcgt tataactcac cgagtacacg   5460
atgagatcct gcaactgctg gcgccacatt gcgagctgat gaccaaccag accgacagca   5520
cgctgacgcg cgaggaaatt ctgcgccgct gtcgcgatgc tcaggcgatg atggcgttca   5580
tgcccgatcg ggtcgatgca gactttcttc aagcctgccc tgagctgcgt gtagtcggct   5640
gcgcgctcaa gggcttcgac aatttcgatg tggacgcctg tactgcccgc ggggtctggc   5700
tgaccttcgt gcctgatctg ttgacggtcc cgactgccga gctggcgatc ggactggcgg   5760
tggggctggg gcggcatctg cgggcagcag atgcgttcgt ccgctctggc gagttccagg   5820
gctggcaacc acagttctac ggcacggggc tggataacgc tacggtcggc atccttggca   5880
tgggcgccat cggactggcc atggctgatc gcttgcaggg atggggcgcg accctgcagt   5940
accacgaggc gaaggctctg gatacacaaa ccgagcaacg gctcggcctg cgccaggtgg   6000
cgtgcagcga actcttcgcc agctcggact tcatcctgct ggcgcttccc ttgaatgccg   6060
atacccagca tctggtcaac gccgagctgc ttgccctcgt acggccgggc gctctgcttg   6120
taaacccctg tcgtggttcg gtagtggatg aagccgccgt gctcgcggcg cttgagcgag   6180
gccagctcgg cgggtatgcg gcggatgtat tcgaaatgga agactgggct cgcgcggacc   6240
ggccgcggct gatcgatcct gcgctgctcg cgcatccgaa tacgctgttc actccgcaca   6300
tagggtcggc agtgcgcgcg gtgcgcctgg agattgaacg ttgtgcagcg cagaacatca   6360
tccaggtatt ggcaggtgcg cgcccaatca acgctgcgaa ccgtctgccc aaggccgagc   6420
ctgccgcatg ttgaacaggc cccttttcct ttgtcgatat catgtaatta gttatgtcac   6480
gcttacattc acgccctcct cccacatccg ctctaaccga aaaggaagga gttagacaac   6540
ctgaagtcta ggtccctatt tatttttttt aatagttatg ttagtattaa gaacgttatt   6600
tatatttcaa atttttcttt tttttctgta caaacgcgtg tacgcatgta acattatact   6660
gaaaaccttg cttgagaagg ttttgggacg ctcgaaggct ttaatttgcg ggtaataact   6720
gatataatta aattgaagct ctaatttgtg agtttagtat acatgcattt acttataata   6780
cagtttttta gttttgctgg ccgcatcttc tcaaatatgc ttcccagcct gcttttctgt   6840
aacgttcacc ctctacctta gcatcccttc cctttgcaaa tagtcctctt ccaacaataa   6900
taatgtcaga tcctgtagag accacatcat ccacggttct atactgttga cccaatgcgt   6960
ctcccttgtc atctaaaccc acaccgggtg tcataatcaa ccaatcgtaa ccttcatctc   7020
ttccacccat gtctctttga gcaataaagc cgataacaaa atctttgtcg ctcttcgcaa   7080
tgtcaacagt acccttagta tattctccag tagctaggga gcccttgcat gacaattctg   7140
ctaacatcaa aaggcctcta ggttcctttg ttacttcttc cgccgcctgc ttcaaaccgc   7200
taacaatacc tgggcccacc acaccgtgtg cattcgtaat gtctgcccat tctgctattc   7260
tgtatacacc cgcagagtac tgcaatttga ctgtattacc aatgtcagca aattttctgt   7320
cttcgaagag taaaaaattg tacttggcgg ataatgcctt tagcggctta actgtgccct   7380
ccatggaaaa atcagtcaag atatccacat gtgtttttag taaacaaatt ttgggaccta   7440
atgcttcaac taactccagt aattccttgg tggtacgaac atccaatgaa gcacacaagt   7500
ttgtttgctt ttcgtgcatg atattaaata gcttggcagc aacaggacta ggatgagtag   7560
```

```
cagcacgttc cttatatgta gctttcgaca tgatttatct tcgtttcctg caggtttttg   7620

ttctgtgcag ttgggttaag aatactgggc aatttcatgt ttcttcaaca ccacatatgc   7680

gtatatatac caatctaagt ctgtgctcct tccttcgttc ttccttctgc tcggagatta   7740

ccgaatcaaa gctagcttat cgatgataag ctgtcaaaga tgagaattaa ttccacggac   7800

tatagactat actagatact ccgtctactg tacgatacac ttccgctcag gtccttgtcc   7860

tttaacgagg ccttaccact cttttgttac tctattgatc cagctcagca aaggcagtgt   7920

gatctaagat tctatcttcg cgatgtagta aaactagcta gaccgagaaa gagactagaa   7980

atgcaaaagg cacttctaca atggctgcca tcattattat ccgatgtgac gctgcagctt   8040

ctcaatgata ttcgaatacg ctttgaggag atacagccta atatccgaca aactgtttta   8100

cagatttacg atcgtacttg ttacccatca ttgaattttg aacatccgaa cctgggagtt   8160

ttccctgaaa cagatagtat atttgaacct gtataataat atatagtcta gcgctttacg   8220

gaagacaatg tatgtatttc ggttcctgga gaaactattg catctattgc ataggtaatc   8280

ttgcacgtcg catccccggt tcattttctg cgtttccatc ttgcacttca atagcatatc   8340

tttgttaacg aagcatctgt gcttcatttt gtagaacaaa aatgcaacgc gagagcgcta   8400

atttttcaaa caaagaatct gagctgcatt tttacagaac agaaatgcaa cgcgaaagcg   8460

ctattttacc aacgaagaat ctgtgcttca tttttgtaaa acaaaaatgc aacgcgacga   8520

gagcgctaat ttttcaaaca aagaatctga gctgcatttt tacagaacag aaatgcaacg   8580

cgagagcgct attttaccaa caaagaatct atacttcttt tttgttctac aaaaatgcat   8640

cccgagagcg ctatttttct aacaaagcat cttagattac ttttttctc ctttgtgcgc   8700

tctataatgc agtctcttga taactttttg cactgtaggt ccgttaaggt tagaagaagg   8760

ctactttggt gtctattttc tcttccataa aaaaagcctg actccacttc ccgcgtttac   8820

tgattactag cgaagctgcg ggtgcatttt ttcaagataa aggcatcccc gattatattc   8880

tataccgatg tggattgcgc atactttgtg aacagaaagt gatagcgttg atgattcttc   8940

attggtcaga aaattatgaa cggtttcttc tattttgtct ctatatacta cgtataggaa   9000

atgtttacat tttcgtattg ttttcgattc actctatgaa tagttcttac tacaattttt   9060

ttgtctaaag agtaatacta gagataaaca taaaaaatgt agaggtcgag tttagatgca   9120

agttcaagga gcgaaaggtg gatgggtagg ttatataggg atatagcaca gagatatata   9180

gcaaagagat acttttgagc aat                                           9203
```

<210> SEQ ID NO 14
<211> LENGTH: 6008
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
ttatcgatga taagctgtca aagatgagaa ttaattccac ggactataga ctatactaga     60

tactccgtct actgtacgat acacttccgc tcaggtcctt gtcctttaac gaggccttac    120

cactcttttg ttactctatt gatccagctc agcaaaggca gtgtgatcta agattctatc    180

ttcgcgatgt agtaaaacta gctagaccga gaaagagact agaaatgcaa aaggcacttc    240

tacaatggct gccatcatta ttatccgatg tgacgctgca gcttctcaat gatattcgaa    300

tacgctttga ggagatacag cctaatatcc gacaaactgt tttacagatt tacgatcgta    360
```

```
cttgttaccc atcattgaat tttgaacatc cgaacctggg agttttccct gaaacagata    420
gtatatttga acctgtataa taatatatag tctagcgctt tacggaagac aatgtatgta    480
tttcggttcc tggagaaact attgcatcta ttgcataggt aatcttgcac gtcgcatccc    540
cggttcattt tctgcgtttc catcttgcac ttcaatagca tatctttgtt aacgaagcat    600
ctgtgcttca ttttgtagaa caaaaatgca acgcgagagc gctaattttt caaacaaaga    660
atctgagctg catttttaca gaacagaaat gcaacgcgaa agcgctattt taccaacgaa    720
gaatctgtgc ttcatttttg taaaacaaaa atgcaacgcg acgagagcgc taatttttca    780
aacaaagaat ctgagctgca tttttacaga acagaaatgc aacgcgagag cgctatttta    840
ccaacaaaga atctatactt ctttttttgtt ctacaaaaat gcatcccgag agcgctattt    900
ttctaacaaa gcatcttaga ttactttttt tctcctttgt gcgctctata atgcagtctc    960
ttgataactt tttgcactgt aggtccgtta aggttagaag aaggctactt tggtgtctat   1020
tttctcttcc ataaaaaaag cctgactcca cttcccgcgt ttactgatta ctagcgaagc   1080
tgcgggtgca tttttcaag ataaaggcat ccccgattat attctatacc gatgtggatt   1140
gcgcatactt tgtgaacaga aagtgatagc gttgatgatt cttcattggt cagaaaatta   1200
tgaacggttt cttctatttt gtctctatat actacgtata ggaaatgttt acattttcgt   1260
attgttttcg attcactcta tgaatagttc ttactacaat ttttttgtct aaagagtaat   1320
actagagata aacataaaaa atgtagaggt cgagtttaga tgcaagttca aggagcgaaa   1380
ggtggatggg taggttatat agggatatag cacagagata tatagcaaag agatactttt   1440
gagcaatgtt tgtggaagcg gtattcgcaa tgtttaaacc ccagcccgac ttttaacctc   1500
aatagctagc tacgcaacag acagttaaag ctacgtactc aactatatat tccattgaca   1560
attgacaatt acaactgttt cttctcctgc atcgttctca tcctcattgg cttatctcct   1620
gttatcaatt aattataata atatagtagt tctgaactaa ttacgtgatc gcacgcagta   1680
cggctgacgc gtattattgg accaacaaac cctaaaaatt gtttcatcca attgaacagt   1740
tcacgcaacc gtgattgtgc caaaaaggca ttgccggcct caagtaggcg cccatgctac   1800
gactactgcg gtctaggcgc tcccgtatcc ctcaatcgtg gccctttttcc ggtctacccg   1860
ctgagtcagc cccgcccaac aaaaaaagca caccacaagt tcgacatggt ccaggggcac   1920
ggctgcaggg ttgcggtata aatacagtca ccatttccac cgcacctccg tgctttgttt   1980
ttcaattggc aacctataac acaatgctgc cgaaactcgt tataactcac cgagtacacg   2040
atgagatcct gcaactgctg gcgccacatt gcgagctgat gaccaaccag accgacagca   2100
cgctgacgcg cgaggaaatt ctgcgccgct gtcgcgatgc tcaggcgatg atggcgttca   2160
tgcccgatcg ggtcgatgca gactttcttc aagcctgccc tgagctgcgt gtagtcggct   2220
gcgcgctcaa gggcttcgac aatttcgatg tggacgcctg tactgcccgc ggggtctggc   2280
tgaccttcgt gcctgatctg ttgacggtcc cgactgccga gctggcgatc ggactggcgg   2340
tggggctggg gcggcatctg cgggcagcag atgcgttcgt ccgctctggc gagttccagg   2400
gctggcaacc acagttctac ggcacggggc tggataacgc tacggtcggc atccttggca   2460
tgggcgccat cggactggcc atggctgatc gcttgcaggg atggggcgcg accctgcagt   2520
accacgaggc gaaggctctg gatacacaaa ccgagcaacg gctcggcctg cgccaggtgg   2580
cgtgcagcga actcttcgcc agctcggact tcatcctgct ggcgcttccc ttgaatgccg   2640
atacccagca tctggtcaac gccgagctgc ttgccctcgt acggccgggc gctctgcttg   2700
```

```
taaacccctg tcgtggttcg gtagtggatg aagccgccgt gctcgcggcg cttgagcgag   2760

gccagctcgg cgggtatgcg gcggatgtat tcgaaatgga agactgggct cgcgcggacc   2820

ggccgcggct gatcgatcct gcgctgctcg cgcatccgaa tacgctgttc actccgcaca   2880

tagggtcggc agtgcgcgcg gtgcgcctgg agattgaacg ttgtgcagcg cagaacatca   2940

tccaggtatt ggcaggtgcg cgcccaatca acgctgcgaa ccgtctgccc aaggccgagc   3000

ctgccgcatg ttgagttaat tcaaattaat tgatatagtt ttttaatgag tattgaatct   3060

gtttagaaat aatggaatat tatttttatt tatttattta tattattggt cggctctttt   3120

cttctgaagg tcaatgacaa aatgatatga aggaaataat gatttctaaa attttacaac   3180

gtaagatatt tttacaaaag cctagctcat cttttgtcat taattaaggc gcgcctttcc   3240

ataggctccg cccccctgac gagcatcaca aaaatcgacg ctcaagtcag aggtggcgaa   3300

acccgacagg actataaaga taccaggcgt ttccccctgg aagctccctc gtgcgctctc   3360

ctgttccgac cctgccgctt accggatacc tgtccgcctt tctcccttcg ggaagcgtgg   3420

cgctttctca tagctcacgc tgtaggtatc tcagttcggt gtaggtcgtt cgctccaagc   3480

tgggctgtgt gcacgaaccc cccgttcagc ccgaccgctg cgccttatcc ggtaactatc   3540

gtcttgagtc caacccggta agacacgact tatcgccact ggcagcagcc actggtaaca   3600

ggattagcag agcgaggtat gtaggcggtg ctacagagtt cttgaagtgg tggcctaact   3660

acggctacac tagaagaaca gtatttggta tctgcgctct gctgaagcca gttaccttcg   3720

gaaaaagagt tggtagctct tgatccggca aacaaaccac cgctggtagc ggtggttttt   3780

ttgtttgcaa gcagcagatt acgcgcagaa aaaaaggatc tcaagaagat cctttgatct   3840

tttctacggg gtctgacgct cagtggaacg aaaactcacg ttaagggatt ttggtcatga   3900

gattatcaaa aaggatcttc acctagatcc ttttaaatta aaaatgaagt tttaaatcaa   3960

tctaaagtat atatgagtaa acttggtctg acagttacca atgcttaatc agtgaggcac   4020

ctatctcagc gatctgtcta tttcgttcat ccatagttgc ctgactcccc gtcgtgtaga   4080

taactacgat acgggagggc ttaccatctg gccccagtgc tgcaatgata ccgcgagacc   4140

cacgctcacc ggctccagat ttatcagcaa taaaccagcc agccggaagg gccgagcgca   4200

gaagtggtcc tgcaacttta tccgcctcca tccagtctat taattgttgc cgggaagcta   4260

gagtaagtag ttcgccagtt aatagtttgc gcaacgttgt tgccattgct acaggcatcg   4320

tggtgtcacg ctcgtcgttt ggtatggctt cattcagctc cggttcccaa cgatcaaggc   4380

gagttacatg atcccccatg ttgtgcaaaa aagcggttag ctccttcggt cctccgatcg   4440

ttgtcagaag taagttggcc gcagtgttat cactcatggt tatggcagca ctgcataatt   4500

ctcttactgt catgccatcc gtaagatgct tttctgtgac tggtgagtac tcaaccaagt   4560

cattctgaga atagtgtatg cggcgaccga gttgctcttg cccggcgtca atacgggata   4620

ataccgcgcc acatagcaga actttaaaag tgctcatcat tggaaaacgt tcttcggggc   4680

gaaaactctc aaggatctta ccgctgttga gatccagttc gatgtaaccc actcgtgcac   4740

ccaactgatc ttcagcatct tttactttca ccagcgtttc tgggtgagca aaaacaggaa   4800

ggcaaaatgc cgcaaaaaag ggaataaggg cgacacggaa atgttgaata ctcatactct   4860

tcctttttca atattattga agcatttatc agggttattg tctcatgagc ggatacatat   4920

ttgaatgtat ttagaaaaat aaacagcgat cgcgcggccg cgggtaataa ctgatataat   4980

taaattgaag ctctaatttg tgagtttagt atacatgcat ttacttataa tacagttttt   5040

tagttttgct ggccgcatct tctcaaatat gcttcccagc ctgcttttct gtaacgttca   5100
```

-continued

```
ccctctacct tagcatccct tccctttgca aatagtcctc ttccaacaat aataatgtca   5160

gatcctgtag agaccacatc atccacggtt ctatactgtt gacccaatgc gtctcccttg   5220

tcatctaaac ccacaccggg tgtcataatc aaccaatcgt aaccttcatc tcttccaccc   5280

atgtctcttt gagcaataaa gccgataaca aaatctttgt cgctcttcgc aatgtcaaca   5340

gtacccttag tatattctcc agtagctagg gagcccttgc atgacaattc tgctaacatc   5400

aaaaggcctc taggttcctt tgttacttct tccgccgcct gcttcaaacc gctaacaata   5460

cctgggccca ccacaccgtg tgcattcgta atgtctgccc attctgctat tctgtataca   5520

cccgcagagt actgcaattt gactgtatta ccaatgtcag caaattttct gtcttcgaag   5580

agtaaaaaat tgtacttggc ggataatgcc tttagcggct taactgtgcc ctccatggaa   5640

aaatcagtca agatatccac atgtgttttt agtaaacaaa ttttgggacc taatgcttca   5700

actaactcca gtaattcctt ggtggtacga acatccaatg aagcacacaa gtttgtttgc   5760

ttttcgtgca tgatattaaa tagcttggca gcaacaggac taggatgagt agcagcacgt   5820

tccttatatg tagctttcga catgatttat cttcgtttcc tgcaggtttt tgttctgtgc   5880

agttgggtta agaatactgg gcaatttcat gtttcttcaa caccacatat gcgtatatat   5940

accaatctaa gtctgtgctc cttccttcgt tcttccttct gctcggagat taccgaatca   6000

aagctagc                                                            6008
```